(12) United States Patent
Peters et al.

(10) Patent No.: US 7,525,016 B1
(45) Date of Patent: Apr. 28, 2009

(54) IDENTIFICATION OF SYN-COPALYL DIPHOSPHATE SYNTHASE

(75) Inventors: Reuben J. Peters, Ames, IA (US); Meimei Xu, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 261 days.

(21) Appl. No.: 11/135,267

(22) Filed: May 23, 2005

Related U.S. Application Data

(60) Provisional application No. 60/573,472, filed on May 21, 2004.

(51) Int. Cl.
  *C12N 15/29* (2006.01)
  *C12N 15/52* (2006.01)
  *C12N 15/82* (2006.01)
  *A01H 5/00* (2006.01)

(52) U.S. Cl. .................. 800/298; 800/278; 800/279; 435/69.1; 435/468

(58) Field of Classification Search ............ None
See application file for complete search history.

(56) References Cited

U.S. PATENT DOCUMENTS

2007/0141574 A1* 6/2007 Keasling et al. ............ 435/6

OTHER PUBLICATIONS

Sakamoto T. et al.; Plant Physiology, Apr. 2004, vol. 134, pp. 1642-1653.*
Otomo K, et al. The Plant Journal (2004) vol. 39, pp. 886-893.*
Prisic S. et al. Plant Physiology; vol. 136, pp. 4228-4236.*
Otomo K. et al. The Plant Journal 2004; vol. 39, pp. 886-893.*
Sakamoto T. et al. Plant Physiology, Apr. 2004; vol. 134, pp. 1642-1653.*
Cho et al., "Molecular cloning and characterization of a cDNA encoding ent-cassa-12,15-diene synthase, a putative diterpenoid phytoalexin biosynthetic enzyme, from suspension-cultured rice cells treated with a chitin elicitor", The Plant Journal, 37:1-3 (2004).
Nemoto et al., "Stemar-13-3n3 synthase, a diterpene cyclase involved in the biosynthesis of the phytoalexin oryzalexin S in rice", FEBS Letters 571:182-186 (2004).
Otomo et al., "Diterpene Cyclases Responsible for the Biosynthesis of Phytoalexins, Momilactones A, B, and Oryzalexins A-F in Rice", Biosci. Biotechnol. Biochem. 68(9):2001-2006 (2004).
Otomo et al., Biological functions of ent- and syn-copalyl diphosphate synthases in rice: key enzymes for the branch point of gibberellin and phytoalexin biosynthesis.
Prisic et al., "Rice Contains Two Disparate ent-Copalyl Diphosphate Synthases with Distinct Metabolic Functions", Plant Physiology, vol. 136:4228-4236 (2004).
Sakamoto et al., "An Overview of Gibberellin Metabolism Enzyme Genes and Their Related Mutants in Rice", Plant Physiology, vol. 134:1642-1653 (2004).
Wilderman et al., "Identification of Syn-Pimara-7,15-Diene Synthase Reveals Functional Clustering of Terpene Synthases Involved in Rice Phytoalexin/Allelochemical Biosynthesis", Plant Physiology, 135:2098-2105 (2004).

* cited by examiner

*Primary Examiner*—Russell Kallis
(74) *Attorney, Agent, or Firm*—McKee, Voorhees & Sease, P.L.C.

(57) ABSTRACT

The present invention relates to the isolation, purification, sequencing, and functional characterization of the class I and II terpene sequences $OsCPS1_{ent}$, $OsCPS2_{ent}$, $OsCPS4_{syn}$, and OsDTS2. Transcriptional control of $OsCPS1_{ent}$ provides a means of regulating production of gibberellin phytohormone, while transcriptional control of $OsCPS2_{ent}$, OsDTS2, and $OsCPS4_{syn}$ provides a means of regulating defensive phytochemical biosynthesis. Further, these enzymatic genes offers a means by which terpenoid production may be more generally modulated, specifically including genetic engineering, as well as ex vivo uses.

4 Claims, 15 Drawing Sheets

Fig. 2

```
>OsCPS1ent (Os27; AK100333) SEQ ID NO:2
MIHLHSPPTA PAAFGGAGSA DWRRRRRWSW SSSSRAPVAK GGHLRPCVWR
RGGDDGGGED HHADSGGGGG GGAAWRARAT TAGVSSSSST AKGLQANIIE
HETPRITKWP NESRDLDDHQ QNNEADEEAD DELQPLVEQV RSMLSSMEDG
AITASAYDTA WVALVPRLDG EGGTQFPAAV RWIVGSQLAD GSWGDEALFS
AYDRVINTLA CVVALTRWSL HHDQCKQGLQ FLNLNLWRLA EEEPDTMPIG
FEIAFPSLVE AARGLGIDFP YDHPALKGIY ANRELKLKRI PKDMMHIVPT
SILHSLEGMP GLDWQRLLKL QCSDGSFLFS PSATAYALMQ TGDKKCFAYI
DRIIKKFDGG VPNVYPVDLF EHIWVVDRLE RLGISRYFQR EIEQNMDYVN
RHWTEDGICW ARNSNVKEVD DTAMAFRLLR LHGYNVSPSV FKNFEKDGEF
FCFVGQSTQA VTGMYNLNRA SQISFPGEDI LQRARNFSYE FLREREAQGT
LHDKWIISKD LPGEVQYTLD FPWYASLPRV EARTYIGQYG GNDDVWIGKT
LYRMPIVNNA TYLELAKQDF NRCQALHQHE LQGLQKWFIE NGLEAFGMTP
EDVLRAYFLA AACIFEPNRA SERLAWARVS VLANTISRHF YSDMSSMKRM
ERFMWSSLYE ENGNVLGLEG YAKDGILART LCQLIDLLSQ ETPPVREGQK
CIHNLIRCAW IEWMMQQINM KDGRYDKGRV MHPGSCTVHN KETCLLIAQI
VEICAGRIEE AASMINNTEG SWFIQLASSI CDSLHAKMLL SQDTKKNETT
INQIDKEIEL GMQELAQYLL PRVDDRRINN KTKQTFLSIV KSCYYAANCS
PHMLDQHISE VIFEQVI
```

*Fig. 9A*

Coding SEQ ID NO:9
ATGATTCACCTCCACTCCCCGCCGACGGCGCCCGCCGCATTCGGCGGCGCCGGCTC
GGCGGACTGGCGGCGGCGGCGGCGGTGGTCATGGTCGTCGTCGTCCCGCGCTCCGGTGGC
TAAAGGTGGCCATCTTCGTCCGTGCGTTTGGCGGCGCGGCGGCGACGACGGCGGCGGCGA
GGATCATCACGCCGACAGCGGCGGCGGCGGCGGAGGAGGAGCGGCGTGGAGGGCGCGGGC
CACCACCGCCGGCGTGTCGAGCTCCAGCAGTACAGCCAAAGGGCTGCAAGCCAACATCAT
CGAACATGAGACCCCCGGATCACGAAATGGCCCAATGAATCACGCGACCTCGACGATCA
CCAACAAAACAACGAGGCTGATGAGGAGGCAGATGATGAGCTGCAGCCACTGGTCGAGCA
GGTGAGGTCGATGCTGTCGTCCATGGAGGACGGCGCGATCACCGCGTCGGCGTACGACAC
GGCGTGGGTGGCGCTGGTGCCGCGGCTGGACGGCGAGGGCGGCACGCAGTTCCCGGCCGC
CGTGCGGTGGATCGTCGGCAGCCAGCTCGCCGACGGGTCGTGGGGCGACGAGGCGCTCTT
CTCCGCCTACGACCGCGTCATCAACACCCTCGCCTGCGTCGTCGCCCTCACCAGATGGTC
CCTCCACCATGACCAGTGCAAGCAAGGGCTTCAGTTTCTGAATCTGAACTTGTGGAGGTT
AGCAGAGGAGGAGCCGGATACGATGCCGATTGGGTTTGAGATTGCATTCCCTTCTCTTGT
GGAGGCAGCTAGGGGTTTGGGTATTGATTTCCCATATGATCACCCTGCTCTCAAGGGCAT
TTATGCAAACAGAGAACTCAAGCTTAAGAGGATTCCAAAGGACATGATGCATATAGTCCC
AACTTCAATTCTGCATAGCCTTGAAGGGATGCCTGGGCTGGATTGGCAGAGGCTTCTGAA
GCTCCAATGCAGTGATGGATCCTTCTTGTTCTCCCCTTCAGCTACTGCTTATGCTCTCAT
GCAGACCGGTGACAAGAAATGCTTCGCGTACATCGACAGGATCATTAAGAAATTCGACGG
TGGCGTTCCGAACGTTTACCCGGTCGATCTTTTTGAGCACATATGGGTTGTCGATCGGTT
GGAGCGTCTTGGGATATCGCGGTACTTCCAACGAGAGATTGAACAGAACATGGACTATGT
CAACAGGCACTGGACTGAAGATGGGATTTGCTGGGCTAGGAACTCCAATGTAAAAGAAGT
GGATGACACCGCTATGGCTTTCCGTCTACTACGCCTCCATGGATACAATGTATCACCAAG
TGTGTTCAAGAATTTTGAGAAGGATGGGGAGTTCTTCTGTTTTGTGGGGCAATCAACTCA
AGCAGTCACTGGGATGTATAACCTGAACAGAGCATCTCAGATAAGTTTTCCAGGAGAAGA
CATTTTGCAGCGTGCAAGGAATTTCTCATATGAGTTCCTTAGAGAAAGAGAAGCCCAGGG
GACACTTCATGATAAATGGATCATCTCCAAGGACCTACCAGGAGAGGTACAATACACACT
AGATTTTCCTTGGTATGCGAGCTTGCCACGCGTCGAGGCAAGAACATACATAGGTCAATA
TGGTGGAAATGATGACGTCTGGATTGGAAAGACACTCTACAGGATGCCAATTGTGAATAA
CGCTACATATCTCGAGTTGGCGAAACAGGATTTCAACCGTTGTCAAGCTCTACATCAGCA
TGAGTTGCAGGGTCTACAAAAGTGGTTCATTGAGAATGGCCTGGAAGCTTTTGGGATGAC
ACCTGAAGATGTTTTGAGAGCTTATTTTTTGGCTGCCGCGTGCATTTTCGAACCAAACCG
TGCCTCTGAGCGACTTGCATGGGCTAGAGTGTCAGTGCTGGCCAACACTATTTCTAGGCA
TTTTTACAGCGATATGTCAAGCATGAAAAGGATGGAGCGTTTCATGTGGAGCAGCCTCTA
TGAAGAAAATGGCAATGTTTTGGGGCTAGAAGGATATGCAAAAGATGGAATCCTTGCGAG
GACACTTTGTCAACTTATAGATTTGTTGTCTCAAGAGACACCGCCAGTTCGAGAAGGTCA
AAAGTGTATTCATAATCTCATAAGATGTGCTTGGATTGAATGGATGATGCAACAAATCAA
TATGAAGGATGGCAGATATGACAAAGGCAGAGTTATGCATCCAGGGTCATGCACTGTTCA
TAATAAAGAAACATGTTTACTTATTGCTCAAATTGTTGAAATTTGTGCTGGACGAATTGA
GGAGGCAGCATCTATGATAAATAACACCGAAGGTTCTTGGTTTATTCAACTTGCTTCCTC
TATTTGCGATTCTCTTCATGCCAAGATGTTACTTTCACAGGATACCAAGAAAAATGAGAC
AACAATAAATCAAATTGACAAGGAAATTGAGTTGGGTATGCAAGAACTTGCTCAATATCT
TCTTCCAAGAGTTGATGATAGAAGAATTAACAACAAAACCAAGCAGACCTTCTTGAGCAT
TGTGAAAAGCTGTTACTATGCTGCCAATTGCTCACCACATATGCTTGACCAACACATTTC
TGAAGTGATTTTTGAGCAAGTTATTTGA
```

*Fig. 9B*

```
>OsCPS2ent (our indica Os31 sequence; TIGR# TC187448) SEQ ID NO:3
MQMQVLTAAS  SLPRATLLRP  AAAEPWRQSF  LQLQARPIQR  PGIMLHCKAQ
LQGQETRERR  QLDDDEHARP  PQGGDDDVAA  STSELPYMIE  SIKSKLRAAR
NSLGETTVSA  YDTAWIALVN  RLDGGGERSP  QFPEAIDWIA  RNQLPDGSWG
DAGMFIVQDR  LINTLGCVVA  LATWGVHEEQ  RARGLAYIQD  NLWRLGEDDE
EWMMVGFEIT  FPVLLEKAKN  LGLDINYDDP  ALQDIYAKRQ  LKLAKIPREA
LHARPTTLLH  SLEGMENLDW  ERLLQFKCPA  GSLHSSPAAS  AYALSETGDK
ELLEYLETAI  NNFDGGAPCT  YPVDNFDRLW  SVDRLRRLGI  SRYFTSEIEE
YLEYAYRHLS  PDGMSYGGLC  PVKDIDDTAM  AFRLLRLHGY  NVSSSVFNHF
EKDGEYFCFA  GQSSQSLTAM  YNSYRASQIV  FPGDDDGLEQ  LRAYCRAFLE
ERRATGNLRD  KWVIANGLPS  EVEYALDFPW  KASLPRVETR  VYLEQYGASE
DAWIGKGLYR  MTLVNNDLYL  EAAKADFTNF  QRLSRLEWLS  LKRWYIRNNL
QAHGVTEQSV  LRAYFLAAAN  IFEPNRAAER  LGWARTAILA  EAIASHLRQY
SANGAADGMT  ERLISGLASH  DWDWRESNDS  AARSLLYALD  ELIDLHAFGN
ASDSLREAWK  QWLMSWTNES  QGSTGGDTAL  LLVRTIEICS  GRHGSAEQSL
KNSEDYARLE  QIASSMCSKL  ATKILAQNGG  SMDNVEGIDQ  EVDVEMKELI
QRVYGSSSND  VSSVTRQTFL  DVVKSFCYVA  HCSPETIDGH  ISKVLFEDVN
```

Fig.10A

```
5' UTR SEQ ID NO:10
actacgccgagacagtgtggtggtgagccggtgatcgatcttgcatcttgcgagcacacgggatt
ccagatcgatcgagctatagctagctagctaattagttaccacgtacgaacgagtactttacaac
tcgatcagttcatcaaattaactcgatcagtggttaagtttcgcacgacacacgcgcgcggatcg
gaagccatc
```

Fig.10B

```
Coding SEQ ID NO:11
atgcagatgcaggtgctcaccgctgcttcttcgctccctcgcgcgacctttgctccggccggcggc
tgccgagccatggcgccaatctttcctgcagctgcaggctcgtccaatccagcgaccaggtatca
tgctacactgcaaggcccagctacaggggcaggaaacgcgcgagcgtcgtcagctcgacgacgat
gaacacgctagaccaccacagggcggcgacgacgacgtcgcagcaagcaccagcgagctaccta
catgatcgagtccatcaaatccaagctgagggcggccaggaacagcctcggcgagaccaccgtct
ccgcctacgacacggcgtggatcgcgctcgtcaaccgcctcgacggcggcggcgagaggagcccc
cagttcccggaggccatcgactggatcgcccggaaccagctgcccgacggctcgtggggcgacgc
cggcatgttcatcgtccaggaccggctcatcaacacgctgggctgcgtcgtggcgctcgcgacgt
ggggcgtccacgaggagcagcgcgcgaggggcctcgcctacatccaggacaacctctggaggctc
ggcgaggacgacgaggagtggatgatggtcgggttcgagatcaccttcccgttctcctcgagaa
ggccaagaacctgggcctggacatcaactatgatgaccctgccttgcaggacatatatgccaaga
gacaattaaagctcgcaaagattcctagagaagcactgcatgctaggccgaccaccttgctccat
agcttagagggaatggaaaacttggactgggaaaggttgctacagttcaagtgtccagctggctc
cttacattcctcacctgctgcgtcagcttacgctctcagcgaaacaggtgacaaggagttgctcg
aatacctggaaacagccatcaacaattttgacggtggagcaccatgcacctaccctgtcgacaac
tttgaccgcttatggtcggtcgatcggttgaggcggctaggaatatcgaggtacttcacgagtga
gattgaagaatacttggagtacgcctacaggcacctgagtccagatggcatgagctacggcgggc
tctgtccggtcaaggacatcgacgacacggccatggctttccgtctcctccgtctgcatggctac
aatgtctcatcatcggtgttcaatcacttcgagaaggacggggagtacttctgcttcgcggggca
gtcgagccagtcgctgacggcgatgtacaactcctaccgcgcctcgcagatcgtcttcccggcg
acgacgacggcctggagcagctcagggcctactgccgcgccttcctcgaggagcggcgagccacc
ggcaacctcagggacaagtgggtcatcgccaatggcttgcccagcgaggtcgagtacgcgctgga
tttcccatggaaggcaagcttgccgcgagtcgagacgagggtgtatctggagcagtacggcgcta
gcgaggacgcgtggatcggcaagggactctacaggatgaccctagtcaacaacgacctgtacctt
gaggcggcaaaggctgacttcaccaacttccagaggctctcccggctcgagtggctcagcctgaa
aaggtggtacatcaggaacaatctgcaagcgcacggcgtgaccgaacagagcgtgctgagagcct
acttcttagccgcggcgaacatcttcgagcccaaccgggcggcggaacgcctgggatgggctcgc
acggcgatcctcgccgaggccatcgcgtcacacctccgacagtacagtgccaacggcgccgccga
cggcatgacagagaggctcatcagtggactcgccagccacgactgggactggagggaatcaaacg
attcagcagcgaggagcttactgtacgcacttgatgagctcatcgacctccatgcgttcggcaat
gcttctgacagcctacgtgaagcgtggaagcagtggctcatgtcatggacaaacgagagccaagg
atcaactggtggggataccgcattgctgctagttcgcacaatcgagatctgctcaggacggcacg
gttcagccgagcagagcctgaagaacagtgaagactacgccaggcttgagcagatcgcctcttcc
atgtgcagcaaacttgccaccaaaattcttgctcagaatggaggaagcatggacaacgttgaggg
tatagaccaggaagtggatgttgagatgaaagagctcatccagcgtgtctacgggagcagcagca
acgatgtcagcagcgtgacgaggcagacatttctcgacgtggtgaagagcttttgctacgtcgct
cattgctcgcccgaaacaatcgatgggcacatctccaaggttttgttcgaggatgtcaattag
```

*Fig.10C*

```
3' UTR SEQ ID NO:12
gaaaatggttgactactagaaaggcaataaaaacaagagttgtgtctaccagcatggctcgtaaa
gtgatgactgcgaaaattttctcaaagtgagatgaatttagtcgatatttgtttcacttgatggt
acaccagatacacatgttgttataaaaaaaaaaaaaaaaaaaaaaa
```

*Fig.10D*

```
>OsCPSsyn (our indica Os28 sequence; AY530101) SEQ ID NO:4
MPVFTASFQC  VTLFGQPASA  ADAQPLLQGQ  RPFLHLHARR  RRPCGPMLIS
KSPPYPASEE  TREWEAEGQH  EHTDELRETT  TTMIDGIRTA  LRSIGEGEIS
ISAYDTSLVA  LLKRLDGGDG  PQFPSTIDWI  VQNQLPDGSW  GDASFFMMGD
RIMSTLACVV  ALKSWNIHTD  KCERGLLFIQ  ENMWRLAHEE  EDWMLVGFEI
ALPSLLDMAK  DLDLDIPYDE  PALKAIYAER  ERKLAKIPRD  VLHAMPTTLL
HSLEGMVDLD  WEKLLKLRCL  DGSFHCSPAS  TATAFQQTGD  QKCFEYLDGI
VKKFNGGVPC  IYPLDVYERL  WAVDRLTRLG  ISRHFTSEIE  DCLDYIFRNW
TPDGLAHTKN  CPVKDIDDTA  MGFRLLRLYG  YQVDPCVLKK  FEKDGKFFCL
HGESNPSSVT  PMYNTYRASQ  LKFPGDDGVL  GRAEVFCRSF  LQDRRGSNRM
KDKWAIAKDI  PGEVEYAMDY  PWKASLPRIE  TRLYLDQYGG  SGDVWIGKVL
HRMTLFCNDL  YLKAAKADFS  NFQKECRVEL  NGLRRWYLRS  NLERFGGTDP
QTTLMTSYFL  ASANIFEPNR  AAERLGWARV  ALLADAVSSH  FRRIGGPKNL
TSNLEELISL  VPFDDAYSGS  LREAWKQWLM  AWTAKESSQE  SIEGDTAILL
VRAIEIFGGR  HVLTGQRPDL  WEYSQLEQLT  SSICRKLYRR  VLAQENGKST
EKVEEIDQQL  DLEMQELTRR  VLQGCSAINR  LTRETFLHVV  KSFCYVAYCS
PETIDNHIDK  VIFQDVI
```

*Fig. 11A*

```
5' UTR SEQ ID NO:13
cgactggagcacgtaggacactgacatggactgaaggagtagtaaaatcattcatccca
atatctattgcatctgcaagagcgatcgagagagaaaaacaagatctatctatagcagc
tagctagctagcacaagaacgat
```

*Fig. 11B*

Coding SEQ ID NO:14
atgccggtcttcactgcgtcattccagtgtgtcaccttgtttgggcagccagcatcggc
ggccgacgcccagccattgctgcaagggcaacggccgttcctacaccttcacgctcgcc
gccgtcgaccatgcgggcccatgctaataagcaaatcaccgccgtacccggcctcggaa
gaaacacgcgaatgggaagcagaaggacaacatgaacacacggatgaactaagagagac
gacgacaaccatgatcgatggcatcaggacagcactgagatcaatcggagagggagaga
ttagcatctcagcctatgacacttcgttggttgcccttctgaagaggctagatggggt
gatggtcctcagttcccatcaaccatcgactggatcgttcagaatcagctaccggatgg
ttcatggggtgatgcctccttcttcatgatgggagaccggatcatgagcaccctcgctt
gtgttgtagcgttgaagtcatggaacatccacaccgataaatgcgagagaggtttgttg
tttatccaagaaatatgtggaggttggcccatgaggaagaagactggatgctagttgg
atttgagattgccttgccctcgctcctagacatggctaaggacctggatcttgacatcc
cttacgatgagccagccttgaaagcaatatatgccgagagagaaaggaagcttgccaag
attccaagagacgtgctacacgctatgccaacaactttacttcatagccttgagggaat
ggttgacttggactgggaaaagctcctcaagctccggtgtctcgatggtccttccatt
gctcccctgcttcgacggctactgctttccagcaaacaggagaccagaaatgctttgaa
tacctcgatggaatcgtcaaaaagttcaatggaggagttccctgtatctacccttgga
tgtgtacgaacgcttatgggccgtcgataggctgacgaggctgggcatatcaaggcact
tcacaagtgaaattgaggattgcttagactacattttcaggaactggactccagatgga
ttagctcacacaaagaactgcccggtaaaagatatcgatgacacggccatgggtttccg
tctcctccgactttacggctaccaagtcgacccatgcgtgttgaagaagttcgaaaagg
atggcaagttcttctgcttgcacggggagtccaacccatcctctgtcaccccaatgtac
aacacttaccgggcctcccagctcaaatttcctggcgatgacggtgtccttgggcgagc
tgaggtgttttgccgctcattcctccaagacaggagaggctcaaacagaatgaaggaca
agtgggccatcgccaaggatatcccaggcgaggttgagtatgctatggactacccatgg
aaagcaagtttaccgcgtattgaaacaaggttgtacttggatcaatatggaggtagtgg
cgatgtatggattgggaaggtcctgcacaggatgactcttttctgcaacgacctgtacc
tcaaggcagctaaagctgacttcagtaatttccagaaagagtgccgagttgagttgaat
ggccttagaaggtggtatttgaggagtaatctggagaggtttggagggactgatccaca
gactacactgatgacatcctacttcttagcttcagcgaacatcttcgagccaaaccgag
cagcggaacgtcttggatgggctcgcgtagcgttgcttgccgatgccgtctcctctcac
ttcaggagaatcggggaccaaaaaatttgaccagtaatcttgaagagcttatcagcct
tgttccatttgacgacgcttattctggcagtcttcgtgaagcttggaagcagtggctca
tggcatggactgcaaaggagagcagccaggagtcaattgaaggggacacggcaatattg
ttggttcgtgccatcgagatttttggaggacggcatgttttgactgggcaaagaccgga
cctttgggagtattcccagctcgagcagctcacctcctccatctgccgcaaactgtaca
ggagggttcttgcccaggagaatgggaaaagtacggagaaagttgaggagatagaccag
caattggatttggagatgcaggaattgactcggcgcgttcttcagggctgcagcgctat
taacagactaacccggggagacgtttctccatgtggtgaagagcttctgctatgtcgcct
actgctcacctgagacaattgataaccacatcgacaaggtcatattccaagatgtgatt
tag

Fig. 11C

3' UTR SEQ ID NO:15
gaacaaattaccccgactcatctacactccttataaaagagagtagtggtggtattggt
tctgccaccccccaccccactaccaactcccgacttttgtataataaagatgtgtcttt
tgtattaagtttgttgtggtgtacctcgtgttttttctgggatagggattaatttcgtg
gctttcatgaaaggtaatttccgagtatgatactgaacgccaacgacaaaaaaaaaaa
aaaaaaaaa

Fig. 11D

```
>OsDTS2 (our indica Os21 sequence; AY616862) SEQ ID NO:8
MASPMEAVAR SSLVLAPRRR RALGLLPAAA APFVLDCRRR HNGGMRRPHV
SFACSAELDT GRRQLPSTGT RAVMSSCPGY VEGRMVGENT SQINMGREAR
IRRHLENPEF LPSSYDIAWV AMVPLPGTDH LQAPCFPECV EWILQNQHSN
GSWGVNEFDS SASKDILLST LACIIALEKW NVGSEQIRRG LHFIAKNFSI
VIDDQIAAPI GFNLTFPAMV NLAIKMGLEF PASEISIDQI LHLRDMELKR
LSGEESLGKE AYFAYIAEGL EESMVDWSEV MKFQGKNGSL FNSPAATAAA
LVHRYDDKAL GYLYSVVNKF GGEVPTVYPL NIFSQLSMVD TLVNIGISRH
FSSDIKRILD KTYILWSQRD EEVMLDLPTC AMAFRLLRMN GYGVSSDDLS
HVAEASTFHN SVEGYLDDTK SLLELYKASK VSLSENEPIL EKMGCWSGSL
LKEKLCSDDI RGTPILGEVE YALKFPFYAT LEPLDHKWNI ENFDARAYQK
IKTKNMPCHV NEDLLALAAE DFSFCQSTYQ NEIQHLESWE KENKLDQLEF
TRKNLINSYL SAAATISPYE LSDARIACAK SIALTLVADD FFDVGSSKEE
QENLISLVEK WDQYHKVEFY SENVKAVFFA LYSTVNQLGA MASAVQNRDV
TKYNVESWLD YLRSLATDAE WQRSKYVPTM EEYMKNSIVT FALGPTILIA
LYFMGQNLWE DIVKNAEYDE LFRLMNTCGR LQNDIQSFER ECKDGKLNSV
SLLVLDSKDV MSVEEAKEAI NESISSCRRE LLRLVVREDG VIPKSCKEMF
WNLYKTSHVF YSQADGFSSP KEMMGAMNGV IFEPLKTRGN
```

*Fig. 12A*

Coding SEQ ID NO:16
atggcgagtcctatggaagctgtagcccgttccagcctcgtgctcgcacctcgccggcg
gcgagccctcggcctcctcccggcggcggccgcccattcgtgctagattgtcgccggc
ggcataacggaggaatgcgtcgtcctcatgtcagcttcgcctgctcggccgagctcgac
accggtcgccggcagcttccttccacggggactcgagcggtgatgtcgtcctgtcccgg
atatgttgaggggaggatggtaggagaaaatacaagtcagataaacatgggacgggagg
ctagaatacgtaggcacttggagaacccggagttcttaccatcttcatatgacatagca
tgggtggctatggtgccattgccgggcactgatcatcttcaagctccatgcttccctga
atgtgtggaatggatactacaaaaccaacacagtaatgggtcgtggggtgtcaatgaat
ttgactcatcagccagcaaggatattcctatccactttggcatgtattattgcactt
gagaaatggaatgtcggttcggagcaaataaggagaggattacattttatcgcaaagaa
tttctccattgttattgatgaccagattgctgcacctataggcttcaacctcacattcc
ctgctatggttaaccttgccattaagatgggtttggaatttcctgccagtgaaattagt
attgatcagattcttcacctccgtgatatggaattgaaaagactgtctggtgaggaatc
tttggggaaagaggcatatttcgcctatattgctgaaggtctagaagaaagcatggtgg
attggagtgaagttatgaagttccaggggaagaatggatcattgttcaactccccggct
gcaactgctgctgcattagtccacagatacgatgataaagccctgggatacctatattc
tgttgtcaataaatttggaggtgaagtaccaaccgtgtatccgctaaatatattttctc
agctttcaatggtggatactctcgtcaatattggaatatctcggcacttttctagtgat
ataaagcgcattttggataagacatacattttatggtcacagagagatgaggaagtaat
gctggatttaccaacatgcgcaatggcatttcgccttttgcgtatgaacggatatggtg
tttcctcagatgacttgtccatgttgctgaagcctcaactttcataactcagttgaa
ggatacttagatgatacaaaatccttattagaattgtacaaagcttcaaaagtcagttt
atcagaaaatgagccaatcctagagaaatgggttgctggtcaggtagcttattgaaag
aaaaattgtgctccgatgacatccgaggaacaccaatccttggagaggtagaatatgct
ctcaaatttccattttatgccacgctggaacctctagaccacaagtggaacattgaaaa
ttttgatgccagggcttatcagaagataaagaccaaaaacatgccgtgccatgtcaatg
aagatctcttggctttggctgctgaagatttcagcttttgtcagtcaacttaccaaaat
gaaatccagcaccttgaaagttgggagaaagaaaataagctggaccagctcgaattac
gcggaagaatctaataaacagctatctctctgctgctgccaccataagcccttatgaat
tgtctgatgctcgcattgcgtgtgcaaaatctattgcgctcacacttgttgccgatgac
ttttttgatgtcggaagttccaaagaagaacaagaaaatctcatatccttagtcgagaa
gtgggatcagtatcataaagttgagttctactctgagaatgtaaaagcagtattttcg
ctctatattctacggttaaccagcttggagcaatggcttccgcagtacagaaccgcgac
gttacaaaatacaatgttgaatcgtggttggattatttgaggtctttagcgacagatgc
agaatggcaacggagcaaatatgtgccaacaatggaggaatacatgaaaaattcaattg
tgacattcgcattgggaccaactatactcatagcactgtatttcatgggacaaaatctc
tgggaggacatcgtgaaaaatgcagagtatgatgagttgtttagactaatgaacacatg
tggtcgtctccagaatgatattcaaagctttgagagggaatgcaaggatggcaaactga
acagtgtgtcactgcttgttcttgacagcaaagatgtcatgtcagtagaagaggctaaa
gaggcgataaacgagtctatatcatcatgtagaagagagttgctacggttggttgttag
agaagacggtgtcattcctaaatcatgcaaggagatgttctggaatctttacaagacaa
gccatgtgttctactctcaggccgatggattttcctcgccgaaggaaatgatgggtgct
atgaatggagtaatctttgagccactgaaaactagaggcaactag
```

Fig.12B

IDENTIFICATION OF SYN-COPALYL DIPHOSPHATE SYNTHASE

CROSS-REFERENCE TO RELATED APPLICATION

The present invention claims priority to U.S. Provisional Application Ser. No. 60/573,472, filed May 21, 2004 the disclosure of which is expressly incorporated by reference.

GRANT REFERENCE CLAUSE

This invention was funded at least in part by USDA/CSREES 2005-35318-15477. The government may own certain rights in this invention.

BACKGROUND OF THE INVENTION

Plants produce a vast and diverse array of low-molecular-weight organic compounds. A small number of these are primary metabolites, which are common to all plant species as they are directly required for growth and development. The remaining, overwhelming majority of these natural products are considered secondary metabolites and are not found in all plants. Thus, individual species produce a limited subset of all plant natural products, although families will sometimes share common secondary metabolism (e.g., oleoresinosis in Pinaceae). Nevertheless, many secondary metabolites have important ecological roles, particularly in plant defense. (Croteau et al. 2000). For example, phytoalexins are produced in response to microbial infections and exhibit antimicrobial properties (VanEtten et al. 1994), while allelochemicals are secreted to the rhizosphere, and suppress germination and growth of neighboring seeds (Bais et al. 2004).

Particularly abundant in plants, as both primary and secondary metabolites, are terpenoids, which comprise the largest class of natural products and exhibit wide diversity in chemical structure and biological function (Croteau et al. 2000). Much of the structural variation within this class arises from the diverse carbon backbones formed by terpene synthases (cyclases). These divalent metal ion dependent enzymes carry out complex electrophilic cyclizations and/or rearrangements to create these diverse skeletal structures from relatively simple acyclic precursors (Davis and Croteau 2000). Notably, production of a specific backbone structure either dictates, or at least severely restricts, the metabolic fate of that particular molecule. Thus, terpenoid biosynthesis is often controlled, at least in part, by regulating terpene synthase activity [e.g. giberellin biosynthesis; (Silverstone et al. 1997)].

A substantial fraction of the known terpenoids can be classified as labdane-related diterpenoids (20 carbon). These are defined here as minimally containing the bicyclic hydrocarbon structure found in the labdane class of diterpenoids, although this core structure can be further cyclized and rearranged, as in the related/derived structural classes (e.g., kauranes, abietanes, and [iso]pimaranes). Significantly, this includes the primary metabolite gibberellin growth hormones. However, the vast majority of the more than 5,000 known labdane-related diterpenoids are secondary metabolites.

Biosynthesis of labdane-related diterpenoids is initiated by class II terpene synthases which catalyze formation of the characteristic bicyclic backbone in producing specific stereoisomers of labdadienyl/copalyl disphosphate (CPP) from the universal diterpenoid precursor, and plant primary metabolite, (E,E,E)-geranylgeranyl diphosphonate (GGPP). In addition, this core bicyclic structure is always further modified by stereoselective CPP specific class I terpene synthases (i.e. ionization of the diphosphate moiety to form one or more new carbon-carbon bonds). Thus, class II and class I terpene synthases act sequentially in catalyzing stereochemically coupled cyclization reactions to form labdane-related diterpene skeletal backbones.

Significantly, the class II protonation-initiated bicyclization reaction is fundamentally different than the diphosphate ionization initiated reactions catalyzed by the more common class I terpene synthases. Nevertheless, the class II cyclases clearly fall within the terpene synthase gene family (Bohlmann et al. 1998b). However, rather than the DDXXD metal binding motif functionally associated with class I activity (Davis and Croteau 2000), class II terpene cyclases contain a distinct DXDD motif (Sun and Kamiya 1994) which has been functionally associated with class II cyclization reactions (Peters et al. 2001).

Prototypical plant class I terpene synthases are similar in size and contain two structurally defined domains (Starks et al. 1997; Whittington et al. 2002). However, some terpene synthases, and in particular all of those involved in labdane-related diterpenoid biosynthesis, contain a large amount of additional amino terminal sequence termed the 'insertional' element [approximately 240 amino acid residues; (Peters and Croteau 2002)]. Notably, given adequate sequence information, this specific structural feature is useful for putative identification of labdane-related diterpene synthases, although it is not sufficient for even such generalized functional annotation [e.g. (Bohlmann et al. 1998a)].

Rice (*Oryza sativa*) provides a model system to investigate labdane-related diterpenoid biosynthesis, as this well characterized plant is known to produce a number of such natural products beyond the ubiquitous gibberellic acid (GA) growth hormones (FIG. 1). These compounds include momilactones A and B (Kato et al. 1973; Cartwright et al. 1981), oryzalexins A to F (Akatsuka et al. 1985; Sekido et al. 1986; Kato et al. 1993; 1994), oryzalexin S (Kodama et al. 1992), and phytocassanes A to E (Koga et al. 1995; Koga et al. 1997). All of these natural products are produced in leaves in response to infection with the blast pathogenic fungus *Magneportha grisea* and exhibit antimicrobial properties; thus qualifying as phytoalexins (VanEtten et al. 1994). In addition, momilactones A and B also act as allelochemicals, as these were originally identified as dormancy factors from rice seed husks (Kato et al. 1973), and momilactone B has recently been shown to be constitutively secreted from the roots of rice seedlings, where it acts as an allelopathic agent (Kato-Noguchi and Ino 2003). Further, secretion of antimicrobial agents to the rhizosphere may also provide a competitive advantage for root establishment through local suppression of soil micro-organisms (Bais et al. 2004).

Conveniently, rice leaves produce all of these secondary metabolites after UV irradiation as well as blast fungal infection (Kodama et al. 1988), providing a standard method for inducing biosynthesis of these natural products and, presumably, transcription of the corresponding enzymatic machinery. In particular, it has previously been shown that UV irradiation induces biosynthesis of ent-sandaracopimaradiene, syn-pimara-7,15-diene, and syn-stemar-13-ene, the putative precursors to oryzalexins A to F, momilactones A and B, and oryzalexin S, respectively (Wickham and West 1992). These polycyclic diterpene hydrocarbons further have been demonstrated to be selectively produced via CPP of the corresponding stereochemistry [i.e. ent or syn; (Mohan et al. 1996)]. More recent work has identified the class I diterpene synthase producing ent-cassa-12,15-diene, the putative precursor to phytocassanes A to E (Yajima et al. 2004), stereoselectively from ent-CPP (Cho et al. 2004). In addition, it was also recently reported that only a single CPP synthase gene (OsCPS1) is involved in GA biosynthesis, although no sequence information was presented (Sakamoto et al. 2004). Thus, gene function was demonstrated by the severe growth defect (i.e. dwarf phenotype) of the corresponding mutant (i.e. T-DNA insertion) plant, along with its rescue by exogenous application of $GA_3$. Finally, although other putative class II and class I labdane-related diterpene synthase genes can be found in the rice genome, gene isolation and biochemical characterization have not been previously reported, leaving in question the role and specific activity of these additional cyclases.

It is therefore a primary objective of the present invention to identify, isolate and purify nucleic acid fragments encoding class II terpene synthases.

It is a further objective of the present invention to identify, isolate, and purify a nucleic acid fragment encoding a syn-copalyl diphosphate synthase.

It is still a further objective of the present invention to identify, isolate, and purify a nucleic acid fragment encoding a syn-copalyl diphosphate specific 9β-pimara-7,15-diene synthase.

It is a further objective of the present invention to identify, isolate, and purify a nucleic acid fragment encoding ent-copalyl diphosphate synthases.

It is a further objective of the present invention to provide a method of modulating terpenoid biosynthesis.

It is a further objective of the present invention to provide a method of modulating expression of class II terpene synthases.

It is yet a further objective of the present invention to provide a method of modulating expression of a syn-copalyl disphosphate.

It is a further objective of the present invention to provide a method of modulating expression of syn-copalyl diphosphate specific pimara-7,15-diene synthase.

It is a further objective of the present invention to provide a method of modulating expression of ent-copalyl diphosphate synthases.

The method and means of accomplishing each of the above objectives as well as others will become apparent from the detailed description of the invention which follows hereafter.

SUMMARY OF THE INVENTION

The present invention relates to the functional identification of three class II labdane-related diterpene cyclases; a syn-CPP synthase, namely $OsCPS4_{syn}$, along with two disparate ent-CPP synthases, namely $OsCPS1_{ent}$ and $OsCPS2_{ent}$. $OsCPS4_{syn}$ is involved in the production of defensive natural products (i.e. phytoalexins/allelochemicals; FIG. 1). Accordingly, $OsCPS4_{syn}$ mRNA is specifically induced in leaves prior to production of the corresponding phytoalexins. Thus, transcriptional control of $OsCPS4_{syn}$ appears to be an important means of controlling biosynthesis of syn-copalyl diphosphate derived phytochemicals. $OsCPS1_{ent}$ has been found to normally operate in GA biosynthesis as mutations in this gene result in severely impaired growth. Further, $OsCPS2_{ent}$ is involved in related secondary metabolism producing defensive natural products. In particular, $OsCPS2_{ent}$ mRNA is specifically induced in leaves prior to the production of the corresponding phytoalexins. Thus, transcriptional control of $OsCPS2_{ent}$ also appears to be an important means of regulating the production of the corresponding ent-copalyl diphosphate derived defensive phytochemicals.

The invention further relates to the identification of the syn-CPP specific class I labdane-related 9β-pimara-7,15-diene diterpene synthase, namely OsDTS2. OsDTS2 is involved in the production of the phytoalexins/allelochemicals momilactones A and B. Accordingly, OsDTS2 mRNA is also specific induced in leaves prior to the production of the corresponding natural products. Thus, transcriptional control of OsDTS2 appears to be an important means of specifically controlling biosynthesis of the momilactones and any other 9β-pimara-7,15-diene derived natural products.

In accordance with this invention, $OsCPS1_{ent}$, $OsCPS2_{ent}$, $OsCPS4_{syn}$, and OsDTS2 have been identified, sequenced, isolated, and biochemically characterized. The isolation and functional identification of these labdane-related diterpene synthases provides a means of modifying enzymes and metabolic pathways for the production of targeted libraries and specific individual terpenoid products.

BRIEF DESCRIPTION OF THE DRAWINGS

FIG. 2 shows the amino acid alignment of class II terpene synthases from the cereal/grass family of plants (Poaceae): $ZmCPS1_{ent}$ (SEQ ID NO:1), $OsCPS1_{ent}$ (SEQ ID NO:2), $OsCPS2_{ent}$ (SEQ ID NO:3), and $OsCPS4_{syn}$ (SEQ ID NO:4). Truncations for recombinant pseudomature constructs are indicated by the arrowhead and the (D,E)XD(D,N) motif by an underline.

FIGS. 9A-9B illustrate the amino acid (SEQ ID NO:2) and nucleotide sequence (SEQ ID NO:9) listings for OsCPS1$_{ent}$.

FIGS. 10A-10D illustrate the amino acid (SEQ ID NO:3) and nucleotide sequence (SEQ ID NOS:10-12) listings for OsCPS2$_{ent}$.

FIGS. 11A-11D illustrate the amino acid (SEQ ID NO:4) and nucleotide sequence (SEQ ID NO:13-15) listings for OsCPS4$_{syn}$.

FIGS. 12A-12B illustrate the amino acid (SEQ ID NO:8) and nucleotide sequence (SEQ ID NO:16) listings for OsDTS2.

DETAILED DESCRIPTION OF THE INVENTION

Figure 1:
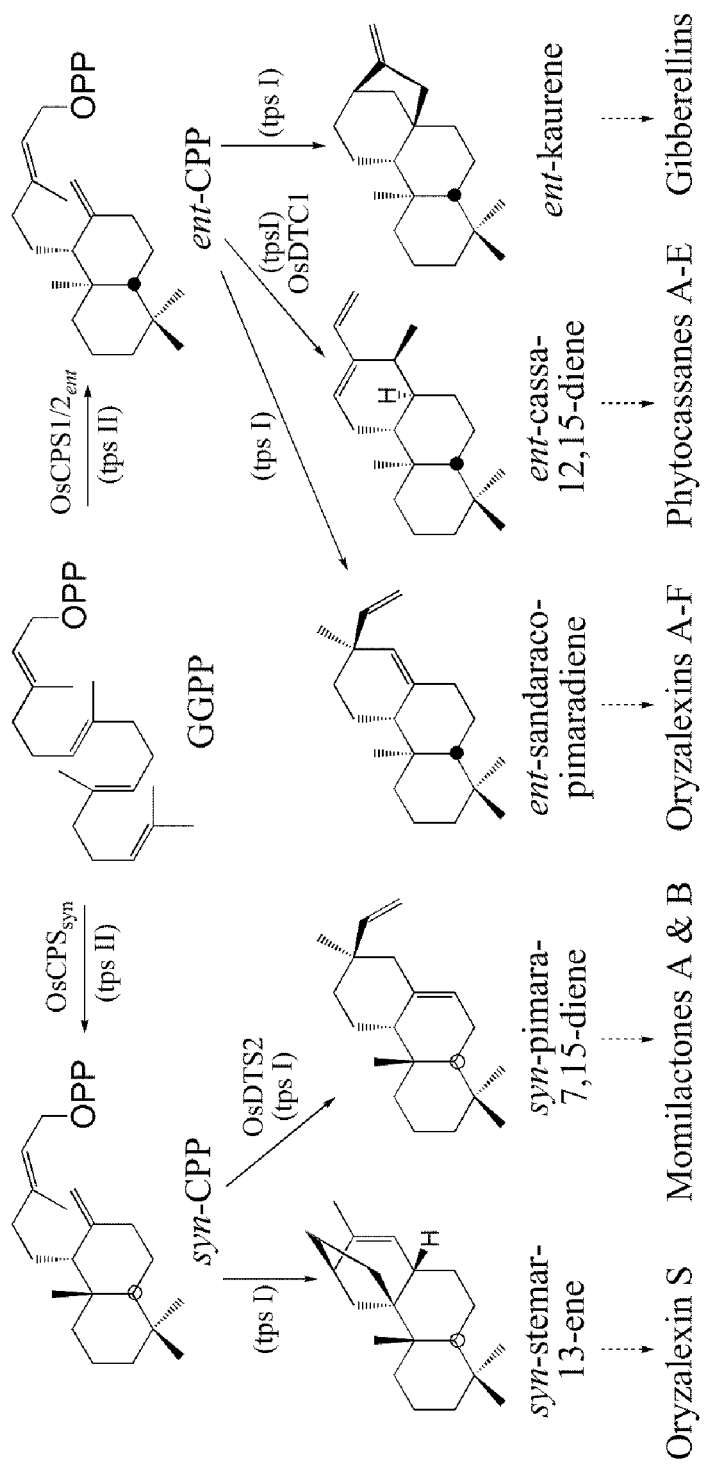
FIG. 1 shows the known cyclization steps in rice labdane-related diterpenoid biosynthesis. Reactions catalyzed by class II (tpsII) or class I (tpsI) terpene synthases are indicated, along with the families of natural products derived from each of the named polycyclic hydrocarbon structures (dashed arrows indicate multiple enzymatic steps).

The present invention describes the labdane-related diterpene synthases OsCPS1$_{ent}$, OsCPS2$_{ent}$, OsCPS4$_{syn}$, and OsDTS2. The inventors have determined that while OsCPS1$_{ent}$ is responsible for GA biosynthesis, OsCPS2$_{ent}$, OsCPS4$_{syn}$, and OsDTS2 act in defensive secondary metabolism. Further, as expected for a role in initiating labdane-related diterpenoid biosynthesis, transcription of OsCPS2$_{ent}$, OsCPS4$_{syn}$, and OsDTS2 is induced by conditions that stimulate phytoalexins biosynthesis, indicating regulatory control points for these important metabolic processes.

Due to the inventors' interest in labdane-related diterpene synthases as potentially significant targets for metabolic engineering and biochemical analysis, they searched the extensive sequence information available for rice (Goff et al. 2002; Yu et al. 2002; Kikuchi et al. 2003) and identified three putative class II diterpene cyclases and one putative labdane-related class I diterpene synthase. One of the class II enzymatic genes was readily amplified from mRNA prepared from UV-irradiated rice leaves, and its sequence deposited into the various nucleotide databases as accession AY530101. The second class II synthase gene was not as easily isolated. Nevertheless, the inventors were able to successfully clone the corresponding full-length cDNA and have deposited the associated sequence into the various nucleotide databases as accession AY602991. The third class II gene was available from the rice full-length cDNA sequencing project (accession AK100333; Kikuchi et al., 2003) and obtained from the Rice Genome Resource Center (www.rgrc.dna.affrc.go.jp). Notably, this last gene sequence contains EXDD in place of the otherwise conserved DXDD motif functionally associated with class II cyclization. This was confirmed by independently cloning a gene fragment covering this region. Finally, the putative class I labdane-related terpene synthase was also cloned from UV-irradiated leaves and the associated sequence deposited into the various nucleotide databases as accession AY616862.

For each of the class II genes, truncated versions were constructed for recombinant expression. (See FIG. 2, SEQ ID NOS:1-4). These were based on truncation analysis of the *Arabidopsis* CPS$_{ent}$. Enzymatic assays were carried out with partially purified recombinant preparations and GGPP as substrate. Phosphatase treatment was then employed to remove the pyrophosphate from GGPP and any enzymatically formed derivative to enable straightforward extraction of the resulting alcohol into organic solvent. Enzymatic conversion of GGPP was analyzed by gas chromatography-mass spectrometry (GC-MS) of the resulting extracts, demonstrating production of an altered prenyl diphosphate structure. Comparison of the enzymatically formed compounds to similarly dephosphorylated authentic samples of ent- and syn-CPP (FIGS. 3-5) demonstrated that the first class II enzyme (accession AY530101) produces syn-CPP (and so was named OsCPS4$_{syn}$), while the other two class II cyclases (accessions AK100333 and AY602991) both proved to produce ent-CPP (and so were named OsCPS1$_{ent}$ and OsCPS2$_{ent}$, respectively). The isolated class I gene was expressed as a glutathione-S-transferase (GST) fusion protein, purified, and assayed with GGPP, ent-CPP, or syn-CPP as substrate, followed by organic extraction and GC-MS analysis. Enzymatic conversion was only observed with syn-CPP, as no products were detected from incubations with GGPP or ent-CPP. Therefore, this is a labdane-related diterpene synthase and was named OsDTS2. Further, OsDTS2 is stereoselective and represents the first identified class I terpene synthase specific for syn-CPP. In addition, comparison with the known synthetic standards (Mohan et al. 1996) identified the OsDTS2 enzymatic product as 9β-pimara-7,15-diene.

The recent publication by Sakamoto et al. (2004) clearly demonstrated that only a single class II terpene cyclase, which they termed OsCPS1, is normally involved in GA metabolism. One of the two ent-CPP synthases identified herein corresponds to OsCPS1, specifically, the gene derived from the large-scale cDNA project (accession AK100033) that has been designated OsCPS1$_{ent}$ to more precisely reflect its function. Because the other functional ent-CPP synthase identified here (accession AY602991) does not compensate for mutations in OsCPS1$_{ent}$ and, therefore, is not expressed in conjunction with GA biosynthesis, the inventors hypothesized that this gene (designated OsCPS2$_{ent}$ as it corresponds to the OsCPS2 of Sakamoto et al., 2004) might be alternatively expressed for production of the known ent-labdane-related diterpenoid defensive secondary metabolites. Further, the syn-CPP synthase (which was designated OsCPS4$_{syn}$ as it corresponds to the OsCPS4 of Sakamoto et al., 2004), as well as the subsequently acting OsDTS2, must be involved in biosynthesis of defensive secondary metabolites as this is the function of all syn-labdane-related diterpenoids in rice (FIG. 1). The involvement of OsCPS2$_{ent}$, OsCPS4$_{syn}$, and OsDTS2 in defensive secondary metabolism was initially examined by characterization of gene transcription in response to methyl jasmonate (MeJA). Application of this important plant defense signaling molecule previously has been shown to induce phytoalexin biosynthesis in rice cell culture (Nojiri et al. 1996). While transcription of the GA-specific OsCPS1$_{ent}$ gene is not significantly altered, OsCPS2$_{ent}$, OsCPS4$_{syn}$, and OsDTS2 mRNA levels were consistently increased by MeJA treatment (FIGS. 6-8), thus indicating a role for these enzymes in defensive secondary metabolism.

Figure 6:
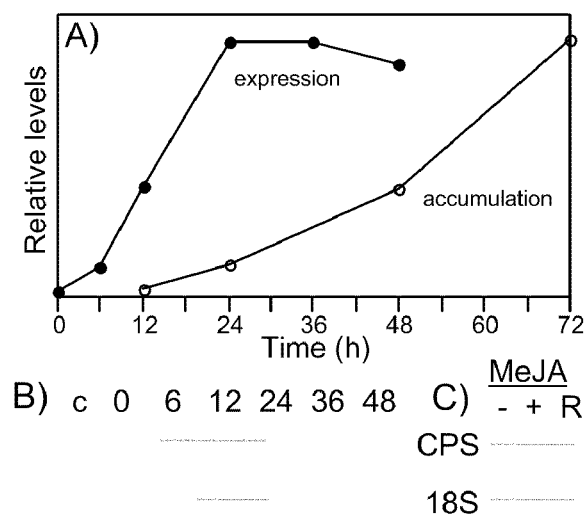
FIG. 6 shows expression analysis of $OsCPS4_{syn}$; A) Graphical comparison of $OsCPS_{syn}$ mRNA levels (closed circles) and phytoalexin accumulation [open circles; as described by (Kodama et al., 1988)], in UV-irradiated detached leaves. Quantitative RT-PCR analysis of $OsCPS_{syn}$ mRNA expression levels is shown in B) and C). Specific bands corresponding to the 18S rRNA internal control and $OsCPS_{syn}$ are indicated. B) Expression in response to UV-irradiation. Time (hours) after exposure is indicated (c=control leaves after ~18 hours). C) Expression in untreated four week old plant roots (R), or in germinated seedlings in response to application of 0.5 mM methyl jasmonate (+MeJA) or water control (-MeJA); II) $OsCPS1_{ent}$ and OsCPS2$_{ent}$: Semi-quantitative RT-PCR analysis of mRNA expression levels for the indicated genes. Specific bands corresponding to CPS or the 18S rRNA control are indicated.
Figure 7:
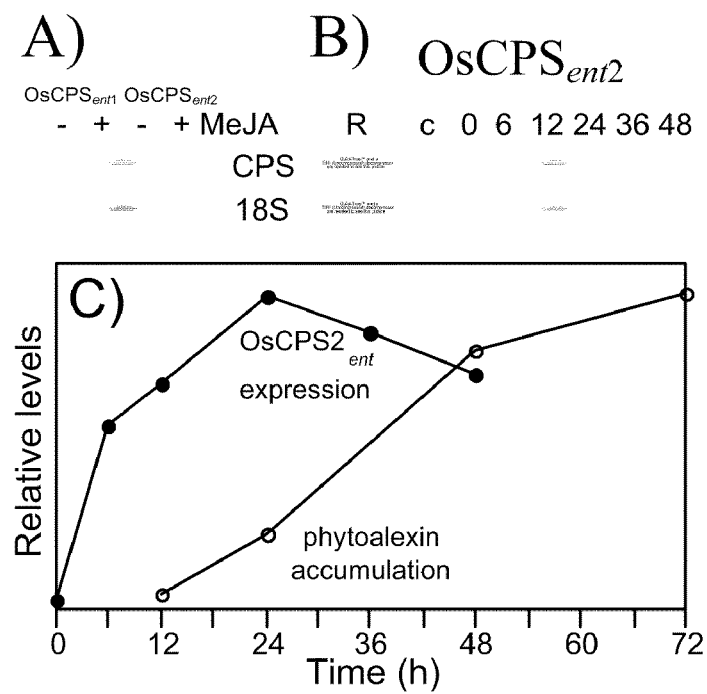
FIG. 7 shows expression analysis of OsCPS2$_{ent}$; A) Expression in germinated seedlings in response to application of 0.5 mM MeJA, B) Expression of OsCPS2$_{ent}$ in detached leaves from 4-week-old plants in response to UV irradiation. Time (hours) after exposure is indicated (c=control leaves after approximately 18 h), C) Relative graphical comparison of OsCPS2$_{ent}$ mRNA levels (black circles) and ent-labdane-related diterpenoid phytoalexins accumulation (white circles; as described by Kodama et al., 1988) in UV-irradiated detached leaves.
Figure 8:
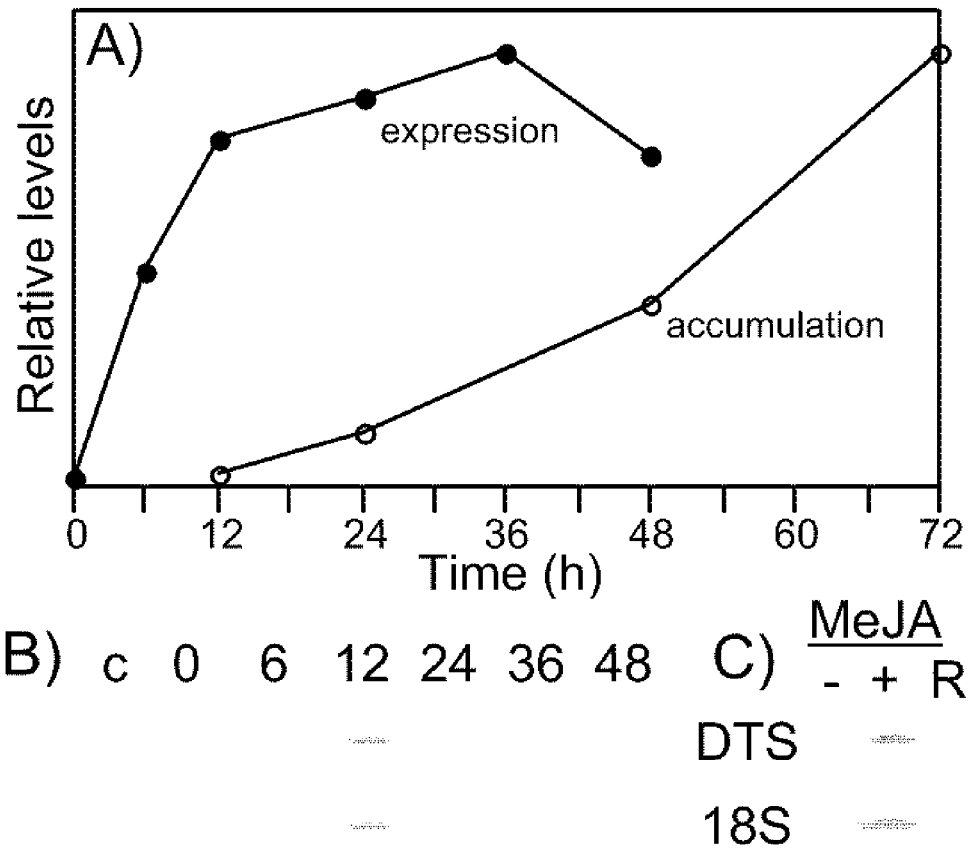
FIG. 8 shows expression analysis of OsDTS2: A) Graphical comparison of OsDTS2 mRNA levels (closed circles) and momilactone accumulation [open circles; as described by (Kodama et al., 1988)], in UV-irradiated detached leaves. Semi-quantitative RT-PCR analysis of OsDTS2 mRNA expression levels is shown in B) and C). Specific bands corresponding to the 18S rRNA control and OsDTS2 (DTS) are indicated. B) Expression in response to UV-irradiation. Time (hours) after exposure is indicated (c=control leaves after ~18 hours). C) Expression in untreated four-week old plant roots (R), or in germinated seedlings in response to application of 0.5 mM methyl jasmonate (+MeJA) or water control (-MeJA).

Previous review of the relevant literature has been used to suggest that plant secondary metabolism is most often regulated at the level of transcription (Peters and Croteau 2004). Transcriptional control is manifested by up-regulation of enzymatic mRNA levels, with subsequent phytochemical accumulation, in response to the appropriate environmental conditions. This was investigated through use of UV irradiation, which has long been appreciated to induce phytoalexin biosynthesis in rice (Cartwright et al. 1977). In addition, quantitative analysis of phytochemical accumulation for the detached leaf UV-irradiation method used here has previously been reported (Kodama et al. 1988). Consistent with the indicated role in phytoalexin biosynthesis, transcription of $OsCPS2_{ent}$, $OsCPS4_{syn}$ and OsDTS2 is dramatically increased by UV-irradiation prior to accumulation of the derived natural products (FIGS. 6-8). These results not only demonstrate that these enzymes are involved in defensive secondary metabolism, but further indicate that biosynthesis of the labdane-related diterpenoid phytoalexins also may be regulated, at least to some extent, through transcriptional control of the associated terpene synthases.

As used here, the term "isolated" means any class I or II terpene synthase of the present invention, or any gene encoding a class I or II terpene synthase, which is essentially free of other polypeptides or genes, respectively, or of other contaminants with which the class I or II terpene synthase polypeptide or gene might normally be found in nature.

The invention includes a functional polypeptide, $OsCPS1_{ent}$, $OsCPS2_{ent}$, $OsCPS_{syn}$, or OsDTS2 and functional fragments thereof. As used herein, the term "functional polypeptide" refers to a polypeptide which possesses a biological function or activity which is identified through a defined functional assay and which is associated with a particular biologic, morphologic, or phenotypic alteration in the cell. The biological function, for example, can vary from a polypeptide fragment as small as an epitope to which an antibody molecule can bind to a large polypeptide which is capable of participating in the characteristic induction or programming of phenotypic changes within a cell. A "functional polynucleotide" denotes a polynucleotide which encodes a functional polypeptide as described herein.

Minor modifications of the primary amino acid sequences of the terpene synthases of this invention may result in proteins which have substantially equivalent activity as compared to the polypeptides described herein. Such modifications may be deliberate, as by site-directed mutagenesis, or may be spontaneous. All of the polypeptides produced by these modifications are included herein as long as the described activities of the terpene synthases are present. Further, deletion of one or more amino acids can also result in a modification of the structure of the resultant molecule without significantly altering its biological activity. This can lead to the development of a smaller active molecule which would have broader utility. For example, it is possible to remove amino or carboxy terminal amino acids which may not be required for biological activity.

The polypeptides of the invention also include conservative variations of the polypeptide sequences. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention is also intended to include synthetic peptides. The amino acid sequences of SEQ ID NOS: 5-8 (FIGS. 9-12), and conservative variations, comprise the synthetic peptides of the invention. As used herein, the term "synthetic peptide" denotes a peptide which does not comprise an entire naturally occurring protein molecule. The peptide is "synthetic" in that it may be produced by human intervention using such techniques as chemical synthesis, recombinant genetic techniques, or fragmentation of whole antigen or the like.

Peptides of the invention can be synthesized by such commonly used methods as t-BOC or FMOC protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9). Peptides of the invention can also be synthesized by the well known solid phase peptide synthesis methods described in Merrifield, J. Am. Chem. Soc., 85:2149, 1962, and Stewart and Young, Solid Phase Peptides Synthesis, (Freeman, San Francisco, 1969, pp. 27-62), using a copoly (styrene-divinylbenzene) containing 0.1-1.0 mMol amines/g polymer. On completion of chemical synthesis, the peptides can be deprotected and cleaved from the polymer by treatment with liquid HF-10% anisole for about ¼-1 hours at 0° C. After evaporation of the reagents, the peptides are extracted from the polymer with 1% acetic acid solution which is then lyophilized to yield the crude material. This can normally be purified by such techniques as gel filtration on Sephadex G-15 using 5% acetic acid as a solvent. Lyophilization of appropriate fractions of the column will yield the homogeneous peptide or peptide derivatives, which can then be characterized by such standard techniques as amino acid analysis, thin layer chromatography, high performance liquid chromatography, ultraviolet absorption spectroscopy molar, rotation, solubility, and quantitated by the solid phase Edman degradation.

The invention also provides polynucleotides which encode the class I and II synthases of the invention and the synthetic peptides of SEQ ID NOS. 5-8 (FIGS. 9-12) and those sequences having substantial identity to the same. The nucleotide sequence of $OsCPS1_{ent}$ comprises the sequence found in SEQ ID NO. 9. (FIG. 9). The nucleotide sequence of $OsCPS2_{ent}$ comprises the sequences found in SEQ ID NOS. 10-12. (FIG. 10). The nucleotide sequence of $OsCPS4_{syn}$ comprises the sequences found in SEQ ID NOS. 13-15. (FIG. 11). The nucleotide sequence of OsDTS2 comprises the sequence found in SEQ ID NO. 16.

As used herein, "polynucleotide" refers to a polymer of deoxyribonucleotides or ribonucleotides, in the form of a separate fragment or as a component of a larger construct. As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 55-100%, preferably at least 55%, preferably at least 60%, more preferably at least 70%, 80%, 90%, and most preferably at least 95%.

DNA encoding the polypeptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. Preferably, the nucleotide sequences encoding the terpene synthases of this invention are the sequences of SEQ ID NOS.:9-16.

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; 2) antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucleic Acid Research, 9:879, 1981).

The development of specific DNA sequences encoding $OsCPS1_{ent}$, $OsCPS2_{ent}$, $OsCPS4_{syn}$, and OsDTS2 can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucl. Acid Res. 11:2325, 1983).

A cDNA expression library, such as lambda gt11, can be screened indirectly for polypeptides having at least one epitope, using antibodies specific for class II terpene synthases. Such antibodies can be either polyclonally or monoclonally derived and used to detect expression product indicative of the presence of terpene synthase cDNA.

A polynucleotide sequence can be deduced from the genetic code. However, the degeneracy of the code must be taken into account. Polynucleotides of the invention include sequences which are degenerate as a result of the genetic code. The polynucleotides of the invention include sequences that are degenerate as a result of the genetic code. There are 20 natural amino acids, most of which are specified by more than one codon. Therefore, as long as the amino acid sequences of the class II terpene synthases results in a functional polypeptide (at least, in the case of the sense polynucleotide strand), all degenerate nucleotide sequences are included in the invention.

The polynucleotide sequences for the terpene synthases of this invention also include sequences complementary to the polynucleotide encoding these terpene synthases (antisense sequences). Antisense nucleic acids are DNA or RNA molecules that are complementary to at least a portion of a specific mRNA molecule (Weintraub, Scientific American, 262: 40, 1990). The invention embraces all antisense polynucleotides capable of inhibiting production of terpene synthase polypeptides. In the cell, the antisense nucleic acids hybridize to the corresponding mRNA, forming a double-stranded molecule. The antisense nucleic acids interfere with the translation of the mRNA since the cell will not translate an mRNA that is double-stranded. Antisense oligomers of about 15 nucleotides are preferred, since they are easily synthesized and are less likely to cause problems than larger molecules when introduced into the target terpene synthase-producing cell. The use of antisense methods to inhibit the translation of genes is well known in the art (Marcus-Sakura, Anal. Biochem., 172:289, 1988).

In addition, ribozyme nucleotide sequences for $OsCPS1_{ent}$, $OsCPS2_{ent}$, $OsCPS4_{syn}$, and OsDTS2 are included in the invention. Ribozymes are RNA molecules possessing the ability to specifically cleave other single-stranded RNA in a manner analogous to DNA restriction endonucleases. Through the modification of nucleotide sequences which encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

The polypeptides of the invention can also be used to produce antibodies which are immunoreactive or bind to epitopes of the terpene synthase polypeptides. Antibodies of the invention also include antibodies which bind to the synthetic peptides in SEQ ID NOS.:5-8 (FIGS. 9-12). Antibodies which consist essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibodies which bind to the polypeptides of the invention can be prepared using an intact polypeptide or fragments containing small peptides of interest as the immunizing antigen. The polypeptides or peptides such as SEQ ID NOS.:5-8 can be derived from translated cDNA or chemical synthesis which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse, a rat, or a rabbit).

If desired, polyclonal or monoclonal antibodies can be further purified, for example, by binding to and elution from a matrix to which the polypeptide or a peptide to which the antibodies were raised is bound. Those skilled in the art will know of various techniques common in the immunology arts for purification and/or concentration of polygonal antibodies, as well as monoclonal antibodies (See for example, Coligan, et al., Unit 9, Current Protocols in Immunology, Wiley Interscience, 1991, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Polynucleotide sequences encoding the polypeptides (SEQ ID NOS.:5-8) of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the terpene synthase polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of markers typically used in prokaryotic expression vectors include antibiotic resistance genes for ampicillin (β-lactamases), tetracycline and chloramphenicol (chloramphenicol acetyl-transferase). Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XG-PRT, gpt).

Transformation of a host cell with recombinant DNA may be carried out by conventional techniques which are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, and CHO cells.

Isolation and purification of host cell expressed polypeptide, or fragments thereof, provided by the invention, may be carried out by conventional means including preparative chromatography and immunological separations involving monoclonal or polyclonal antibodies.

The class I and II terpene synthases of the invention are useful in a screening method for identifying compounds or compositions which affect the activity of the synthases. Thus, in another embodiment, the invention provides a method for identifying a composition which affects a class I or II terpene synthase of this invention comprising incubating the components, which include the composition to be tested and the synthase or a polynucleotide encoding the synthase, under conditions sufficient to allow the components to interact, then subsequently measuring the effect the composition has on synthase activity or on the polynucleotide encoding the synthase. The observed effect on the synthase may be either inhibitory or stimulatory. A polynucleotide encoding the kinase may be inserted into an expression vector and the effect of a composition on transcription of the kinase can be measured, for example, by Northern blot analysis.

Another embodiment provides a method for engineering production of syn-CPP or other molecules of the invention either ex vivo or in genetically-engineered organisms. In this respect, using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so. It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter, such as ubiquitin, to direct transcription, a ribosome binding site for translational initiation, and a transcription/translation terminator. Constitutive promoters are classified as providing for a range of constitutive expression. Thus, some are weak constitutive promoters, and others are strong constitutive promoters. Generally, by "weak promoter" is intended a promoter that drives expression of a coding sequence at a low level. By "low level" is intended at levels of about $1/10,000$ transcripts to about $1/100,000$ transcripts to about $1/500,000$ transcripts. Conversely, a "strong promoter" drives expression of a coding sequence at a "high level", or about $1/10$ transcripts to about $1/100$ transcripts to about $1/1,000$ transcripts.

One of skill would recognize that modifications could be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

In another embodiment, the invention provides a method of modulating GA phytohormone and/or defensive phytoalexin biosynthesis in plants comprising administering an amount of reagent effective in modulating synthase activity. The term "effective amount" means that amount of monoclonal antibody or antisense nucleotide, for example, which is used, is of sufficient quantity to modulate terpene synthase activity.

Treatment includes administration of a reagent which modulates terpene synthase activity. The term "modulate" envisions the suppression of expression of the synthase when it is over-expressed, or augmentation of terpene synthase expression when it is under-expressed. It also envisions suppression of terpene synthase activity, for example, by using a competitive inhibitor of the natural synthase binding site in a cell. When a disorder is associated with synthase overexpression, such suppressive reagents as antisense polynucleotide sequences or binding antibodies can be introduced to a cell or plant. In addition, an anti-idiotype antibody which binds to a monoclonal antibody which binds a peptide of the invention may also be used in the therapeutic method of the invention. Alternatively, when a cell proliferative disorder is associated with underexpression or expression of a mutant polypeptide, a sense polynucleotide sequence (the DNA coding strand) or polypeptide can be introduced into the cell.

Peptides, antibodies, and polynucleotide sequences, including antisense sequences, can be therapeutically administered by various techniques known to those of skill in the art. Such therapy would achieve its therapeutic effect by introduction of the polynucleotide, into cells of plants having the proliferative disorder. Delivery of polynucleotide can be achieved using free polynucleotide or a recombinant expression vector such as a chimeric virus or a colloidal dispersion system. Especially preferred for therapeutic delivery of nucleotide sequences is the use of targeted liposomes.

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. By inserting a terpene synthase sequence into the viral vector, along with another gene which encodes the ligand for a receptor on a specific target cell, for example, the vector is now target specific. Retroviral vectors can be made target specific by inserting, for example, a polynucleotide encoding a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome to allow target specific delivery of the retroviral vector containing the polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsitation. Helper cell lines which have deletions of the packaging signal include but are not limited to psi2, PA317 and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced. The vector virions produced by this method can then be used to infect a tissue cell line, such as NIH 3T3 cells, to produce large quantities of chimeric retroviral virions.

Another targeted delivery system for polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. A preferred colloidal system of this invention is a liposome. Liposomes are artificial membrane vesicles which are useful as delivery vehicles in vitro and in vivo. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley, et al., Trends Biochem. Sci., 6:77, 1981). In addition to plant cells, liposomes have been used for delivery of polynucleotides in animal, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino, et al., Biotechniques, 6:682, 1988).

The invention also provides a method for detecting a cell with terpene synthase activity or a cell proliferative disorder associated with terpenoids comprising contacting a cell component with terpene synthase activity with a reagent which binds to the component and measuring the interaction of the reagent with the component. Such reagents can be used to measure relative levels of terpenoid expression compared to normal tissue. The cell component can be nucleic acid, such as DNA or RNA, or protein. When the component is nucleic acid, the reagent is a nucleic acid probe or PCR primer. The interaction of a nucleic acid reagent with a nucleic acid encoding a polypeptide with terpene synthase activity is typically measured using radioactive labels, however, other types of labels will be known to those of skill in the art. When the cell component is protein, the reagent is typically an antibody probe. The probes are directly or indirectly detectably labeled, for example, with a radioisotope, a fluorescent compound, a bioluminescent compound, a chemiluminescent compound, a metal chelator or an enzyme. Those of ordinary skill in the art will know of other suitable labels for binding to the antibody, or will be able to ascertain such, using routine experimentation.

The materials of the invention are ideally suited for the preparation of a kit. The kit is useful for the detection of the level of a terpene synthase comprising an antibody which binds a terpene synthase or a nucleic acid probe which hybridizes to terpenoid nucleotide, the kit comprising a carrier means being compartmentalized to receive in close confinement therein one or more containers such as vials, tubes, and the like, each of the container means comprising one of the separate elements to be used in the assay. For example, one of the container means may comprise a monoclonal antibody of the invention which is, or can be, detectably labeled. The kit may also have containers containing buffer(s) and/or a container comprising a reporter-means (for example, a biotinbinding protein, such as avidin or streptavidin) bound to a reporter molecule (for example, an enzymatic or fluorescent label).

The following examples are offered to illustrate but not limit the invention. Thus, they are presented with the understanding that various modifications may be made and still be within the spirit of the invention.

EXAMPLE 1

Functional Identification of Rice syn-Copalyl Diphosphate Synthase

Chemicals. The preparation of (E,E,E)-geranylgeranyl diphosphate (GGPP), and ent- and syn-copalyl diphosphate (CPP), from the corresponding copalol stereoisomers (Yee and Coates 1992), has been previously described (Mohan et al. 1996). Unless otherwise noted, all other chemicals were purchased from Fisher Scientific (Fairlawn, N.J., USA).

Plant material. Rice plants (*Oryza sativa* L. ssp. *indica* cv. IR24) were cultivated from seed under standard greenhouse conditions. After four weeks the plants were harvested for analysis. Detached leaves were UV-irradiated for 25 min. using a Spectroline UV lamp (set to emit at 254 nm wavelength) suspended 15 cm above the leaf surfaces, then incubated 18 hours at 30° C. with high humidity in the dark. These tissues were frozen by liquid $N_2$ and total RNA extracted using Concert Plant Reagent, following the manufacturers instructions (Invitrogen; Carlsbad, Calif., USA), and stored at −80° C. Where indicated, purification of mRNA was performed with Dynabeads Oligo$(dT)_{25}$, again following the recommended procedure (Dynal Biotech, Oslo, Norway) and also stored at −80° C.

Isolation of cDNA. Three putative class II terpene synthases were identified by BLAST queries of the rice genomic and cDNA databases with the nucleotide sequence of ent-CPP synthase from *Arabidopsis* (Sun and Kamiya 1994), with manual screening for the presence of the DXDD motif and 'insertional' element. RT-PCR reactions were performed to generate 5' fragments of the corresponding open reading frames, which exhibit limited homology to each other in this region (<55% nucleotide identity). However, for only one of these genes was it possible to amplify this region (efforts are underway to clone the remaining two sequences using differentiated internal sequences). The obtained 5' terminal fragment (599 bp) was cloned into pCR-Blunt II-TOPO (Invitrogen) and sequenced to verify its identity. To amplify the corresponding (partial) cDNA it was necessary to perform a 3' RACE reaction, which was done following the recommended protocol for the utilized GeneRacer kit (Invitrogen) and using the forward primer from the original 5' fragment isolation. This was also cloned into pCR-Blunt II-TOPO and verified by sequencing. The corresponding (partial) open reading frame was then sub-cloned, by PCR amplification for directional topoisomerization, into pENTR/SD/D-TOPO (Invitrogen). This was again verified by complete sequencing, demonstrating ~99% identity to the expected coding sequence (nucleotide sequence database accession number AK100631). Presumably the few observed differences reflect the intersubspecies variation between the ssp. *japonica* used by Kikuchi, et al (2003) and the ssp. *indica* used here. The true full-length cDNA was then identified through a 5' RACE reaction, using the reverse primer from the original 5' fragment isolation. Identical sequence was found in the 599 bp overlap between the originally cloned partial cDNA and the 5' RACE product. The full-length open reading frame was simply defined as running from the first occurrence of ATG to an in-frame stop codon (a total of 2304 bp). 3' RACE was again used to clone the open reading frame and 3' untranslated region into pCR-Blunt II-TOPO. The full-length open reading frame was then also sub-cloned into pENTR/SD/D-TOPO and the resulting construct verified by complete sequencing. This was then transferred, by directional recombination into the pDEST14 and pDEST15 expression vectors, while the partial cDNA was transferred into pDEST14 only (Gateway Technology, Invitrogen).

Recombinant expression and preparation. Expression was carried out with the BL21 derived strain C41 (Miroux and Walker 1996), using freshly transformed cells. Initial 1 mL NZY (1% NZ amine, 1% NaCl, 0.5% yeast extract, 0.2% $MgSO_4$) cultures, with 50 µg/1 mL ampicillin, were inoculated from 3-5 colonies to average over previously observed variations in expression level from single colony inoculation. The initial cultures were grown overnight (200 rpm at 37° C.) to saturation and 0.5 mL used to inoculate 50 mL NZY cultures, with 50 µg/mL ampicillin. These expression cultures were grown to $A_{600}$~0.6, transferred to 16° C. (200 rpm) for 1-2 hrs prior to induction with 1 mM IPTG, then incubated a further 16-20 hrs. The cells were harvested by centrifugation (4000 g, 20 min, 4° C.), re-suspended in 1 mL of lysis buffer (50 mM Bis-Tris, pH 6.8, 150 mM KCl, 10 mM $MgCl_2$, 1 mM DTT) and lysed by mild sonication on ice (Branson sonifier 450:10 s, continuous, output, setting 5). The resulting lysates were cleared by centrifugation (15,000 g, 30 min, 4° C.) and filtration (0.45µ) to yield soluble extracts. The recombinant protein was then partially purified as previously described (Peters et al. 2003). Briefly, the soluble extract was adsorbed to 0.2 mL ceramic hydroxyapatite type II beads (Bio-Rad; Hercules, Calif., USA), which was washed 4 times with 1 mL buffer (50 mM Bis-Tris, pH 6.8) to remove unbound material. Recombinant terpene synthase was then eluted with 0.5 mL of 200 mM sodium phosphate (pH 6.8), glycerol added to 10% (v/v), DTT to 5 mM, and the resulting solution spin filtered (0.2µ).

Enzymatic assay and analysis. Enzymatic analysis was carried out in assay buffer (50 mM HEPES, pH 7.2, 100 mM KCl, 7.5 mM $MgCl_2$, 5% glycerol, and 5 mM DTT), with 25 µL of recombinant soluble extract, and initiated by the addition of GGPP to 200 µM for a final volume of 0.2 mL. Reactions were incubated for 1 hour in the dark at room temperature and then extracted 3 times with 0.5 mL of hexanes. Residual organic solvent was removed by evaporation under $N_2$ to enable enzymatic dephosphorylation by calf intestinal phosphatase (10 U; New England Biolabs; Beverly, Mass., USA), which was allowed to proceed ~4 hrs at 37° C., largely as described (Wise et al. 2001). Similar dephosphorylation was carried out with authentic ent- and syn-CPP. The dephosphorylated compounds were then extracted 2 times with 0.5 mL of hexanes. All extracts were completely dried under $N_2$ and then resuspended in 100 µL of hexanes for GC-MS analysis. GC-MS was performed using an HP-1 column on an Agilent (Palo Alto, Calif., USA) 6890N GC instrument with 5973N mass selective detector. Samples (5 µL) were injected at 40° C. in the splitless mode. After a 3 min isothermal hold at 40° C., the temperature was increased at 20° C./min to 300° C., where it was held for an additional 4 min. MS data from 40 to 500 m/z were collected during the temperature ramp and high isothermal hold.

Expression analysis. $OsCPS4_{syn}$ mRNA transcription in response to UV-irradiation was measured using ssp. *japonica* rice, also grown from seed for four weeks under standard greenhouse conditions. Roots were directly harvested, while detached leaves either underwent the UV-irradiation treatment described above (Plant material), or the same procedure without exposure to UV-irradiation (control leaves). At the indicated times leaves were frozen in liquid $N_2$ and stored at −80° C. prior to RNA extraction. Transcription in response to methyl jasmonate was measured in ssp. *indica* seedlings. Seeds were sterilized for 2-3 hours in 10% bleach, rinsed 5 times in sterile water, then germinated in Petri dishes on 3 layers of filter paper moistened with 3 mL sterile water (this was maintained by the addition of 1 mL of sterile water every other day) at 30° C. in the dark for a week. Methyl jasmonate treatment was based on previous reports (Farmer and Ryan 1990; Martin et al. 2002). Briefly, one plate (seven seedlings) was then sprayed with 2 mL 0.5 mM (±)-methyl jasmonate (Bedoukian Research; Danbury, Conn., USA) in carrier solution (0.1% Tween 20 in sterile deionized water), while another (control plate) was only treated with 2 mL of the carrier. These plates were then incubated in separate air-tight containers for 48 hours, also at 30° C. in the dark, prior to RNA extraction from the whole seedlings. Quantitative RT-PCR was performed on 0.5 µg total RNA (isolated as described above) from each of the indicated tissues, using $OsCPS_{syn}$ specific primers (from the 5' fragment isolation) or QuantumRNA 18S standard primers (Ambion; Austin, Tex., USA). Appropriate preliminary studies were performed to ensure that the final amplification conditions were in the linear response range. RT-PCR reaction products were separated on a 2.5% agarose gel, stained with ethidium bromide, visualized over a UV-light source, and quantified (where indicated and with normalization against the 18S standard) with NIH Image software. Notably, the preliminary results with the other two putative rice class II terpene synthases indicate that these each exhibit a different expression pattern than $OsCPS_{syn}$ (i.e., one is non-inducible while the other is inducible but not expressed in roots).

Sequence analysis/alignments. Sequence alignments and identity/similarity comparisons were performed with the AlignX program in the Vector NTI software package (Invitrogen), using standard parameters. $OsCPS_{syn}$ was the reference sequence in all cases. $CPS_{ent}$ sequences were those from *Arabidopsis thaliana* (Sun and Kamiya 1994), *Zea maize* (Bensen et al. 1995), *Pisum sativum* (Ait-Ali et al. 1997), *Curcurbita maxima* (Smith et al. 1998), *Lycopersicon esclentum* (Rebers et al. 1999), and *Stevia rebaudiana* (Richman et al. 1999). Bifunctional class II/I sequences for abietane synthases were those from *Abies grandis* (Stofer Vogel et al. 1996) and *Ginkgo biloba* (Schepmann et al. 2001). Kaurene synthase sequences were those from *Curcurbita maxima* (Yamaguchi et al. 1996), *Arabidopsis thaliana* (Yamaguchi et al. 1998), and *Stevia rebaudiana* (Richman et al. 1999). Other strictly class I sequences included in sequence comparisons were specifically those containing 'insertional' elements; linalool synthase from *Clarkia breweri* (Dudareva et al. 1996), taxadiene synthase from *Taxus brevifolia* (Wildung and Croteau 1996), and bisabolene synthase from *Abies grandis* (Bohlmann et al. 1998a). Domain level comparisons were carried out by manually trimming the relevant sequences based on whole sequence alignment with abietadiene synthase from grand fir, for which approximate domain boundaries have been defined (Peters et al. 2003).

Results

Isolation of a class II terpene synthase cDNA from UV-irradiated rice leaves. Interest in the functionally distinct class II terpene synthases as potentially significant targets for metabolic engineering and biochemical analysis motivated this work to identify the syn-CPP synthase that has been previously implicated in rice phytoalexin/allelopathic natural product biosynthesis. The extensive genomic (Goff et al., 2002; Yu et al., 2002) and full-length cDNA (Kikuchi et al., 2003) sequence information available for rice was used to identify a number of putative class II terpene synthases, as defined by the presence of a DXDD motif and "insertional" element. One of these, originally identified from the rice large-scale full-length cDNA project (Kikuchi et al., 2003), was readily amplified from mRNA prepared from UV-irradiated rice leaves. The reported open reading frame was cloned into pENTR/SD/D-TOPO (Invitrogen) and verified by complete sequencing. However, alignment of the corresponding amino acid sequence with other diterpene synthases indicated the absence of the usual substantial N-terminal transit peptide required for the plastidal location of diterpene synthases in plants. The presence of additional N-terminal coding sequence was verified by 5' rapid amplification of cDNA ends (RACE), using the Invitrogen Gene Racer kit to ensure the selective amplification of full length (5' capped) mRNA. Identical sequence was found in the 599 bp overlap between the originally cloned partial cDNA and the 5' RACE product. The additional N-terminal coding sequence (corresponding to 46 amino acid residues) clearly forms at least part of the transit peptide, with an alkaline pH of 11.9, relative to the overall pH of 5.5, which is a common feature of plastid targeting sequences (Keegstra et al. 1989). Thus, a full-length cDNA sequence was determined, and has been deposited into the various nucleotide sequence databases as accession number AY530101. The full-length open reading frame was then amplified, cloned, and verified as described above for the partial cDNA.

Figure 3:
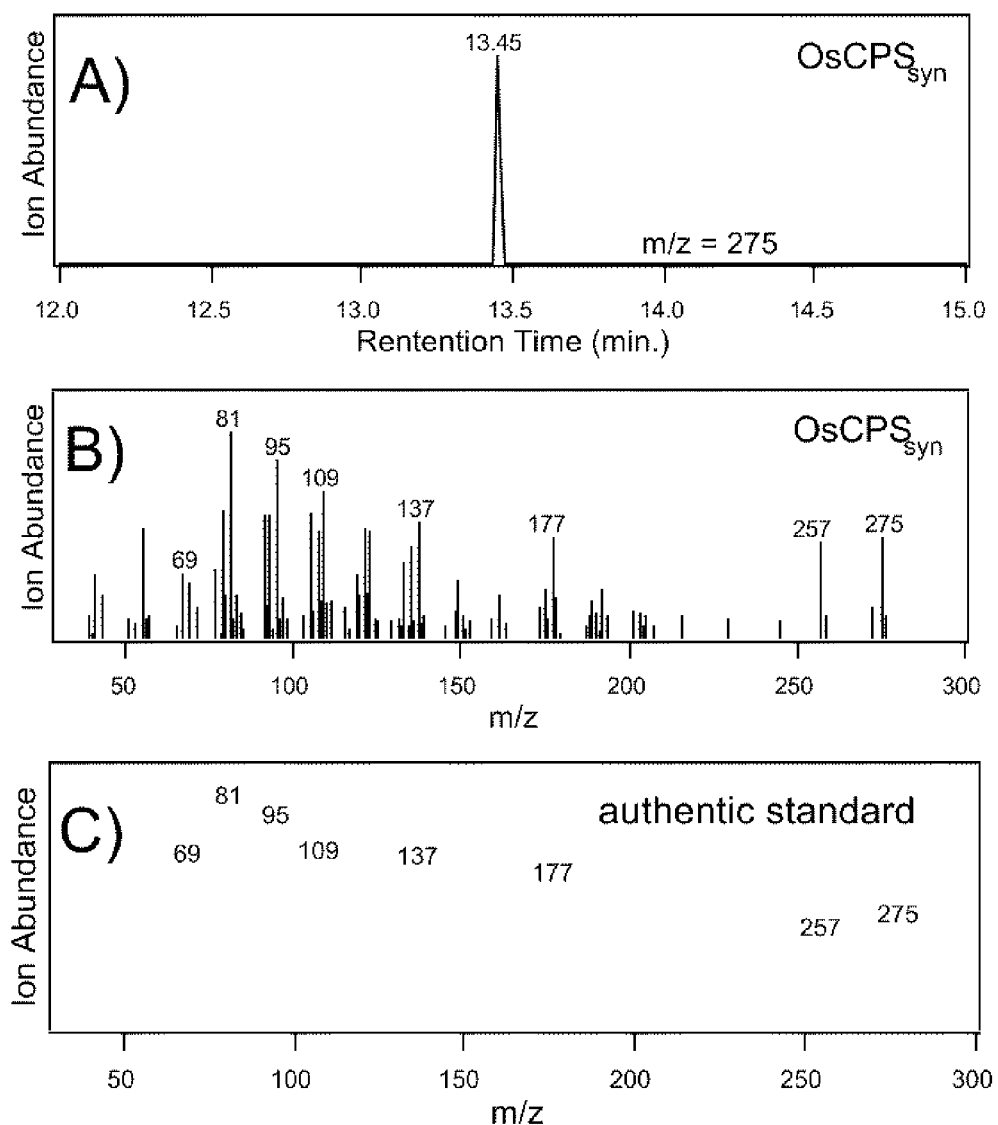
FIG. 3 shows identification of enzymatic products for $OsCPS4_{syn}$: A) GC-MS analysis (275 m/z extracted ion chromatographs) of the dephosphorylated reaction product from GGPP, B) Mass spectrum of the enzymatic GC-MS 275 m/z chromatograph peak (RT=13.45 min.), C) Mass spectrum of authentic dephosphorylated syn-CPP (i.e. syn-copalol), which also exhibits RT=13.45 min.

Functional expression and characterization demonstrated the specific production of copalyl diphosphate. Full-length class II terpene synthase preprotein (tpsII) was transferred, by recombination of the coding sequence, from pENTR to both pDEST14 and pDEST15 (Invitrogen Gateway system), for expression either alone or as a C-terminal fusion to glutathione S-transferase (GST-tpsII), respectively. The partial cDNA sequence, which presumably resembles the mature native protein, was transferred to pDEST14 for expression as a potential pseudomature protein. The resulting constructs were expressed in $E.$ $coli$ and recombinant soluble extracts prepared. Enzymatic assays with these preparations were carried out with GGPP as substrate. After the reaction was allowed to proceed for 1 hr at room temperature the solution was extensively extracted with organic solvent to remove any relatively non-polar compounds (i.e., hydrocarbon or alcohol formed from GGPP). Phosphatase treatment was then employed to remove the diphosphate from GGPP or any enzymatically formed derivative to allow straightforward extraction of the resulting alcohol into organic solvent. Enzymatic turnover of GGPP was analyzed by gas chromatography-mass spectrometry (GC-MS) of the resulting extracts. No hydrocarbons or alcohols were produced by any construct. However, conversion of GGPP into an altered prenyl diphosphate structure was detected, although only with the pseudomature construct. The lack of activity with the full-length preprotein provides an extreme example of the previously observed deleterious effect of plant transit peptides on recombinant expression and folding (Williams et al. 1998). Comparison of the enzymatically formed compound to similarly dephosphorylated authentic samples of ent- and syn-CPP demonstrated that the enzyme produces syn-CPP (FIG. 3). Therefore, this is the rice syn-CPP synthase (OsCPS4$_{syn}$).

Expression pattern of OsCPS4$_{syn}$ mRNA. The metabolic fate of syn-CPP is thought to be limited to phytoalexin/allelopathic natural products. Therefore, regulation of OsCPS4$_{syn}$ activity, which catalyzes the committed biosynthetic step, provides a logical point for controlling the production of these natural products. Previous review of the relevant literature has been used to suggest that plant secondary metabolism is most often regulated at the level of transcription (Peters and Croteau 2004). Transcriptional control is manifested by upregulation of enzymatic mRNA levels, with subsequent phytochemical accumulation, in response to the appropriate environmental conditions. The convenience of UV-irradiation for induction of phytoalexin biosynthesis in rice leaves has long been appreciated (Cartwright et al. 1977). In fact, this was utilized in the recently reported large-scale cDNA project from which the original sequence for OsCPS4$_{syn}$ is derived (Kikuchi et al. 2003). Further, quantitative analysis of phytochemical accumulation for the detached leaf UV-irradiation induction method used here has been previously reported (Kodama et al. 1988). Therefore, the ability of UV-irradiation to induce expression of OsCPS4$_{syn}$ mRNA in rice leaves was characterized, demonstrating transcriptional upregulation prior to phytoalexin accumulation (FIG. 6). In addition, OsCPS4$_{syn}$ transcription is induced by methyl jasmonate, an important plant defense signaling molecule (Farmer and Ryan 1990), which, as free jasmonic acid, has been previously demonstrated to induce phytoalexin biosynthesis in rice cell culture (Nojiri et al. 1996). Also consistent with a role in defense, five of the six expressed sequence tags (EST) currently associated with OsCPS4$_{syn}$ in the TIGR Gene Index are from blast pathogen infected rice EST projects (www.tigr.org; rice|TC205530). Finally, as expected from its requisite role in constant production of an allelochemical (Kato-Noguchi and Ino 2003), OsCPS4$_{syn}$ mRNA seems to be constitutively present in roots (FIG. 6). These results strongly indicate that biosynthesis of the corresponding syn-labdane-related diterpenoid natural products is controlled, at least in part, by transcriptional regulation of OsCPS4$_{syn}$.

Figure 2:
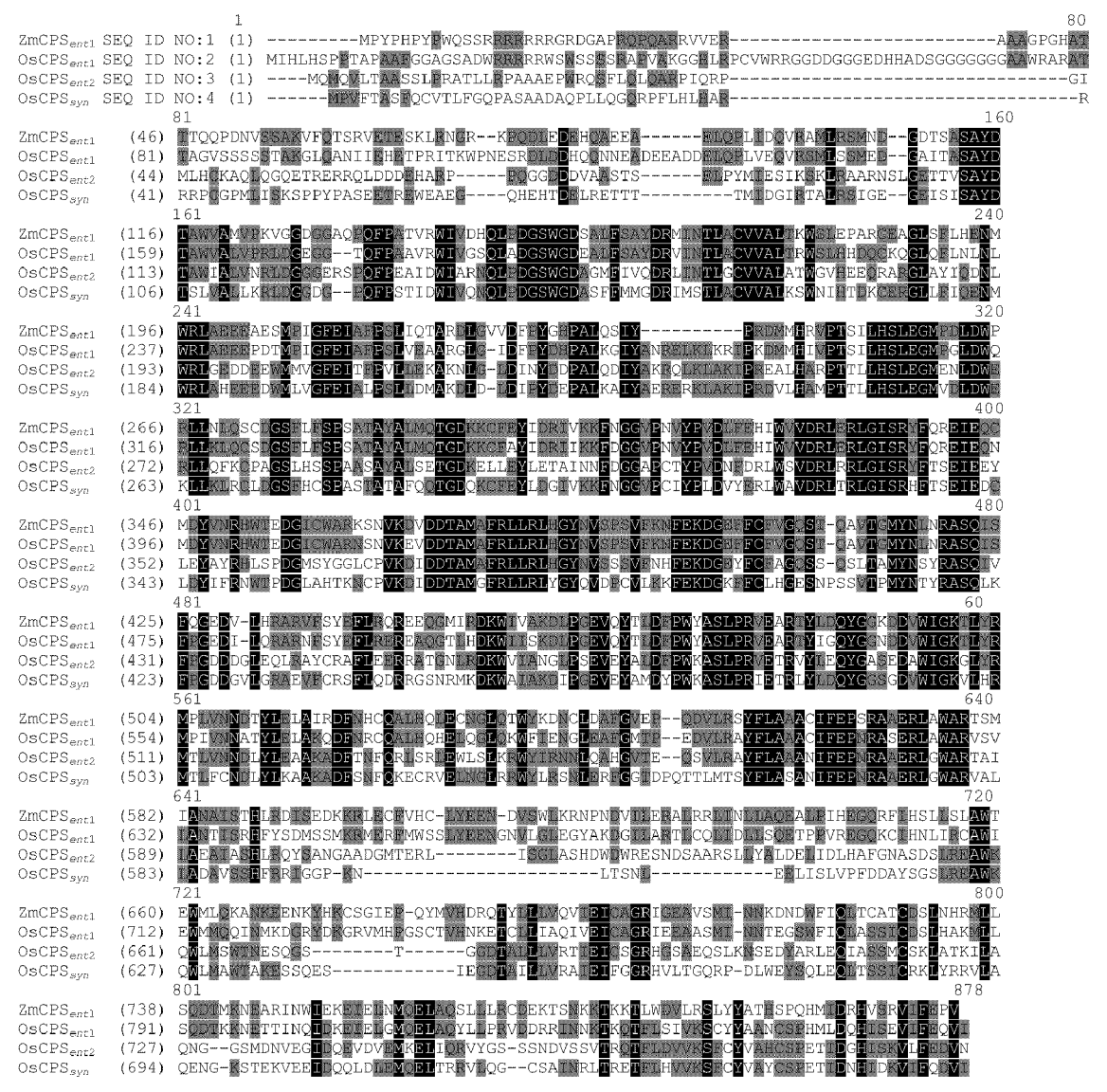

Sequence comparison of OsCPS4$_{syn}$ with other class II terpene synthases. As selected for by the identification strategy, OsCPS$_{syn}$ contains not only the requisite DXDD motif, but also the class II synthases associated "insertional" element (FIG. 2). In addition, OsCPS4$_{syn}$ clearly does not contain the C-terminal domain DDXXD metal ion binding motif required for class I catalysis (Davis and Croteau, 2000), explaining its inability to catalyze the corresponding diphosphate ionization reaction. Amino acid alignment of OsCPS4$_{syn}$ with the other known class II terpene synthases from plants demonstrates the expected homology (FIG. 2). Specifically, OsCPS4$_{syn}$ is 38-44% identical with CPS$_{ent}$ (required for gibberellin plant growth hormone biosynthesis) from various angiosperms (Sun and Kamiya 1994; Bensen et al. 1995; Ait-Ali et al. 1997; Smith et al. 1998; Rebers et al. 1999; Richman et al. 1999) and 28% identical with the known gymnosperm bifunctional class II/I terpene synthases, which produce normal CPP (Stofer Vogel et al. 1996; Schepmann et al. 2001; Martin et al. 2004).

EXAMPLE 2

Functional Identification of syn-CPP Specific 9β-pimara-7,15-diene Synthase

Chemicals. Synthesis of (E,E,E)-geranylgeranyl diphosphate (GGPP), ent- and syn-copalyl diphosphate (CPP), and the polycyclic hydrocarbon standards ent-kaurene, ent-sandaracopimaradiene, syn-pimara-7,15-diene, and syn-stemar-13-ene have been previously described (Mohan et al., 1996). Unless otherwise noted, all other chemicals were purchased from Fisher Scientific.

Plant material. Rice plants (*Oryza sativa* L. ssp. *indica* cv. IR24) and seedlings (ssp. *japonica* cv. Nipponbare) were those previously described (Xu et al., 2004). Briefly, detached leaves from four-week old greenhouse grown plants were UV-irradiated at 254 nm from 15 cm distance for 25 min. and then incubated for the indicated period of time under dark humid conditions at 30° C. Seedlings were germinated from surface sterilized seeds under sterile, humid conditions at 30° C. in the dark for a week. The seedlings then underwent MeJA treatment, being sprayed with 2 mL 0.1% Tween 20±0.5 mM MeJA per gram of plant weight, and the seedlings then incubated for two more days under the same conditions. RNA was isolated using Concert Plant Reagent (Invitrogen; Carlsbad, Calif., USA). Semi-quantitative RT-PCR expression analysis, using 0.5 µg total RNA and OsDTS2-specific primers or QuantumRNA 18S standard primers (Ambion; Austin, Tex., USA), was also carried out as described by Xu et al. (2004).

Cloning. A putative class I terpene synthase involved in labdane-related biosynthesis was identified by a BLAST search of the GenBank database (www.ncbi.nlm.nih.gov:80/BLAST/) with the amino acid sequence of ent-kaurene synthase from *Arabidopsis* (Yamaguchi et al., 1998). RT-PCR reactions were performed to verify expression of the predicted gene in UV-irradiated leaves by generating a fragment of the corresponding sequence. This was verified by cloning into pCR-Zero-Blunt (Invitrogen) and complete sequencing. These primers were also then used for the semi-quantitative RT-PCR expression analysis. The complete open reading frame for OsDTS2 was then amplified from total RNA in an RT-PCR reaction using the GeneRacer kit (Invitrogen), cloned into pENTR/SD/D-TOPO (Invitrogen), and verified by complete sequencing. OsDTS2 was then transferred by directional recombination to the T7 based expression vectors pDEST14 and pDEST15 (Gateway system, Invitrogen).

Recombinant expression and functional characterization. Expression was carried out with the BL21-derived C41 strain (Miroux and Walker, 1996), as described for OsCPS$_{syn}$ by Xu et al. (2004). Briefly, cells were grown to mid-log phase at 37° C. then shifted to 16° C. for 1-2 h prior to induction (1 mM IPTG) and overnight expression. The cells were harvested by centrifugation (3000 g, 20 min, 5° C.), re-suspended in 1 mL of lysis buffer (50 mM Bis-Tris, pH 6.8, 150 mM KCl, 10 mM MgCl$_2$, 1 mM DTT), and lysed by mild sonication on ice (Branson sonifier 450: 20 s, continuous, output setting 5). The resulting lysates were cleared by centrifugation (15,000 g, 30 min, 5° C.) and filtration (0.8µ) to yield recombinant soluble extracts. Enzymatic assays were performed with these preparations under standard conditions defined for diterpene synthase activity [e.g., (Peters et al., 2000)]. Briefly, reactions with ~50 µM substrate (GGPP, ent-, or syn-CPP) were carried out in assay buffer (50 mM HEPES, pH 7.2, 100 mM KCl, 7.5 mM MgCl$_2$, 5% glycerol, and 5 mM DTT) with 25 µL of recombinant protein in a total volume of 0.2 mL. The reaction was allowed to proceed for 3 h at 30° C. prior to extraction with hexanes. GC-MS analysis was performed using an HP-5 column on an Agilent (Palo Alto, Calif., USA) 6890N GC instrument with 5973N mass selective detector. Samples (5 µL) were injected at 40° C. in the splitless mode. After holding 3 min. at 40° C., the temperature was increased at 20° C./min. to 300° C., where it was held for 3 min. MS data was collected from 50 to 500 m/z during the temperature ramp. The retention time (RT) and MS pattern were compared to those for syn-stemar-13-ene and syn-pimara-7,15-diene, as well as sandaracopimaradiene and ent-kaurene.

Sequence analysis and alignments. Sequence alignments and identity calculations were performed with the AlignX program in the Vector NTI software package (Invitrogen), using standard parameters. OsDTS2 was the reference sequence in all cases. The class I terpene synthases are not involved in labdane-related diterpenoid biosynthesis, yet containing 'insertional' elements, are linalool synthase from *Clarkia breweri* (Dudareva et al., 1996), taxadiene synthase from *Taxus brevifolia* (Wildung and Croteau, 1996), and bisabolene synthase from *Abies grandis* (Bohlmann et al., 1998b). Bifunctional class II/I terpene synthases producing labdane-related diterpenes of normal stereochemistry are those from the gymnosperms *Abies grandis* (Stofer Vogel et al., 1996), *Ginkgo biloba* (Schepmann et al., 2001), and *Picea abies* (Martin et al., 2004). The ent-kaurene synthases were those from *Curcurbita maxima* (Yamaguchi et al., 1996), *Arabidopsis thaliana* (Yamaguchi et al., 1998), and *Stevia rebaudiana* (Richman et al., 1999). Other rice class I terpene synthases with potential involvement in labdane-related diterpenoid biosynthesis were identified by BLAST queries of GenBank, and the cDNA databases at KOME (cdna01.dna.affrc.go.jp/cDNA/) and TIGR (tigrblast.tigr.org/tgi/), using *Arabidopsis* ent-kaurene synthase as the probe sequence.

Results

Isolation of a class I terpene synthase cDNA from UV-irradiated rice leaves. The class I terpene synthases involved in labdane-related diterpenoid biosynthesis discriminate between different stereoisomers of CPP and, thus, provide a model system for investigating the underlying active site steric constraints. In addition, terpene synthases are conserved by taxonomic origin rather than biochemical function (Bohlmann et al., 1998a). Therefore, the inventors were interested in identifying a syn-CPP specific class I terpene synthase from rice to complement the previously identified ent-CPP specific cassa-12,15-diene synthase (Cho et al., 2004). Towards this end, an initial class I terpene synthase with potential involvement in labdane-related diterpenoid biosynthesis (i.e., DDXXD motif and 'insertional' element) was found among the genes predicted from the finished sequence of rice chromosome 4 [accession CAD39507; (Feng et al., 2002)]. The corresponding sequence was readily amplified from UV-irradiated rice leaves, cloned, and verified by complete sequencing of two independent isolates, demonstrating ~99% identity to the predicted sequence. Presumably the few observed differences are a function of intersubspecies variation between the ssp. *japonica* sequenced by Feng et al. (2002) and ssp. *indica* used here (our sequence has been deposited into the various nucleotide sequence databases as accession AY616862).

Sequence comparison suggests a role in labdane-related diterpenoid biosynthesis. The cloned open reading frame encodes a protein of 840 amino acids that contains the 'insertional' element associated with labdane-related diterpene synthases. Also present is the catalytically requisite class I DDXXD motif, as found in the original gene prediction (accession CAD39507). Notably, the currently predicted gene product does not include the exon containing this metal binding motif (accession CAD39717), indicating that caution must be taken when analyzing predicted genes (i.e., the current prediction might be mistaken as a non-functional 'pseudo-gene'). Significantly, the DXDD motif required for class II cyclization is not found. Alignment of the complete amino acid sequence with that of known 'insertional' element containing class I terpene synthases demonstrated only weak similarity (<27% identity) to those not involved in labdane-related diterpenoid biosynthesis (Dudareva et al., 1996; Wildung and Croteau, 1996; Bohlmann et al., 1998b). Slightly higher similarity (~30% identity) was found with the identified gymnosperm bifunctional class II/I diterpene synthases, which are involved in labdane-related biosynthesis (Stofer Vogel et al., 1996; Schepmann et al., 2001; Martin et al., 2004). Further, the sequence is moderately similar (39-42% identity) to the known ent-kaurene synthases involved in gibberellin biosynthesis (Yamaguchi et al., 1996; Yamaguchi et al., 1998; Richman et al., 1999). Finally, comparison with the recently identified ent-CPP specific cassa-12,15-diene synthase (Cho et al., 2004) revealed significant homology (~51% identity). These results suggest, although do not demonstrate, that the isolated sequence is also a labdane-related (i.e., CPP specific) diterpene synthase (OsDTS2).

Figure 5:
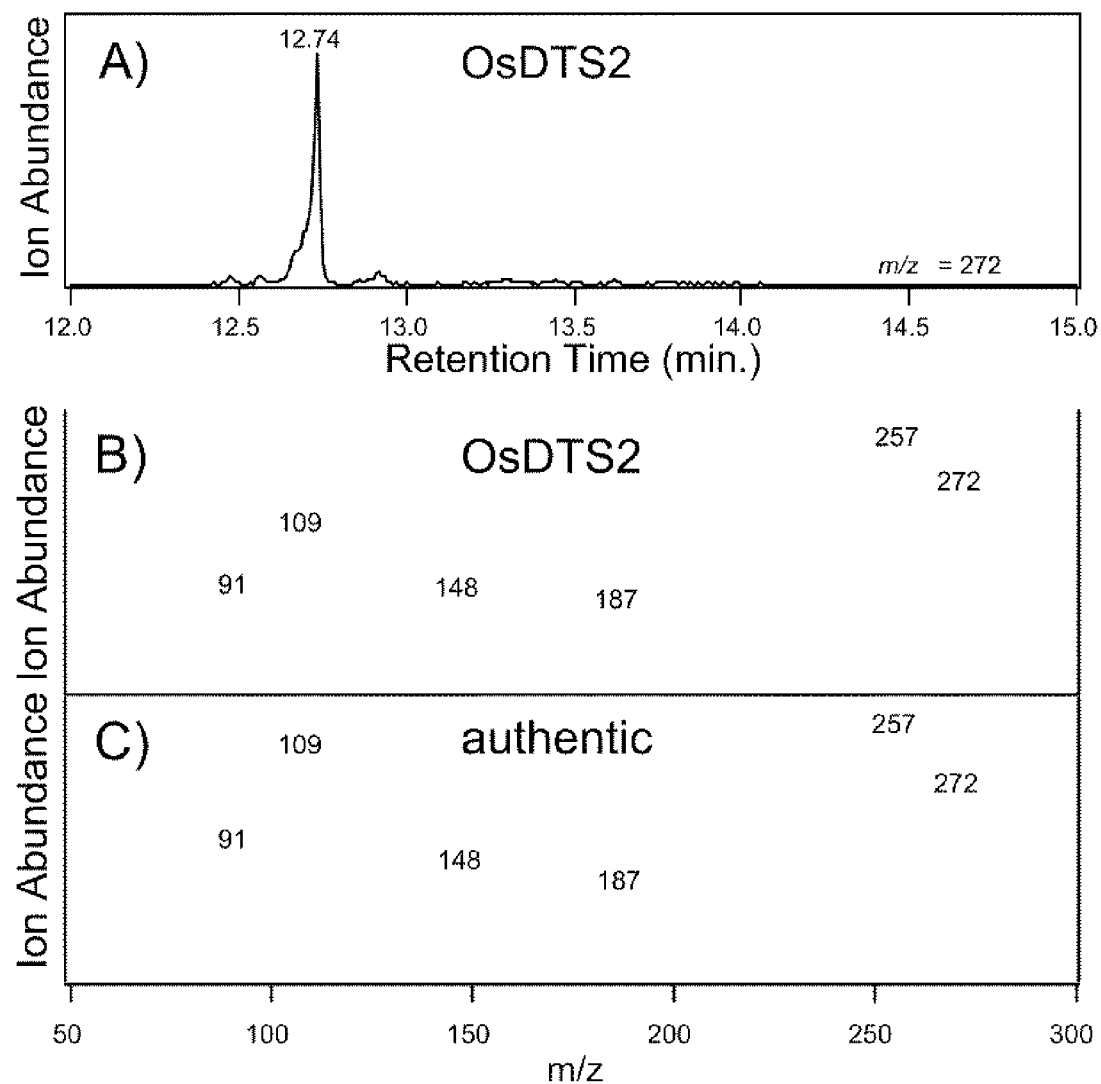
FIG. 5 shows identification of enzymatic products for OsDTS2: A) GC-MS analysis (272 m/z extracted ion chromatographs) of the reaction product from syn-CPP, B) Mass spectrum of the enzymatic GC-MS 272 m/z chromatograph peak (RT=12.74 min.), C) Mass spectrum of authentic 9β-pimara-7,15-diene, which also exhibits RT=12.74 min.

Functional characterization of OsDTS2 as syn-CPP specific 9μ-pimara-7,15-diene synthase. OsDTS2 was expressed both alone and as a fusion protein to glutathione-S-transferase (GST-OsDTS2). Recombinant preparations were assayed with GGPP, ent-CPP or syn-CPP as substrate and enzymatic activity detected using gas chromatography-mass spectrometry (GC-MS) analysis of organic extracts of the assays. Only the GST-OsDTS2 fusion protein exhibited appreciable amounts of activity, indicating the transit peptide (required for plastidial import in planta) hinders folding of the full-length preprotein in the absence of the stabilizing effect provided by the fused GST structure, as found in previous studies (Williams et al., 1998; Peters et al., 2000). Further, enzymatic turnover was only observed with syn-CPP, as no products were detected from reactions with GGPP or ent-CPP. Therefore, OsDTS2 is stereoselective and represents the first identified class I terpene synthase specific for syn-CPP. Finally, comparison with the known synthetic standards (Mohan et al., 1996) unambiguously identified the enzymatic product as syn-pimara-7,15-diene (FIG. 5).

Expression pattern of OsDTS2 mRNA. The production of 9β-pimara-7,15-diene from syn-CPP is the committed step in momilactone biosynthesis (FIG. 1). Therefore, regulation of the corresponding activity (i.e., OsDTS2) provides a logical point for controlling the production of these specific labdane-related diterpenoid natural products. Previous review of the relevant literature has been used to suggest that plant secondary metabolism is most often regulated at the level of transcription (Peters and Croteau, 2004). This has been demonstrated for the preceding enzyme $OsCPS_{syn}$, where the corresponding mRNA increases prior to syn-labdane-related diterpenoid phytochemical accumulation in UV-irradiated rice leaves (Xu et al., 2004). Nevertheless, it seemed likely that OsDTS2 would also be regulated, as OsDTC1 is similarly controlled (Cho et al., 2004), in addition to the observed transcriptional control of the upstream enzyme $OsCPS_{ent2}$ (Prisic et al., 2004). Such a control mechanism was investigated through the use of UV-irradiation, which has long been appreciated to induce phytoalexin biosynthesis in rice (Cartwright et al., 1977). Further, quantitative analysis of phytochemical accumulation for the detached leaf UV-irradiation induction method used here has been previously reported (Kodama et al., 1988). Hence, the ability of UV-irradiation to induce expression of OsDTS2 mRNA in rice leaves was characterized, demonstrating transcriptional upregulation prior to phytoalexin accumulation (FIG. 8). To verify that such transcriptional control is part of the normal regulatory mechanism for phytoalexin biosynthesis, it was further demonstrated that OsDTS2 mRNA levels are also increased by methyl jasmonate (MeJA), an important plant defense signaling molecule (Farmer and Ryan, 1990). MeJA has also been previously demonstrated to induce phytoalexin biosynthesis in rice cell culture (Nojiri et al., 1996), as well as transcription of the phytoalexin specific class II terpene synthases $OsCPS_{ent2}$ and $OsCPS_{syn}$ (Prisic et al., 2004; Xu et al., 2004). Finally, as expected from its requisite role in constant production of an allelochemical (Kato-Noguchi and Ino, 2003), OsDTS2 mRNA seems to be constitutively present in roots, albeit at a low level, again correlated with the expression pattern for $OsCPS_{syn}$ (Xu et al., 2004). These results strongly indicate that, in addition to the previously observed transcriptional regulation of $OsCPS_{syn}$ (Xu et al., 2004), biosynthesis of the phytoalexin/allelochemical momilactones is also more specifically controlled by transcriptional regulation of OsDTS2.

EXAMPLE 3

Isolation and Functional Identification of Rice ent-CPP Synthases

Chemicals. (E,E,E)-geranylgeranyl diphosphate (GGPP), and ent- and syn-copalyl diphosphate (CPP) were synthesized as previously described (Mohan et al., 1996). Unless otherwise noted, all other chemicals were purchased from Fisher Scientific.

Plant Material. Rice plants (*Oryza sativa* L. ssp. *indica* cv. IR24) and seedlings (ssp. *japonica* cv. Nipponbare) were those previously described (Xu et al., 2004). Briefly, detached leaves from three week old greenhouse grown plants were UV-irradiated at 254 nm from 15 cm distance for 25 min. and then incubated for the indicated period of time under dark humid conditions at 30° C. Seedlings were sterilized and germinated for a week under sterile humid conditions at 30° C. in the dark. Maize (*Zea maize* L. cv. B73) seedlings were germinated for four days under identical conditions. After germination, the seedlings underwent MeJA treatment, being sprayed with 2 mL 0.1% Tween 20±0.5 mM MeJA per gram of plant weight, and the seedlings then incubated for two more days under the same conditions. RNA was isolated using Concert Plant Reagent (Invitrogen; Carlsbad, Calif., USA). Semi-quantitative RT-PCR expression analysis, using 0.5 μg total RNA and the gene-specific primers described in Table 2 or QuantumRNA 18S standard primers (Ambion; Austin, Tex., USA), was also carried out.

TABLE 2

Primers

| | Forward Primer | Reverse Primer |
|---|---|---|
| $OsCPS1_{ent}$ | GAAAAGGATG GAGCGTTTCAT (SEQ ID NO:17) | TCAAATAACT TGCTCAAAAA TCACTTCAGA AATGTGTTGG TCAA (SEQ ID NO:18) |
| $OsCPS2_{ent}$ | CCTACCGCGC CTCGCAG (SEQ ID NO:19) | GTCGATGAGC TCATCAAGTG (SEQ ID NO:20) |
| $An1/ZmCPS1_{ent}$ | ATTGCGAAAT GGCAGGAAACC (SEQ ID NO:21) | TCCTGTCGAT GTATTCGAAGC (SEQ ID NO:22) |

Cloning. Three putative class II terpene synthases were identified by BLAST queries of the rice genomic and EST databases with the nucleotide sequence of ent-copalyl diphosphate synthase from *Arabidopsis* (Yamaguchi et al., 1998). RT-PCR reactions were performed to verify expression of two of the predicted genes in UV-irradiated rice leaves by generating fragments of the corresponding sequences ($OsCPS1_{ent}$ and $OsCPS2_{ent}$). The ultimately successful primer pairs are those given in Table 2. All fragments were cloned into pCR-Zero-Blunt (Invitrogen) and verified by complete sequencing. Notably, the $OsCPS1_{ent}$ fragment covers the region containing the alternate EXDD motif. Thus, the $OsCPS1_{ent}$ gene in both the spp. *indica* used here and the originally reported *japonica* (Kikuchi et al., 2003) contain this alternative motif. The full-length cDNA for OsCPS1$_{ent}$ was obtained from the rice full-length cDNA sequencing project (www.rgrc.dna.affrc.go.jp). To obtain the open reading frame for OsCPS2$_{ent}$, 3' RACE (GeneRacer; Invitrogen) was performed using the 5' end primer ATGCAGATGCAG-GTGCTCACC (SEQ ID NO:23). The 5' untranslated region was obtained by 5' RACE using the reverse primer given in Table 2. Both RACE products were cloned into pCR-Zero-Blunt and completely sequenced, demonstrating identical sequence in the 1932 bp overlap. Truncated versions of both OsCPS1$_{ent}$ and OsCPS2$_{ent}$ were then cloned into pENTR/SD/D-TOPO via PCR amplification for direction topoisomerization and verified by complete sequencing. These were then transferred by directional recombination to the T7 based expression vector pDEST14 (Gateway system, Invitrogen).

Recombinant expression and functional characterization. Expression was carried out with the BL21 derived from C41 strain (Miroux and Walker 1996). Briefly, cells were grown to mid-log phase at 37° C. then shifted to 16° C. for 1-2 h prior to induction (1 mM IPTG) and overnight expression. Lysates were prepared by sonication and the recombinant protein partially purified by batch binding to ceramic hydroxyapatite type II (Bio-Rad; Hercules, Calif., USA) and elution into 0.2 M sodium phosphate (pH 6.8), as previously described (Peters and Croteau 2003). Enzymatic assays were performed with these preparations. Briefly, reactions with 5 µM GGPP were carried out for 1 h at 30° C. under standard conditions defined for diterpene synthase activity [e.g., (Peters et al. 2000)] prior to enzymatic dephosphorylation (phosphatase) to allow GC-MS analysis. This was performed using an HP-5 column on an Agilent (Palo Alto, Calif., USA) 6890N GC instrument with 5973N mass selective detector. Samples (5 µL) were injected at 40° C. in the splitless mode. After holding 3 min. at 40° C., the temperature was increased at 20° C./min. to 300° C., where it was held for 3 min. MS data was collected from 50 to 500 m/z during the temperature ramp.

Sequence analysis and alignments. Sequence alignments, identity calculations, and phylogenetic analysis were performed with the AlignX program in the Vector NTI software package (Invitrogen), using standard parameters. An1/ZmCPS1$_{ent}$ was the reference sequence for alignment and phylogenetic analysis of Poaceae class II terpene synthases. For individual comparisons with dicot CPS1$_{ent}$ the rice genes were defined as the reference sequence. The CPS1$_{ent}$ sequences were those from *Arabidopsis thaliana* (Sun and Kamiya, 1994), *Pisum sativum* (Ait-Ali et al., 1997), *Curcurbita maxima* (Smith et al., 1998), *Lycopersicon escclentum* (Rebers et al., 1999), and *Stevia rebaudiana* (Richman et al., 1999). The gymnosperm bifunctional class II/I terpene synthase sequences were those from *Abies grandis* (Stofer Vogel et al., 1996), *Ginkgo biloba* (Schepmann et al., 2001), and *Picea abies* (Martin et al., 2004).

Results

Functional identification of two ent-CPP synthases from rice. Due to the inventors interest in the functionally distinct class II terpene synthases as potentially significant targets for metabolic engineering and biochemical analysis, three putative class II terpene synthases were identified from the extensive sequence information available for rice (Goff et al., 2002; Yu et al., 2002; Kikuchi et al., 2003). One of these was readily amplified from mRNA prepared from UV-irradiated rice leaves and found to produce syn-CPP for phytoalexin/allelochemical biosynthesis [accession AY530101; (Xu et al., 2004)]. The second class II terpene synthase gene was not as easily isolated. Nevertheless, the inventors have now cloned the corresponding full-length cDNA and deposited the associated sequence into the various nucleotide databases as accession AY602991. The third gene was available from the rice full-length cDNA sequencing project [accession AK100333; (Kikuchi et al., 2003)] and obtained from this source (www.rgrc.dna.affrc.go.jp). Notably, this last gene sequence contains EXDD in place of the otherwise conserved DXDD motif functionally associated with class II cyclization. This was confirmed by independently cloning a gene fragment covering this region.

Figure 4:
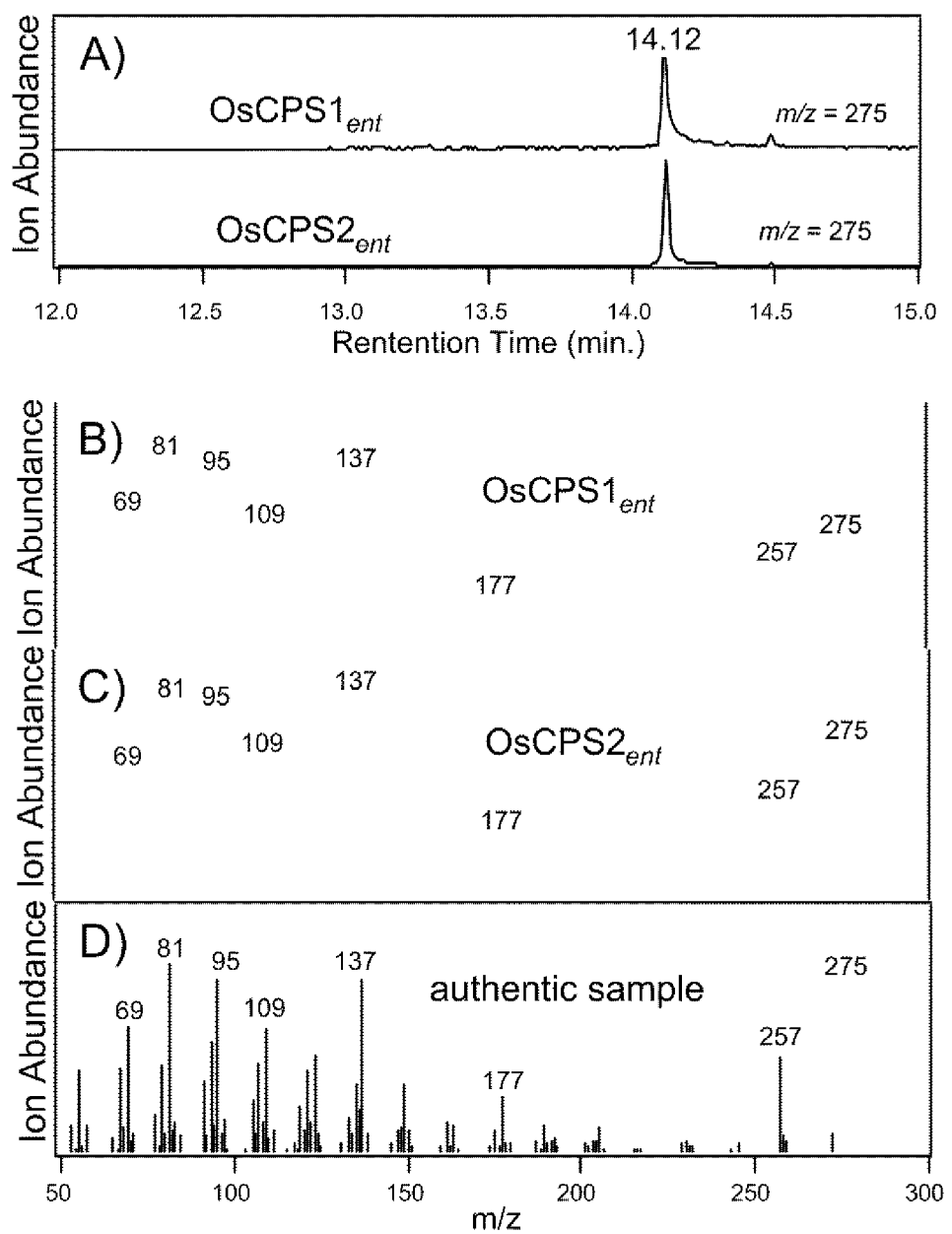
FIG. 4 shows identification of enzymatic products for $OsCPS1_{ent}$ and $OsCPS2_{ent}$: A) GC-MS analysis (275 m/z extracted ion chromatographs) of the dephosphorylated reaction products from GGPP produced by the indicated enzyme, B) Mass spectrum of the GC-MS 275 m/z chromatograph peak for $OsCPS1_{ent}$ (RT=14.12 min.); C) that for $OsCPS2_{ent}$ (RT=14.12 min.); D) that for authentic dephosphorylated ent-CPP (i.e. ent-copalol), which also exhibits RT=14.12 min.

Work with OsCPS4$_{syn}$ suggested that removal of the N-terminal transit peptide required for the plastidal location of diterpene synthases in planta, forming a pseudo-mature construct, was required for functional expression. Thus, for each of the two unidentified class II terpene synthases, truncated versions were constructed for recombinant expression (see FIG. 2). These were based on the pseudo-mature form of OsCPS$_{syn}$ and truncation analysis of the *Arabidopsis* CPS1$_{ent}$. Enzymatic assays were carried out with partially purified recombinant preparations and GGPP as substrate. Phosphatase treatment was then employed to remove the pyrophosphate from GGPP and any enzymatically formed derivative, to enable straightforward extraction of the resulting alcohol into organic solvent. Enzymatic conversion of GGPP was analyzed by gas chromatography-mass spectrometry (GC-MS) of the resulting extracts, demonstrating production of an altered phenyl diphosphate structure. Comparison of the enzymatically formed compound to similarly dephosphorylated authentic samples of ent- and syn-CPP demonstrated that both enzymes produce ent-CPP (FIG. 4). Two rice ent-CPP synthases have therefore been functionally identified (OsCPS1$_{ent}$ and OsCPS2$_{ent}$).

Differential regulation of OsCPS1$_{ent}$ and OsCPS2$_{ent}$ expression. To distinguish between potential roles for OsCPS1$_{ent}$ and OsCPS2$_{ent}$ in primary and/or secondary metabolism, both genes were examined for a differential response to methyl jasmonate (MeJA). Application of this important plant defense signaling molecule has been previously shown to induce phytoalexins biosynthesis in rice cell culture (Nojiri et al., 1996). Further, we have recently demonstrated that OsCPS$_{syn}$ mRNA is upregulated in response to MeJA (Xu et al., 2004). However, enzymes solely involved in gibberellin biosynthesis should not be affected. Consistent with this interpretation, it has been shown that the maize gibberellin specific class II terpene synthase An1/ZmCPS1$_{ent}$ is not significantly upregulated by MeJA. Thus, the rice ent-CPP synthase from the large-scale cDNA project (accession AK100333), whose expression is also not increased by MeJA, is proposed to be involved in gibberellin biosynthesis and specifically designated OsCPS1$_{ent}$. In contrast, the gene cloned here (accession AY602991) is clearly upregulated by MeJA, indicating a role in defensive secondary metabolism, and has been designated OsCPS2$_{ent}$. Also consistent with a role in defense, 16 of the 21 expressed sequence tags (EST) currently associated with OsCPS2$_{ent}$ in the TIGR Gene Index are from blast pathogen infected rice EST projects. Notably, these results are further consistent with the recently reported identification of rice gibberellin biosynthetic genes by mutant plant phenotype, in particular, the assignment of OsCPS1$_{ent}$ to gibberellin metabolism (Sakamoto et al., 2004).

Previous review of the relevant literature has been used to suggest that plant secondary metabolism is most often regulated at the level of transcription (Peters and Croteau, 2004). This has been demonstrated for OsCPS$_{syn}$, where upregulation of enzymatic mRNA levels occurs prior to phytochemical accumulation in UV-irradiated rice leaves. Similar results are reported here for OsCPS2$_{ent}$, indicating that biosynthesis of the ent-labdane-related diterpenoid phytoalexins is also regulated to some extent by controlling transcription of the associated class II terpene synthase (FIGS. 6-7). Finally, and somewhat unexpectedly, OsCPS2$_{ent}$ is additionally constitutively expressed at low levels in the roots (FIG. 7), at least partially accounting for the observed expression in control seedlings. Such root specific constitutive expression has also been demonstrated for OsCPS$_{syn}$, and these results suggest that ent-CPP derived phytochemicals may also be secreted to the rhizosphere, along with the known secretion of syn-CPP derived, and allelopathic acting, momilactone B (Kato-Noguchi and Ino 2003).

Conservation of class II terpene synthases within Poaceae. Not surprisingly, given their common origin from within the cereal/grass plant family (Poaceae), the rice class II terpene synthases are most similar to An1/ZmCPS1$_{ent}$, from maize [(Bensen et al., 1995); FIG. 2]. Outside of Poaceae, amino acid alignment of OsCPS1$_{ent}$ and OsCPS2$_{ent}$ with known class II terpene synthases also demonstrates the expected homology. Specifically, OsCPS1$_{ent}$ shares 42-45% identity with the other known gibberellin specific CPS$_{ent}$, all of which are from various dicot species (Sun and Kamiya, 1994; Ait-Ali et al., 1997; Smith et al., 1998; Rebers et al., 1999; Richman et al., 1999), and ~30% identity with the known gymnosperm bifunctional class II/I terpene synthases (Stofer Vogel et al., 1996; Schepmann et al., 2001; Martin et al., 2004). Somewhat lower homology is found for OsCPS2$_{ent}$, which shares 37-40% identity with CPS$_{ent}$ from dicots and ~27% identity with the gymnosperm bifunctional terpene synthases. This is similar to the homology levels observed with OsCPS4$_{syn}$, which shares 38-42% identity with dicot CPS$_{ent}$ and ~28% identity with the bifunctional gymnosperm enzymes. Significantly, OsCPS1$_{ent}$ is much more similar to An1/ZmCPS1$_{ent}$ (64% identity) than either of its paralogs, OsCPS2$_{ent}$ or OsCPS$_{syn}$, which are each only 44% identical to OsCPS1$_{ent}$. OsCPS2$_{ent}$ and OsCPS$_{syn}$ are also only marginally more similar to An1/ZmCPS1$_{ent}$ (42% and 44% identity, respectively) than to CPS$_{ent}$ from dicots. However, despite the difference in product stereochemistry, OsCPS2$_{ent}$ and OsCPS$_{syn}$ are relatively closely related, exhibiting 53% identity.

For the above-stated reasons, it is submitted that the present invention accomplishes at least all of its stated objectives.

Having described the invention with reference to particular compositions and methods, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended.

All articles cited herein and in the following list are hereby expressly incorporated in their entirety by reference.

CITATIONS

Ait-Ali, T., Swain, S. M., Reid, J. B., Sun, T., and Kamiya, Y. 1997. The LS locus of pea encodes the gibberellin biosynthesis enzyme ent-kaurene synthase A. *Plant J.* 11: 443-454.

Akatsuka, T., Kodama, O., Sekido, H., Kono, Y., and Takeuchi, S. 1985. Novel Phytoalexins (Oryzalexins A, B, and C) Isolated from Rice Blast Leaves Infected with *Pyricularia oryzae*. Part I: Isolation, Characterization and Biological Activities of Oryzalexins. *Agric. Biol. Chem.* 49: 1689-1694.

Bais, H. P., Park, S.-W., Weir, T. L., Callaway, R. M., and Vivanco, J. M. 2004. How plants communicate using the underground information superhighway. *Trends Plant Sci.* 9: 26-32.

Bensen, R. J., Johal, G. S., Crane, V. C., Tossberg, J. T., Schnable, P. S., Meeley, R. B., and Briggs, S. P. 1995. Cloning and characterization of the maize An1 gene. *Plant Cell* 7: 75-84.

Bohlmann, J., Crock, J., Jetter, R., and Croteau, R. B. 1998a. Terpenoid-based defenses in conifers: cDNA cloning, characterization, and functional expression of wound-inducible (E)-alpha-bisabolene synthase from grand fir (*Abies grandis*). *Proc Natl Acad Sci USA.* 95: 6756-6761.

Bohlmann, J., Meyer-Gauen, G., and Croteau, R. 1998b. Plant terpenoid synthases: Molecular biology and phylogenetic analysis. *Proc. Natl. Acad. Sci. USA* 95: 4126-4133.

Cartwright, D. W., Langcake, P., Pryce, R. J., Leworthy, D. P., and Ride, J. P. 1977. Chemical activation of host defence mechanisms as a basis for crop protection. *Nature* 267: 511-513.

Cartwright, D. W., Langcake, P., Pryce, R. J., Leworthy, D. P., and Ride, J. P. 1981. Isolation and characterization of two phytoalexins from rice as momilactones A and B. *Phytochemistry* 20: 535-537.

Cho, E.-M., Okada, A., Kenmoku, H., Otomo, K., Toyomasu, T., Mitsuhashi, W., Sassa, T., Yajima, A., Yabuta, G., Mori, K., et al. 2004. Molecular cloning and characterization of a cDNA encoding ent-cassa-12,15-diene synthase, a putative diterpenoid phytoalexin biosynthetic enzyme, from suspension-cultured rice cells treated with a chitin elicitor. *Plant J.* 37: 1-8.

Croteau, R., Kutchan, T. M., and Lewis, N. G. 2000. Natural Products (Secondary Metabolites). In *Biochemistry & Molecular Biology of Plants*. (eds. B. Buchanan, W. Gruissem, and R. Jones), pp. 1250-1318. Am. Soc. Plant Biologists, Rockville, Md., USA.

Davis, E. M., and Croteau, R. 2000. Cyclization Enzymes in the Biosynthesis of Monoterpenes, Sesquiterpenes, and Diterpenes. *Top. Curr. Chem.* 209: 53-95.

Dudareva, N., Cseke, L., Blanc, V. M., and Pichersky, E. 1996. Evolution of Floral Scent in *Clarkia*: Novel Patterns of S-Linalool Synthase Gene Expression in the *C. breweri* Flower. *Plant Cell* 8: 1137-1148.

Farmer, E. E., and Ryan, C. A. 1990. Interplant communication: Airborne methyl jasmonate induces synthesis of proteinase inhibitors in plant leaves. *Proc Natl Acad Sci USA.* 87: 7713-7716.

Goff, S. A., Ricke, D., Lan, T. H., Presting, G., Wang, R., Dunn, M., Glazebrook, J., Sessions, A., Oeller, P., Varma, H., et al. 2002. A draft sequence of the rice genome (*Oryza sativa* L. ssp. *japonica*). *Science* 296: 92-100.

Kato, H., Kodama, O., and Akatsuka, T. 1993. Oryzalexin E, a diterpene phytoalexin from UV-irradiated rice leaves. *Phytochemistry* 33: 79-81.

Kato, H., Kodama, O., and Akatsuka, T. 1994. Oryzalexin F, a diterpene phytoalexin from UV-irradiated rice leaves. *Phytochemistry* 36: 299-301.

Kato, T., Kabuto, C., Sasaki, N., Tsunagawa, M., Aizawa, H., Fujita, K., Kato, Y., Kitahara, Y., and Takahashi, N. 1973. Momilactones, growth inhibitors from rice, *Oryza sativa* L. *Tetrahedron Lett.* 14: 3861-3864.

Kato-Noguchi, H., and Ino, T. 2003. Rice seedlings release momilactone B into the environment. *Phytochemistry* 63: 551-554.

Keegstra, K., Olsen, L. J., and Theg, S. M. 1989. Chloroplastic precursors and their transport across the envelope membranes. *Annu. Rev. Plant Physiol. Plant Mol. Biol.* 40: 471-501.

Kikuchi, S., Satoh, K., Nagata, T., Kawagashira, N., Doi, K., Kishimoto, N., Yazaki, J., Ishikawa, M., Yamada, H., Ooka, H., et al. 2003. Collection, Mapping, and Annotation of Over 28,000 cDNA Clones from *japonica* Rice. *Science* 301: 376-379.

Kodama, O., Li, W. X., Tamogami, S., and Akatsuka, T. 1992. Oryzalexin-S, a novel stemarane-type diterpene rice phytoalexin. *Biosci. Biotechnol. Biochem.* 56: 1002-1003.

Kodama, O., Suzuki, T., Miyakawa, J., and Akatsuka, T. 1988. Ultraviolet-induced Accumulation of Phytoalexins in Rice Leaves. *Agric. Biol. Chem.* 52: 2469-2473.

Koga, J., Ogawa, N., Yamauchi, T., Kikuchi, N., Ogasawara, N., and Shimura, M. 1997. Functional moiety for the antifungal activity of phytocassane E, a diterpene phytoalexin from rice. *Phytochemistry* 44: 249-253.

Koga, J., Shimura, M., Oshima, K., Ogawa, N., Yamauchi, T., and Ogasawara, N. 1995. Phytocassanes A, B, C, and D, Novel Diterpene Phytoalexins from Rice, *Oryza sativa* L. *Tetrahedron* 51: 7907-7918.

Martin, D., Tholl, D., Gershenzon, J., and Bohlmann, J. 2002. Methyl Jasmonate Induces Traumatic Resin Ducts, Terpenoid Resin Biosynthesis, and Terpenoid Accumulation in Developing Xylem of Norway Spruce Stems. *Plant Physiol.* 129: 1003-1018.

Martin, D. M., Faldt, J., and Bohlmann, J. 2004. Functional Characterization of Nine Norway Spruce TPS genes and Evolution of Gymnosperm Terpene Synthases of the TPS-d Subfamily. *Plant Physiol.* 135: 1908-1927.

Miroux, B., and Walker, J. E. 1996. Over-production of proteins in *Escherichia coli*: mutant hosts that allow synthesis of some membrane proteins and globular proteins at high levels. *J. Mol. Biol.* 260: 289-298.

Mohan, R. S., Yee, N. K. N., Coates, R. M., Ren, Y. Y., Stamenkovic, P., Mendez, I., and West, C. A. 1996. Biosynthesis of cyclic diterpene hydrocarbons in rice cell suspensions: conversion of 9,10-syn-labda-8(17),13-dienyl diphosphate to 9β-pimara-7,15-diene and stemar-13-ene. *Arch. Biochem. Biophys.* 330: 33-47.

Nojiri, H., Sugimora, M., Yamane, H., Nishimura, Y., Yamada, A., Shibuya, N., Kodama, O., Murofushi, N., and Omori, T. 1996. Involvement of Jasmonic Acid in Elicitor-Induced Phytoalexin Production in Suspension-Cultured Rice Cells. *Plant Physiol.* 110: 387-392.

Peters, R. J., Carter, O. A., Zhang, Y., Matthews, B. W., and Croteau, R. B. 2003. Bifunctional Abietadiene Synthase: Mutual Structural Dependence of the Active Sites for Protonation-Initiated and Ionization-Initiated Cyclizations. *Biochemistry* 42: 2700-2707.

Peters, R. J., and Croteau, R. B. 2002. Abietadiene Synthase Catalysis: Conserved Residues Involved in Protonation-Initated Cyclization of Geranylgeranyl Diphosphate to (+)-Copalyl Diphosphate. *Biochemistry* 41: 1836-1842.

Peters, R. J., and Croteau, R. B. 2003. Alternative termination chemistries utilized by monoterpene cyclases: chimeric analysis of bornyl diphosphate, 1,8-cineole, and sabinene synthases. *Arch. Biochem. Biophys.* 417: 203-211.

Peters, R. J., and Croteau, R. B. 2004. Metabolic Engineering of Plant Secondary Metabolism. In *Handbook of Plant Biotechnology: Applications of Plant Biotechnology in Agriculture, the Pharmaceutical Industry, and Other Industries*. (ed. G. Kishore), pp. 609-628. John Wiley & Sons Ltd, London.

Peters, R. J., Flory, J. E., Jetter, R., Ravn, M. M., Lee, H.-J., Coates, R. M., and Croteau, R. B. 2000. Abietadiene Synthase from Grand Fir (*Abies grandis*): Characterization and Mechanism of Action of the "Pseudomature" Recombinant Enzyme. *Biochemistry* 39: 15592-15602.

Peters, R. J., Ravn, M. M., Coates, R. M., and Croteau, R. B. 2001. Bifunctional Abietadiene Synthase: Free Diffusive Transfer of the (+)-Copalyl Diphosphate Intermediate Between Two Distinct Active Sites. *J. Am. Chem. Soc.* 123: 8974-8978.

Prisic, S., Xu, M., Wilderman, P. R., and Peters, R. J. 2004. Rice contains disparate ent-copalyl diphosphate synthases with distinct metabolic functions. *Plant Physiol.* 136: 4228-4236.

Rebers, M., Kaneta, T., Kawaide, H., Yamaguchi, S., Yang, Y. Y., Imai, R., Sekimoto, H., and Kamiya, Y. 1999. Regulation of gibberellin biosynthesis genes during flower and early fruit development of tomato. *Plant J.* 17: 241-250.

Richman, A. S., Gijzen, M., Starratt, A. N., Yang, Z., and Brandle, J. E. 1999. Diterpene synthesis in *Stevia rebaudiana*: recruitment and up-regulation of key enzymes from the gibberellin biosynthetic pathway. *Plant J.* 19: 411-421.

Sakamoto, T., et al. 2004. An Overview of Gibberellin Metabolism Enzyme Genes and Their Related Mutants in Rice. *Plant Physiol.* 134: 1642-1653.

Schepmann, H. G., Pang, J., and Matsuda, S. P. 2001. Cloning and Characterization of *Ginkgo biloba* Levopimaradiene Synthase, Which Catalyzes the First Committed Step in Ginkolide Biosynthesis. *Arch. Biochem. Biophys.* 392: 263-269.

Sekido, H., Endo, T., Suga, R., Kodama, O., Akatsuka, T., Kono, Y., and Takeuchi, S. 1986. Oryzalexin D (3,7-Dihydroxy-(+)-sandaracopimaradiene), a New Phytoalexin Isolated from Blast-infected Rice Leaves. *J. Pesticide Sci.* 11: 369-372.

Silverstone, A. L., Chang, C.-W., Krol, E., and Sun, T.-P. 1997. Developmental regulation of the gibberellin biosynthetic gene GA1 in *Arabidopsis thaliana*. *Plant J.* 12: 9-19.

Smith, M. W., Yamaguchi, S., Ait-Ali, T., and Kamiya, Y. 1998. The first step of gibberellin biosynthesis in pumpkin is catalyzed by at least two copalyl diphosphate synthases encoded by differentially regulated genes. *Plant Physiol.* 118: 1411-1419.

Starks, C. M., Back, K., Chappell, J., and Noel, J. P. 1997. Structural basis for cyclic terpene biosynthesis by tobacco 5-epi-aristolochene synthase. *Science* 277: 1815-1820.

Stofer Vogel, B., Wildung, M. R., Vogel, G., and Croteau, R. 1996. Abietadiene Synthase from Grand Fir (*Abies grandis*). *J. Biol. Chem.* 271: 23262-23268.

Sun, T.-P., and Kamiya, Y. 1994. The *Arabidopsis* GA1 locus encodes the cyclase ent-kaurene synthetase A of gibberellin biosynthesis. *Plant Cell* 6: 1509-1518.

VanEtten, H. D., Mansfield, J. W., Bailey, J. A., and Farmer, E. E. 1994. Two classes of plant antibiotics: phytoalexins versus 'phytoanticipins'. *Plant Cell* 6: 1191-1192.

Whittington, D. A., Wise, M. L., Urbansky, M., Coates, R. M., Croteau, R. B., and Christianson, D. W. 2002. Bornyl diphosphate synthase: structure and strategy for carbocation manipulation by a terpenoid cyclase. *Proc Natl Acad Sci USA.* 99: 15375-15380.

Wickham, K. A., and West, C. A. 1992. Biosynthesis of Rice Phytoalexins: Identification of Putative Diterpene Hydrocarbon Precursors. *Arch. Biochem. Biophys.* 293: 320-332.

Wilderman, P. R., Xu, M., Jin, Y., Coates, R. M., and Peters, R. J. 2004. Identification of syn-pimara-7,15-diene synthase reveals functional clustering of terpene synthases involved in rice phytoalexin/allelochemical biosynthesis. *Plant Physiol.* 135: 2098-2105.

Wildung, M. R., and Croteau, R. B. 1996. A cDNA clone for taxadiene synthase, the diterpene cyclase that catalyzes the committed step of taxol biosynthesis. *J. Biol. Chem.* 271: 9201-9204.

Williams, D. C., McGarvey, D. J., Katahira, E. J., and Croteau, R. 1998. Truncation of Limonene Synthase Preprotein Provides a Fully Active 'Pseudomature' Form of This Monoterpene Cyclase and Reveals the Function of the Amino-Terminal Arginine Pair. *Biochemistry* 37: 12213-12220.

Wise, M. L., Pyun, H.-J., Helms, G., Assink, B., Coates, R. M., and Croteau, R. B. 2001. Stereochemical disposition of the geminal dimethyl groups in the enzymatic cyclization of geranyl diphosphate to (+)-bornyl diphosphate by recombinant (+)-bornyl diphosphate synthase from *Salvia officinalis*. *Tetrahedron* 57: 5327-5334.

Xu, M., Hillwig, M. L., Prisic, S., Coates, R. M., and Peters, R. J. 2004. Functional identification of rice syn-copalyl diphosphate synthase and its role in initiating biosynthesis of diterpenoid phytoalexin/allelopathic natural products. *Plant J.* 39: 309-318.

Yajima, A., Mori, K., and Yabuta, G. 2004. Total synthesis of ent-cassa-12,15-diene, a putative precursor of rice phytoalexins, phytocassanes A-E. *Tetrahedron Lett.* 45: 167-169.

Yamaguchi, S., Saito, T., Abe, H., Yamane, H., Murofushi, N., and Kamiya, Y. 1996. Molecular cloning and characterization of a cDNA encoding the gibberellin biosynthetic enzyme ent-kaurene synthase B from pumpkin (*Cucurbita maxima* L.). *Plant J.* 10: 101-111.

Yamaguchi, S., Sun, T., Kawaide, H., and Kamiya, Y. 1998. The GA2 Locus of *Arabidopsis thaliana* Encodes ent-Kaurene Synthase of Gibberellin Biosynthesis. *Plant Physiol.* 116: 1271-1278.

Yee, N. K. N., and Coates, R. M. 1992. Total synthesis of (+)-9,10-syn- and (+)-9,10-anti-copalol via epoxy trienylsilane cyclizations. *J. Org. Chem.* 57: 4598-4608.

Yu, J., Hu, S., Wang, J., Wong, G. K., Li, S., Liu, B., Deng, Y., Dai, L., Zhou, Y., Zhang, X., et al. 2002. A draft sequence of the rice genome (*Oryza sativa* L. ssp. *indica*). *Science* 296: 79-92.

What is claimed is:

1. A transformed plant comprising a polynucleotide selected from the group consisting of:
   (a) a polynucleotide encoding the polypeptide of SEQ ID NO:7;
   (b) the polynucleotide of SEQ ID NO: 13;
   (c) a polynucleotide having at least 90% sequence identity to the entire coding region of SEQ ID NO: 13; and
   (d) a polynucleotide complementary to the polynucleotide of (a), (b) or (c).

2. A method of making a class II terpene synthase comprising the steps of:
   A) expressing a polynucleotide in a recombinantly engineered cell or ex vivo, wherein the polynucleotide is selected from the group consisting of:
      (a) a polynucleotide encoding the polypeptide of SEQ ID NO:7;
      (b) the polynucleotide of SEQ ID NO: 13;
      (c) a polynucleotide having at least 90% sequence identity to the entire coding region of SEQ ID NO: 13; and
      (d) a polynucleotide complementary to the polynucleotide of (a), (b) or (c); and
   B) purifying the enzyme.

3. A transformed plant comprising a polynucleotide selected from the group consisting of:
   (a) a polynucleotide encoding the polypeptide of SEQ ID NO:7; and
   (b) the polynucleotide of SEQ ID NO: 13.

4. A method of making a class II terpene synthase comprising the steps of:
   A) expressing a polynucleotide in a recombinantly engineered cell or ex vivo, wherein the polynucleotide is selected from the group consisting of:
      (a) a polynucleotide encoding the polypeptide of SEQ ID NO:7; and
      (b) the polynucleotide of SEQ ID NO: 13; and
   B) purifying the enzyme.

* * * * *

SEQUENCE LISTING

<160> NUMBER OF SEQ ID NOS: 23

<210> SEQ ID NO 1
<211> LENGTH: 813
<212> TYPE: PRT
<213> ORGANISM: Poaceae

<400> SEQUENCE: 1

```
Met Pro Tyr Pro His Pro Tyr Pro Trp Gln Ser Ser Arg Arg Arg Arg
1               5                   10                  15

Arg Arg Arg Gly Arg Asp Gly Ala Pro Arg Gln Pro Gln Ala Arg Arg
            20                  25                  30

Val Val Glu Arg Ala Ala Ala Gly Pro Gly His Ala Thr Thr Thr Gln
        35                  40                  45

Gln Pro Asp Asn Val Ser Ser Ala Lys Val Phe Gln Thr Ser Arg Val
    50                  55                  60

Glu Thr Glu Ser Lys Leu Arg Asn Gly Arg Lys Pro Gln Asp Leu Glu
65                  70                  75                  80

Asp Glu His Gln Ala Glu Glu Ala Glu Leu Gln Pro Leu Ile Asp Gln
                85                  90                  95

Val Arg Ala Met Leu Arg Ser Met Asn Asp Gly Asp Thr Ser Ala Ser
            100                 105                 110

Ala Tyr Asp Thr Ala Trp Val Ala Met Val Pro Lys Val Gly Gly Asp
        115                 120                 125

Gly Gly Ala Gln Pro Gln Phe Pro Ala Thr Val Arg Trp Ile Val Asp
    130                 135                 140

His Gln Leu Pro Asp Gly Ser Trp Gly Asp Ser Ala Leu Phe Ser Ala
145                 150                 155                 160

Tyr Asp Arg Met Ile Asn Thr Leu Ala Cys Val Val Ala Leu Thr Lys
                165                 170                 175

Trp Ser Leu Glu Pro Ala Arg Cys Glu Ala Gly Leu Ser Phe Leu His
            180                 185                 190

Glu Asn Met Trp Arg Leu Ala Glu Glu Glu Ala Glu Ser Met Pro Ile
```

```
            195                 200                 205
Gly Phe Glu Ile Ala Phe Pro Ser Leu Ile Gln Thr Ala Arg Asp Leu
    210                 215                 220
Gly Val Asp Phe Pro Tyr Gly His Pro Ala Leu Gln Ser Ile Tyr
225                 230                 235                 240
Pro Arg Asp Met Met His Arg Val Pro Thr Ser Ile Leu His Ser Leu
                245                 250                 255
Glu Gly Met Pro Asp Leu Asp Trp Pro Arg Leu Leu Asn Leu Gln Ser
                260                 265                 270
Cys Asp Gly Ser Phe Leu Phe Ser Pro Ser Ala Thr Ala Tyr Ala Leu
            275                 280                 285
Met Gln Thr Gly Asp Lys Lys Cys Phe Glu Tyr Ile Asp Arg Ile Val
        290                 295                 300
Lys Lys Phe Asn Gly Gly Val Pro Asn Val Tyr Pro Val Asp Leu Phe
305                 310                 315                 320
Glu His Ile Trp Val Asp Arg Leu Glu Arg Leu Gly Ile Ser Arg
                325                 330                 335
Tyr Phe Gln Arg Glu Ile Glu Gln Cys Met Asp Tyr Val Asn Arg His
                340                 345                 350
Trp Thr Glu Asp Gly Ile Cys Trp Ala Arg Lys Ser Asn Val Lys Asp
                355                 360                 365
Val Asp Asp Thr Ala Met Ala Phe Arg Leu Leu Arg Leu His Gly Tyr
        370                 375                 380
Asn Val Ser Pro Ser Val Phe Lys Asn Phe Glu Lys Asp Gly Glu Phe
385                 390                 395                 400
Phe Cys Phe Val Gly Gln Ser Thr Gln Ala Val Thr Gly Met Tyr Asn
                405                 410                 415
Leu Asn Arg Ala Ser Gln Ile Ser Phe Gln Gly Glu Asp Val Leu His
                420                 425                 430
Arg Ala Arg Val Phe Ser Tyr Glu Phe Leu Arg Gln Arg Glu Glu Gln
            435                 440                 445
Gly Met Ile Arg Asp Lys Trp Ile Val Ala Lys Asp Leu Pro Gly Glu
        450                 455                 460
Val Gln Tyr Thr Leu Asp Phe Pro Trp Tyr Ala Ser Leu Pro Arg Val
465                 470                 475                 480
Glu Ala Arg Thr Tyr Leu Asp Gln Tyr Gly Gly Lys Asp Asp Val Trp
                485                 490                 495
Ile Gly Lys Thr Leu Tyr Arg Met Pro Leu Val Asn Asn Asp Thr Tyr
                500                 505                 510
Leu Glu Leu Ala Ile Arg Asp Phe Asn His Cys Gln Ala Leu His Gln
            515                 520                 525
Leu Glu Cys Asn Gly Leu Gln Thr Trp Tyr Lys Asp Asn Cys Leu Asp
        530                 535                 540
Ala Phe Gly Val Glu Pro Gln Asp Val Leu Arg Ser Tyr Phe Leu Ala
545                 550                 555                 560
Ala Ala Cys Ile Phe Glu Pro Ser Arg Ala Ala Glu Arg Leu Ala Trp
                565                 570                 575
Ala Arg Thr Ser Met Ile Ala Asn Ala Ile Ser Thr His Leu Arg Asp
            580                 585                 590
Ile Ser Glu Asp Lys Lys Arg Leu Glu Cys Phe Val His Cys Leu Tyr
        595                 600                 605
Glu Glu Asn Asp Val Ser Trp Leu Lys Arg Asn Pro Asn Asp Val Ile
    610                 615                 620
```

```
Leu Glu Arg Ala Leu Arg Arg Leu Ile Asn Leu Leu Ala Gln Glu Ala
625                 630                 635                 640

Leu Pro Ile His Glu Gly Gln Arg Phe Ile His Ser Leu Leu Ser Leu
            645                 650                 655

Ala Trp Thr Glu Trp Met Leu Gln Lys Ala Asn Lys Glu Glu Asn Lys
            660                 665                 670

Tyr His Lys Cys Ser Gly Ile Glu Pro Gln Tyr Met Val His Asp Arg
            675                 680                 685

Gln Thr Tyr Leu Leu Leu Val Gln Val Ile Glu Ile Cys Ala Gly Arg
            690                 695                 700

Ile Gly Glu Ala Val Ser Met Ile Asn Asn Lys Asp Asn Asp Trp Phe
705                 710                 715                 720

Ile Gln Leu Thr Cys Ala Thr Cys Asp Ser Leu Asn His Arg Met Leu
            725                 730                 735

Leu Ser Gln Asp Thr Met Lys Asn Glu Ala Arg Ile Asn Trp Ile Glu
            740                 745                 750

Lys Glu Ile Glu Leu Asn Met Gln Glu Leu Ala Gln Ser Leu Leu Leu
            755                 760                 765

Arg Cys Asp Glu Lys Thr Ser Asn Lys Lys Thr Lys Lys Thr Leu Trp
            770                 775                 780

Asp Val Leu Arg Ser Leu Tyr Tyr Ala Thr His Ser Pro Gln His Met
785                 790                 795                 800

Ile Asp Arg His Val Ser Arg Val Ile Phe Glu Pro Val
            805                 810

<210> SEQ ID NO 2
<211> LENGTH: 867
<212> TYPE: PRT
<213> ORGANISM: Poaceae

<400> SEQUENCE: 2

Met Ile His Leu His Ser Pro Pro Thr Ala Pro Ala Ala Phe Gly Gly
1               5                   10                  15

Ala Gly Ser Ala Asp Trp Arg Arg Arg Arg Trp Ser Trp Ser Ser
            20                  25                  30

Ser Ser Arg Ala Pro Val Ala Lys Gly Gly His Leu Arg Pro Cys Val
            35                  40                  45

Trp Arg Arg Gly Gly Asp Gly Gly Gly Glu Asp His His Ala Asp
            50                  55                  60

Ser Gly Gly Gly Gly Gly Gly Ala Ala Trp Arg Ala Arg Ala Thr
65                  70                  75                  80

Thr Ala Gly Val Ser Ser Ser Ser Thr Ala Lys Gly Leu Gln Ala
            85                  90                  95

Asn Ile Ile Glu His Glu Thr Pro Arg Ile Thr Lys Trp Pro Asn Glu
            100                 105                 110

Ser Arg Asp Leu Asp Asp His Gln Gln Asn Asn Glu Ala Asp Glu Glu
            115                 120                 125

Ala Asp Asp Glu Leu Gln Pro Leu Val Glu Gln Val Arg Ser Met Leu
            130                 135                 140

Ser Ser Met Glu Asp Gly Ala Ile Thr Ala Ser Ala Tyr Asp Thr Ala
145                 150                 155                 160

Trp Val Ala Leu Val Pro Arg Leu Asp Gly Glu Gly Gly Thr Gln Phe
            165                 170                 175

Pro Ala Ala Val Arg Trp Ile Val Gly Ser Gln Leu Ala Asp Gly Ser
```

-continued

```
            180                 185                 190
Trp Gly Asp Glu Ala Leu Phe Ser Ala Tyr Asp Arg Val Ile Asn Thr
    195                 200                 205
Leu Ala Cys Val Val Ala Leu Thr Arg Trp Ser Leu His His Asp Gln
    210                 215                 220
Cys Lys Gln Gly Leu Gln Phe Leu Asn Leu Asn Leu Trp Arg Leu Ala
225                 230                 235                 240
Glu Glu Glu Pro Asp Thr Met Pro Ile Gly Phe Glu Ile Ala Phe Pro
                245                 250                 255
Ser Leu Val Glu Ala Ala Arg Gly Leu Gly Ile Asp Phe Pro Tyr Asp
            260                 265                 270
His Pro Ala Leu Lys Gly Ile Tyr Ala Asn Arg Glu Leu Lys Leu Lys
        275                 280                 285
Arg Ile Pro Lys Asp Met Met His Ile Val Pro Thr Ser Ile Leu His
    290                 295                 300
Ser Leu Glu Gly Met Pro Gly Leu Asp Trp Gln Arg Leu Leu Lys Leu
305                 310                 315                 320
Gln Cys Ser Asp Gly Ser Phe Leu Phe Ser Pro Ser Ala Thr Ala Tyr
                325                 330                 335
Ala Leu Met Gln Thr Gly Asp Lys Lys Cys Phe Ala Tyr Ile Asp Arg
            340                 345                 350
Ile Ile Lys Lys Phe Asp Gly Val Pro Asn Val Tyr Pro Val Asp
        355                 360                 365
Leu Phe Glu His Ile Trp Val Val Asp Arg Leu Glu Arg Leu Gly Ile
    370                 375                 380
Ser Arg Tyr Phe Gln Arg Glu Ile Glu Gln Asn Met Asp Tyr Val Asn
385                 390                 395                 400
Arg His Trp Thr Glu Asp Gly Ile Cys Trp Ala Arg Asn Ser Asn Val
                405                 410                 415
Lys Glu Val Asp Asp Thr Ala Met Ala Phe Arg Leu Leu Arg Leu His
            420                 425                 430
Gly Tyr Asn Val Ser Pro Ser Val Phe Lys Asn Phe Glu Lys Asp Gly
        435                 440                 445
Glu Phe Phe Cys Phe Val Gly Gln Ser Thr Gln Ala Val Thr Gly Met
    450                 455                 460
Tyr Asn Leu Asn Arg Ala Ser Gln Ile Ser Phe Pro Gly Glu Asp Ile
465                 470                 475                 480
Leu Gln Arg Ala Arg Asn Phe Ser Tyr Glu Phe Leu Arg Glu Arg
                485                 490                 495
Ala Gln Gly Thr Leu His Asp Lys Trp Ile Ile Ser Lys Asp Leu Pro
            500                 505                 510
Gly Glu Val Gln Tyr Thr Leu Asp Phe Pro Trp Tyr Ala Ser Leu Pro
        515                 520                 525
Arg Val Glu Ala Arg Thr Tyr Ile Gly Gln Tyr Gly Gly Asn Asp Asp
    530                 535                 540
Val Trp Ile Gly Lys Thr Leu Tyr Arg Met Pro Ile Val Asn Asn Ala
545                 550                 555                 560
Thr Tyr Leu Glu Leu Ala Lys Gln Asp Phe Asn Arg Cys Gln Ala Leu
                565                 570                 575
His Gln His Glu Leu Gln Gly Leu Gln Lys Trp Phe Ile Glu Asn Gly
            580                 585                 590
Leu Glu Ala Phe Gly Met Thr Pro Glu Asp Val Leu Arg Ala Tyr Phe
        595                 600                 605
```

```
Leu Ala Ala Ala Cys Ile Phe Glu Pro Asn Arg Ala Ser Glu Arg Leu
        610                 615                 620

Ala Trp Ala Arg Val Ser Val Leu Ala Asn Thr Ile Ser Arg His Phe
625                 630                 635                 640

Tyr Ser Asp Met Ser Ser Met Lys Arg Met Glu Arg Phe Met Trp Ser
                645                 650                 655

Ser Leu Tyr Glu Glu Asn Gly Asn Val Leu Gly Leu Glu Gly Tyr Ala
            660                 665                 670

Lys Asp Gly Ile Leu Ala Arg Thr Leu Cys Gln Leu Ile Asp Leu Leu
        675                 680                 685

Ser Gln Glu Thr Pro Pro Val Arg Glu Gly Gln Lys Cys Ile His Asn
690                 695                 700

Leu Ile Arg Cys Ala Trp Ile Glu Trp Met Met Gln Gln Ile Asn Met
705                 710                 715                 720

Lys Asp Gly Arg Tyr Asp Lys Gly Arg Val Met His Pro Gly Ser Cys
                725                 730                 735

Thr Val His Asn Lys Glu Thr Cys Leu Leu Ile Ala Gln Ile Val Glu
            740                 745                 750

Ile Cys Ala Gly Arg Ile Glu Glu Ala Ala Ser Met Ile Asn Asn Thr
        755                 760                 765

Glu Gly Ser Trp Phe Ile Gln Leu Ala Ser Ser Ile Cys Asp Ser Leu
770                 775                 780

His Ala Lys Met Leu Leu Ser Gln Asp Thr Lys Lys Asn Glu Thr Thr
785                 790                 795                 800

Ile Asn Gln Ile Asp Lys Glu Ile Glu Leu Gly Met Gln Glu Leu Ala
                805                 810                 815

Gln Tyr Leu Leu Pro Arg Val Asp Asp Arg Ile Asn Asn Lys Thr
            820                 825                 830

Lys Gln Thr Phe Leu Ser Ile Val Lys Ser Cys Tyr Tyr Ala Ala Asn
        835                 840                 845

Cys Ser Pro His Met Leu Asp Gln His Ile Ser Glu Val Ile Phe Glu
    850                 855                 860

Gln Val Ile
865

<210> SEQ ID NO 3
<211> LENGTH: 800
<212> TYPE: PRT
<213> ORGANISM: Poaceae

<400> SEQUENCE: 3

Met Gln Met Gln Val Leu Thr Ala Ala Ser Ser Leu Pro Arg Ala Thr
1               5                   10                  15

Leu Leu Arg Pro Ala Ala Glu Pro Trp Arg Gln Ser Phe Leu Gln
            20                  25                  30

Leu Gln Ala Arg Pro Ile Gln Arg Pro Gly Ile Met Leu His Cys Lys
        35                  40                  45

Ala Gln Leu Gln Gly Gln Thr Arg Glu Arg Arg Gln Leu Asp Asp
    50                  55                  60

Asp Glu His Ala Arg Pro Pro Gln Gly Gly Asp Asp Val Ala Ala
65                  70                  75                  80

Ser Thr Ser Glu Leu Pro Tyr Met Ile Glu Ser Ile Lys Ser Lys Leu
                85                  90                  95

Arg Ala Ala Arg Asn Ser Leu Gly Glu Thr Thr Val Ser Ala Tyr Asp
```

-continued

```
                100                 105                 110
Thr Ala Trp Ile Ala Leu Val Asn Arg Leu Asp Gly Gly Glu Arg
            115                 120                 125
Ser Pro Gln Phe Pro Glu Ala Ile Asp Trp Ile Ala Arg Asn Gln Leu
    130                 135                 140
Pro Asp Gly Ser Trp Gly Asp Ala Gly Met Phe Ile Val Gln Asp Arg
145                 150                 155                 160
Leu Ile Asn Thr Leu Gly Cys Val Val Ala Leu Ala Thr Trp Gly Val
                165                 170                 175
His Glu Glu Gln Arg Ala Arg Gly Leu Ala Tyr Ile Gln Asp Asn Leu
            180                 185                 190
Trp Arg Leu Gly Glu Asp Asp Glu Trp Met Met Val Gly Phe Glu
        195                 200                 205
Ile Thr Phe Pro Val Leu Leu Glu Lys Ala Lys Asn Leu Gly Leu Asp
    210                 215                 220
Ile Asn Tyr Asp Asp Pro Ala Leu Gln Asp Ile Tyr Ala Lys Arg Gln
225                 230                 235                 240
Leu Lys Leu Ala Lys Ile Pro Arg Glu Ala Leu His Ala Arg Pro Thr
                245                 250                 255
Thr Leu Leu His Ser Leu Glu Gly Met Glu Asn Leu Asp Trp Glu Arg
            260                 265                 270
Leu Leu Gln Phe Lys Cys Pro Ala Gly Ser Leu His Ser Ser Pro Ala
        275                 280                 285
Ala Ser Ala Tyr Ala Leu Ser Glu Thr Gly Asp Lys Glu Leu Leu Glu
    290                 295                 300
Tyr Leu Glu Thr Ala Ile Asn Asn Phe Asp Gly Gly Ala Pro Cys Thr
305                 310                 315                 320
Tyr Pro Val Asp Asn Phe Asp Arg Leu Trp Ser Val Asp Arg Leu Arg
                325                 330                 335
Arg Leu Gly Ile Ser Arg Tyr Phe Thr Ser Glu Ile Glu Glu Tyr Leu
            340                 345                 350
Glu Tyr Ala Tyr Arg His Leu Ser Pro Asp Gly Met Ser Tyr Gly Gly
        355                 360                 365
Leu Cys Pro Val Lys Asp Ile Asp Asp Thr Ala Met Ala Phe Arg Leu
    370                 375                 380
Leu Arg Leu His Gly Tyr Asn Val Ser Ser Ser Val Phe Asn His Phe
385                 390                 395                 400
Glu Lys Asp Gly Glu Tyr Phe Cys Phe Ala Gly Gln Ser Ser Gln Ser
                405                 410                 415
Leu Thr Ala Met Tyr Asn Ser Tyr Arg Ala Ser Gln Ile Val Phe Pro
            420                 425                 430
Gly Asp Asp Asp Gly Leu Glu Gln Leu Arg Ala Tyr Cys Arg Ala Phe
        435                 440                 445
Leu Glu Glu Arg Arg Ala Thr Gly Asn Leu Arg Asp Lys Trp Val Ile
    450                 455                 460
Ala Asn Gly Leu Pro Ser Glu Val Glu Tyr Ala Leu Asp Phe Pro Trp
465                 470                 475                 480
Lys Ala Ser Leu Pro Arg Val Glu Thr Arg Val Tyr Leu Glu Gln Tyr
                485                 490                 495
Gly Ala Ser Glu Asp Ala Trp Ile Gly Lys Gly Leu Tyr Arg Met Thr
            500                 505                 510
Leu Val Asn Asn Asp Leu Tyr Leu Glu Ala Ala Lys Ala Asp Phe Thr
        515                 520                 525
```

```
Asn Phe Gln Arg Leu Ser Arg Leu Glu Trp Leu Ser Leu Lys Arg Trp
        530                 535                 540

Tyr Ile Arg Asn Asn Leu Gln Ala His Gly Val Thr Glu Gln Ser Val
545                 550                 555                 560

Leu Arg Ala Tyr Phe Leu Ala Ala Asn Ile Phe Glu Pro Asn Arg
            565                 570                 575

Ala Ala Glu Arg Leu Gly Trp Ala Arg Thr Ala Ile Leu Ala Glu Ala
                580                 585                 590

Ile Ala Ser His Leu Arg Gln Tyr Ser Ala Asn Gly Ala Ala Asp Gly
            595                 600                 605

Met Thr Glu Arg Leu Ile Ser Gly Leu Ala Ser His Asp Trp Asp Trp
        610                 615                 620

Arg Glu Ser Asn Asp Ser Ala Ala Arg Ser Leu Tyr Ala Leu Asp
625                 630                 635                 640

Glu Leu Ile Asp Leu His Ala Phe Gly Asn Ala Ser Asp Ser Leu Arg
                645                 650                 655

Glu Ala Trp Lys Gln Trp Leu Met Ser Trp Thr Asn Glu Ser Gln Gly
            660                 665                 670

Ser Thr Gly Gly Asp Thr Ala Leu Leu Leu Val Arg Thr Ile Glu Ile
        675                 680                 685

Cys Ser Gly Arg His Gly Ser Ala Glu Gln Ser Leu Lys Asn Ser Glu
        690                 695                 700

Asp Tyr Ala Arg Leu Glu Gln Ile Ala Ser Ser Met Cys Ser Lys Leu
705                 710                 715                 720

Ala Thr Lys Ile Leu Ala Gln Asn Gly Gly Ser Met Asp Asn Val Glu
            725                 730                 735

Gly Ile Asp Gln Glu Val Asp Val Glu Met Lys Glu Leu Ile Gln Arg
                740                 745                 750

Val Tyr Gly Ser Ser Asn Asp Val Ser Ser Val Thr Arg Gln Thr
            755                 760                 765

Phe Leu Asp Val Val Lys Ser Phe Cys Tyr Val Ala His Cys Ser Pro
770                 775                 780

Glu Thr Ile Asp Gly His Ile Ser Lys Val Leu Phe Glu Asp Val Asn
785                 790                 795                 800

<210> SEQ ID NO 4
<211> LENGTH: 767
<212> TYPE: PRT
<213> ORGANISM: Poaceae

<400> SEQUENCE: 4

Met Pro Val Phe Thr Ala Ser Phe Gln Cys Val Thr Leu Phe Gly Gln
1               5                   10                  15

Pro Ala Ser Ala Ala Asp Ala Gln Pro Leu Leu Gln Gly Gln Arg Pro
            20                  25                  30

Phe Leu His Leu His Ala Arg Arg Arg Pro Cys Gly Pro Met Leu
            35                  40                  45

Ile Ser Lys Ser Pro Pro Tyr Pro Ala Ser Glu Glu Thr Arg Glu Trp
        50                  55                  60

Glu Ala Glu Gly Gln His Glu His Thr Asp Glu Leu Arg Glu Thr Thr
65                  70                  75                  80

Thr Thr Met Ile Asp Gly Ile Arg Thr Ala Leu Arg Ser Ile Gly Glu
                85                  90                  95

Gly Glu Ile Ser Ile Ser Ala Tyr Asp Thr Ser Leu Val Ala Leu Leu
```

-continued

```
                100                 105                 110
Lys Arg Leu Asp Gly Gly Asp Gly Pro Gln Phe Pro Ser Thr Ile Asp
                115                 120                 125
Trp Ile Val Gln Asn Gln Leu Pro Asp Gly Ser Trp Gly Asp Ala Ser
130                 135                 140
Phe Phe Met Met Gly Asp Arg Ile Met Ser Thr Leu Ala Cys Val Val
145                 150                 155                 160
Ala Leu Lys Ser Trp Asn Ile His Thr Asp Lys Cys Glu Arg Gly Leu
                165                 170                 175
Leu Phe Ile Gln Glu Asn Met Trp Arg Leu Ala His Glu Glu Glu Asp
                180                 185                 190
Trp Met Leu Val Gly Phe Glu Ile Ala Leu Pro Ser Leu Leu Asp Met
                195                 200                 205
Ala Lys Asp Leu Asp Leu Asp Ile Pro Tyr Asp Glu Pro Ala Leu Lys
                210                 215                 220
Ala Ile Tyr Ala Glu Arg Glu Arg Lys Leu Ala Lys Ile Pro Arg Asp
225                 230                 235                 240
Val Leu His Ala Met Pro Thr Thr Leu Leu His Ser Leu Glu Gly Met
                245                 250                 255
Val Asp Leu Asp Trp Glu Lys Leu Leu Lys Leu Arg Cys Leu Asp Gly
                260                 265                 270
Ser Phe His Cys Ser Pro Ala Ser Thr Ala Thr Ala Phe Gln Gln Thr
                275                 280                 285
Gly Asp Gln Lys Cys Phe Glu Tyr Leu Asp Gly Ile Val Lys Lys Phe
                290                 295                 300
Asn Gly Gly Val Pro Cys Ile Tyr Pro Leu Asp Val Tyr Glu Arg Leu
305                 310                 315                 320
Trp Ala Val Asp Arg Leu Thr Arg Leu Gly Ile Ser Arg His Phe Thr
                325                 330                 335
Ser Glu Ile Glu Asp Cys Leu Asp Tyr Ile Phe Arg Asn Trp Thr Pro
                340                 345                 350
Asp Gly Leu Ala His Thr Lys Asn Cys Pro Val Lys Asp Ile Asp Asp
                355                 360                 365
Thr Ala Met Gly Phe Arg Leu Leu Arg Leu Tyr Gly Tyr Gln Val Asp
                370                 375                 380
Pro Cys Val Leu Lys Lys Phe Glu Lys Asp Gly Lys Phe Phe Cys Leu
385                 390                 395                 400
His Gly Glu Ser Asn Pro Ser Ser Val Thr Pro Met Tyr Asn Thr Tyr
                405                 410                 415
Arg Ala Ser Gln Leu Lys Phe Pro Gly Asp Asp Gly Val Leu Gly Arg
                420                 425                 430
Ala Glu Val Phe Cys Arg Ser Phe Leu Gln Asp Arg Arg Gly Ser Asn
                435                 440                 445
Arg Met Lys Asp Lys Trp Ala Ile Ala Lys Asp Ile Pro Gly Glu Val
                450                 455                 460
Glu Tyr Ala Met Asp Tyr Pro Trp Lys Ala Ser Leu Pro Arg Ile Glu
465                 470                 475                 480
Thr Arg Leu Tyr Leu Asp Gln Tyr Gly Gly Ser Gly Asp Val Trp Ile
                485                 490                 495
Gly Lys Val Leu His Arg Met Thr Leu Phe Cys Asn Asp Leu Tyr Leu
                500                 505                 510
Lys Ala Ala Lys Ala Asp Phe Ser Asn Phe Gln Lys Glu Cys Arg Val
                515                 520                 525
```

-continued

```
Glu Leu Asn Gly Leu Arg Arg Trp Tyr Leu Arg Ser Asn Leu Glu Arg
    530                 535                 540

Phe Gly Gly Thr Asp Pro Gln Thr Thr Leu Met Thr Ser Tyr Phe Leu
545                 550                 555                 560

Ala Ser Ala Asn Ile Phe Glu Pro Asn Arg Ala Ala Glu Arg Leu Gly
                565                 570                 575

Trp Ala Arg Val Ala Leu Leu Ala Asp Ala Val Ser Ser His Phe Arg
            580                 585                 590

Arg Ile Gly Gly Pro Lys Asn Leu Thr Ser Asn Leu Glu Glu Leu Ile
        595                 600                 605

Ser Leu Val Pro Phe Asp Asp Ala Tyr Ser Gly Ser Leu Arg Glu Ala
    610                 615                 620

Trp Lys Gln Trp Leu Met Ala Trp Thr Ala Lys Glu Ser Ser Gln Glu
625                 630                 635                 640

Ser Ile Glu Gly Asp Thr Ala Ile Leu Leu Val Arg Ala Ile Glu Ile
                645                 650                 655

Phe Gly Gly Arg His Val Leu Thr Gly Gln Arg Pro Asp Leu Trp Glu
            660                 665                 670

Tyr Ser Gln Leu Glu Gln Leu Thr Ser Ser Ile Cys Arg Lys Leu Tyr
        675                 680                 685

Arg Arg Val Leu Ala Gln Glu Asn Gly Lys Ser Thr Glu Lys Val Glu
    690                 695                 700

Glu Ile Asp Gln Gln Leu Asp Leu Glu Met Gln Glu Leu Thr Arg Arg
705                 710                 715                 720

Val Leu Gln Gly Cys Ser Ala Ile Asn Arg Leu Thr Arg Glu Thr Phe
                725                 730                 735

Leu His Val Val Lys Ser Phe Cys Tyr Val Ala Tyr Cys Ser Pro Glu
            740                 745                 750

Thr Ile Asp Asn His Ile Asp Lys Val Ile Phe Gln Asp Val Ile
        755                 760                 765

<210> SEQ ID NO 5
<211> LENGTH: 867
<212> TYPE: PRT
<213> ORGANISM: Poaceae

<400> SEQUENCE: 5

Met Ile His Leu His Ser Pro Pro Thr Ala Pro Ala Ala Phe Gly Gly
1               5                   10                  15

Ala Gly Ser Ala Asp Trp Arg Arg Arg Arg Trp Ser Trp Ser Ser
            20                  25                  30

Ser Ser Arg Ala Pro Val Ala Lys Gly Gly His Leu Arg Pro Cys Val
        35                  40                  45

Trp Arg Arg Gly Gly Asp Asp Gly Gly Glu Asp His His Ala Asp
    50                  55                  60

Ser Gly Gly Gly Gly Gly Gly Ala Ala Trp Arg Ala Arg Ala Thr
65                  70                  75                  80

Thr Ala Gly Val Ser Ser Ser Ser Thr Ala Lys Gly Leu Gln Ala
                85                  90                  95

Asn Ile Ile Glu His Glu Thr Pro Arg Ile Thr Lys Trp Pro Asn Glu
            100                 105                 110

Ser Arg Asp Leu Asp Asp His Gln Gln Asn Asn Glu Ala Asp Glu Glu
        115                 120                 125

Ala Asp Asp Glu Leu Gln Pro Leu Val Glu Gln Val Arg Ser Met Leu
```

-continued

```
            130                 135                 140
Ser Ser Met Glu Asp Gly Ala Ile Thr Ala Ser Ala Tyr Asp Thr Ala
145                 150                 155                 160

Trp Val Ala Leu Val Pro Arg Leu Asp Gly Glu Gly Thr Gln Phe
                165                 170                 175

Pro Ala Ala Val Arg Trp Ile Val Gly Ser Gln Leu Ala Asp Gly Ser
                180                 185                 190

Trp Gly Asp Glu Ala Leu Phe Ser Ala Tyr Asp Arg Val Ile Asn Thr
                195                 200                 205

Leu Ala Cys Val Val Ala Leu Thr Arg Trp Ser Leu His His Asp Gln
210                 215                 220

Cys Lys Gln Gly Leu Gln Phe Leu Asn Leu Asn Leu Trp Arg Leu Ala
225                 230                 235                 240

Glu Glu Glu Pro Asp Thr Met Pro Ile Gly Phe Glu Ile Ala Phe Pro
                245                 250                 255

Ser Leu Val Glu Ala Ala Arg Gly Leu Gly Ile Asp Phe Pro Tyr Asp
                260                 265                 270

His Pro Ala Leu Lys Gly Ile Tyr Ala Asn Arg Glu Leu Lys Leu Lys
                275                 280                 285

Arg Ile Pro Lys Asp Met Met His Ile Val Pro Thr Ser Ile Leu His
                290                 295                 300

Ser Leu Glu Gly Met Pro Gly Leu Asp Trp Gln Arg Leu Leu Lys Leu
305                 310                 315                 320

Gln Cys Ser Asp Gly Ser Phe Leu Phe Ser Pro Ser Ala Thr Ala Tyr
                325                 330                 335

Ala Leu Met Gln Thr Gly Asp Lys Lys Cys Phe Ala Tyr Ile Asp Arg
                340                 345                 350

Ile Ile Lys Lys Phe Asp Gly Val Pro Asn Val Tyr Pro Val Asp
                355                 360                 365

Leu Phe Glu His Ile Trp Val Val Asp Arg Leu Glu Arg Leu Gly Ile
                370                 375                 380

Ser Arg Tyr Phe Gln Arg Glu Ile Glu Gln Asn Met Asp Tyr Val Asn
385                 390                 395                 400

Arg His Trp Thr Glu Asp Gly Ile Cys Trp Ala Arg Asn Ser Asn Val
                405                 410                 415

Lys Glu Val Asp Asp Thr Ala Met Ala Phe Arg Leu Leu Arg Leu His
                420                 425                 430

Gly Tyr Asn Val Ser Pro Ser Val Phe Lys Asn Phe Glu Lys Asp Gly
                435                 440                 445

Glu Phe Phe Cys Phe Val Gly Gln Ser Thr Gln Ala Val Thr Gly Met
                450                 455                 460

Tyr Asn Leu Asn Arg Ala Ser Gln Ile Ser Phe Pro Gly Glu Asp Ile
465                 470                 475                 480

Leu Gln Arg Ala Arg Asn Phe Ser Tyr Glu Phe Leu Arg Glu Arg
                485                 490                 495

Ala Gln Gly Thr Leu His Asp Lys Trp Ile Ile Ser Lys Asp Leu Pro
                500                 505                 510

Gly Glu Val Gln Tyr Thr Leu Asp Phe Pro Trp Tyr Ala Ser Leu Pro
                515                 520                 525

Arg Val Glu Ala Arg Thr Tyr Ile Gly Gln Tyr Gly Gly Asn Asp Asp
                530                 535                 540

Val Trp Ile Gly Lys Thr Leu Tyr Arg Met Pro Ile Val Asn Asn Ala
545                 550                 555                 560
```

```
Thr Tyr Leu Glu Leu Ala Lys Gln Asp Phe Asn Arg Cys Gln Ala Leu
            565                 570                 575

His Gln His Glu Leu Gln Gly Leu Gln Lys Trp Phe Ile Glu Asn Gly
            580                 585                 590

Leu Glu Ala Phe Gly Met Thr Pro Glu Asp Val Leu Arg Ala Tyr Phe
            595                 600                 605

Leu Ala Ala Ala Cys Ile Phe Glu Pro Asn Arg Ala Ser Glu Arg Leu
            610                 615                 620

Ala Trp Ala Arg Val Ser Val Leu Ala Asn Thr Ile Ser Arg His Phe
625                 630                 635                 640

Tyr Ser Asp Met Ser Ser Met Lys Arg Met Glu Arg Phe Met Trp Ser
            645                 650                 655

Ser Leu Tyr Glu Glu Asn Gly Asn Val Leu Gly Leu Glu Gly Tyr Ala
            660                 665                 670

Lys Asp Gly Ile Leu Ala Arg Thr Leu Cys Gln Leu Ile Asp Leu Leu
            675                 680                 685

Ser Gln Glu Thr Pro Pro Val Arg Glu Gly Gln Lys Cys Ile His Asn
            690                 695                 700

Leu Ile Arg Cys Ala Trp Ile Glu Trp Met Met Gln Gln Ile Asn Met
705                 710                 715                 720

Lys Asp Gly Arg Tyr Asp Lys Gly Arg Val Met His Pro Gly Ser Cys
            725                 730                 735

Thr Val His Asn Lys Glu Thr Cys Leu Leu Ile Ala Gln Ile Val Glu
            740                 745                 750

Ile Cys Ala Gly Arg Ile Glu Glu Ala Ala Ser Met Ile Asn Asn Thr
            755                 760                 765

Glu Gly Ser Trp Phe Ile Gln Leu Ala Ser Ser Ile Cys Asp Ser Leu
            770                 775                 780

His Ala Lys Met Leu Leu Ser Gln Asp Thr Lys Lys Asn Glu Thr Thr
785                 790                 795                 800

Ile Asn Gln Ile Asp Lys Glu Ile Glu Leu Gly Met Gln Glu Leu Ala
            805                 810                 815

Gln Tyr Leu Leu Pro Arg Val Asp Asp Arg Arg Ile Asn Asn Lys Thr
            820                 825                 830

Lys Gln Thr Phe Leu Ser Ile Val Lys Ser Cys Tyr Tyr Ala Ala Asn
            835                 840                 845

Cys Ser Pro His Met Leu Asp Gln His Ile Ser Glu Val Ile Phe Glu
850                 855                 860

Gln Val Ile
865

<210> SEQ ID NO 6
<211> LENGTH: 800
<212> TYPE: PRT
<213> ORGANISM: Poaceae

<400> SEQUENCE: 6

Met Gln Met Gln Val Leu Thr Ala Ala Ser Ser Leu Pro Arg Ala Thr
1               5                   10                  15

Leu Leu Arg Pro Ala Ala Ala Glu Pro Trp Arg Gln Ser Phe Leu Gln
            20                  25                  30

Leu Gln Ala Arg Pro Ile Gln Arg Pro Gly Ile Met Leu His Cys Lys
            35                  40                  45

Ala Gln Leu Gln Gly Gln Glu Thr Arg Glu Arg Arg Gln Leu Asp Asp
```

-continued

```
                50                  55                  60
Asp Glu His Ala Arg Pro Pro Gln Gly Gly Asp Asp Val Ala Ala
 65                  70                  75                  80
Ser Thr Ser Glu Leu Pro Tyr Met Ile Glu Ser Ile Lys Ser Lys Leu
                 85                  90                  95
Arg Ala Ala Arg Asn Ser Leu Gly Thr Thr Val Ser Ala Tyr Asp
                100                 105                 110
Thr Ala Trp Ile Ala Leu Val Asn Arg Leu Asp Gly Gly Glu Arg
                115                 120                 125
Ser Pro Gln Phe Pro Glu Ala Ile Asp Trp Ile Ala Arg Asn Gln Leu
                130                 135                 140
Pro Asp Gly Ser Trp Gly Asp Ala Gly Met Phe Ile Val Gln Asp Arg
145                 150                 155                 160
Leu Ile Asn Thr Leu Gly Cys Val Val Ala Leu Ala Thr Trp Gly Val
                165                 170                 175
His Glu Glu Gln Arg Ala Arg Gly Leu Ala Tyr Ile Gln Asp Asn Leu
                180                 185                 190
Trp Arg Leu Gly Glu Asp Asp Glu Trp Met Met Val Gly Phe Glu
                195                 200                 205
Ile Thr Phe Pro Val Leu Leu Glu Lys Ala Lys Asn Leu Gly Leu Asp
                210                 215                 220
Ile Asn Tyr Asp Asp Pro Ala Leu Gln Asp Ile Tyr Ala Lys Arg Gln
225                 230                 235                 240
Leu Lys Leu Ala Lys Ile Pro Arg Glu Ala Leu His Ala Arg Pro Thr
                245                 250                 255
Thr Leu Leu His Ser Leu Glu Gly Met Glu Asn Leu Asp Trp Glu Arg
                260                 265                 270
Leu Leu Gln Phe Lys Cys Pro Ala Gly Ser Leu His Ser Ser Pro Ala
                275                 280                 285
Ala Ser Ala Tyr Ala Leu Ser Glu Thr Gly Asp Lys Glu Leu Leu Glu
                290                 295                 300
Tyr Leu Glu Thr Ala Ile Asn Asn Phe Asp Gly Gly Ala Pro Cys Thr
305                 310                 315                 320
Tyr Pro Val Asp Asn Phe Asp Arg Leu Trp Ser Val Asp Arg Leu Arg
                325                 330                 335
Arg Leu Gly Ile Ser Arg Tyr Phe Thr Ser Glu Ile Glu Glu Tyr Leu
                340                 345                 350
Glu Tyr Ala Tyr Arg His Leu Ser Pro Asp Gly Met Ser Tyr Gly Gly
                355                 360                 365
Leu Cys Pro Val Lys Asp Ile Asp Asp Thr Ala Met Ala Phe Arg Leu
                370                 375                 380
Leu Arg Leu His Gly Tyr Asn Val Ser Ser Ser Val Phe Asn His Phe
385                 390                 395                 400
Glu Lys Asp Gly Glu Tyr Phe Cys Phe Ala Gly Gln Ser Ser Gln Ser
                405                 410                 415
Leu Thr Ala Met Tyr Asn Ser Tyr Arg Ala Ser Gln Ile Val Phe Pro
                420                 425                 430
Gly Asp Asp Asp Gly Leu Glu Gln Leu Arg Ala Tyr Cys Arg Ala Phe
                435                 440                 445
Leu Glu Glu Arg Arg Ala Thr Gly Asn Leu Arg Asp Lys Trp Val Ile
                450                 455                 460
Ala Asn Gly Leu Pro Ser Glu Val Glu Tyr Ala Leu Asp Phe Pro Trp
465                 470                 475                 480
```

-continued

Lys Ala Ser Leu Pro Arg Val Glu Thr Arg Val Tyr Leu Glu Gln Tyr
                485                 490                 495

Gly Ala Ser Glu Asp Ala Trp Ile Gly Lys Gly Leu Tyr Arg Met Thr
            500                 505                 510

Leu Val Asn Asn Asp Leu Tyr Leu Glu Ala Ala Lys Ala Asp Phe Thr
            515                 520                 525

Asn Phe Gln Arg Leu Ser Arg Leu Glu Trp Leu Ser Leu Lys Arg Trp
530                 535                 540

Tyr Ile Arg Asn Asn Leu Gln Ala His Gly Val Thr Glu Gln Ser Val
545                 550                 555                 560

Leu Arg Ala Tyr Phe Leu Ala Ala Asn Ile Phe Glu Pro Asn Arg
                565                 570                 575

Ala Ala Glu Arg Leu Gly Trp Ala Arg Thr Ala Ile Leu Ala Glu Ala
                580                 585                 590

Ile Ala Ser His Leu Arg Gln Tyr Ser Ala Asn Gly Ala Ala Asp Gly
                595                 600                 605

Met Thr Glu Arg Leu Ile Ser Gly Leu Ala Ser His Asp Trp Asp Trp
610                 615                 620

Arg Glu Ser Asn Asp Ser Ala Ala Arg Ser Leu Leu Tyr Ala Leu Asp
625                 630                 635                 640

Glu Leu Ile Asp Leu His Ala Phe Gly Asn Ala Ser Asp Ser Leu Arg
                645                 650                 655

Glu Ala Trp Lys Gln Trp Leu Met Ser Trp Thr Asn Glu Ser Gln Gly
                660                 665                 670

Ser Thr Gly Gly Asp Thr Ala Leu Leu Leu Val Arg Thr Ile Glu Ile
                675                 680                 685

Cys Ser Gly Arg His Gly Ser Ala Glu Gln Ser Leu Lys Asn Ser Glu
                690                 695                 700

Asp Tyr Ala Arg Leu Glu Gln Ile Ala Ser Ser Met Cys Ser Lys Leu
705                 710                 715                 720

Ala Thr Lys Ile Leu Ala Gln Asn Gly Gly Ser Met Asp Asn Val Glu
                725                 730                 735

Gly Ile Asp Gln Glu Val Asp Val Glu Met Lys Glu Leu Ile Gln Arg
                740                 745                 750

Val Tyr Gly Ser Ser Asn Asp Val Ser Ser Val Thr Arg Gln Thr
                755                 760                 765

Phe Leu Asp Val Val Lys Ser Phe Cys Tyr Val Ala His Cys Ser Pro
                770                 775                 780

Glu Thr Ile Asp Gly His Ile Ser Lys Val Leu Phe Glu Asp Val Asn
785                 790                 795                 800

<210> SEQ ID NO 7
<211> LENGTH: 767
<212> TYPE: PRT
<213> ORGANISM: Poaceae

<400> SEQUENCE: 7

Met Pro Val Phe Thr Ala Ser Phe Gln Cys Val Thr Leu Phe Gly Gln
1               5                   10                  15

Pro Ala Ser Ala Ala Asp Ala Gln Pro Leu Leu Gln Gly Gln Arg Pro
                20                  25                  30

Phe Leu His Leu His Ala Arg Arg Arg Pro Cys Gly Pro Met Leu
            35                  40                  45

Ile Ser Lys Ser Pro Pro Tyr Pro Ala Ser Glu Glu Thr Arg Glu Trp

-continued

```
            50                  55                  60
Glu Ala Glu Gly Gln His Glu His Thr Asp Leu Arg Glu Thr Thr
65                  70                  75                  80

Thr Thr Met Ile Asp Gly Ile Arg Thr Ala Leu Arg Ser Ile Gly Glu
                85                  90                  95

Gly Glu Ile Ser Ile Ser Ala Tyr Asp Thr Ser Leu Val Ala Leu Leu
                100                 105                 110

Lys Arg Leu Asp Gly Asp Gly Pro Gln Phe Pro Ser Thr Ile Asp
        115                 120                 125

Trp Ile Val Gln Asn Gln Leu Pro Asp Gly Ser Trp Gly Asp Ala Ser
        130                 135                 140

Phe Phe Met Met Gly Asp Arg Ile Met Ser Thr Leu Ala Cys Val Val
145                 150                 155                 160

Ala Leu Lys Ser Trp Asn Ile His Thr Asp Lys Cys Glu Arg Gly Leu
                165                 170                 175

Leu Phe Ile Gln Glu Asn Met Trp Arg Leu Ala His Glu Glu Asp
        180                 185                 190

Trp Met Leu Val Gly Phe Glu Ile Ala Leu Pro Ser Leu Leu Asp Met
        195                 200                 205

Ala Lys Asp Leu Asp Leu Asp Ile Pro Tyr Asp Glu Pro Ala Leu Lys
        210                 215                 220

Ala Ile Tyr Ala Glu Arg Glu Arg Lys Leu Ala Lys Ile Pro Arg Asp
225                 230                 235                 240

Val Leu His Ala Met Pro Thr Thr Leu Leu His Ser Leu Glu Gly Met
                245                 250                 255

Val Asp Leu Asp Trp Glu Lys Leu Leu Lys Leu Arg Cys Leu Asp Gly
        260                 265                 270

Ser Phe His Cys Ser Pro Ala Ser Thr Ala Thr Ala Phe Gln Gln Thr
        275                 280                 285

Gly Asp Gln Lys Cys Phe Glu Tyr Leu Asp Gly Ile Val Lys Lys Phe
        290                 295                 300

Asn Gly Gly Val Pro Cys Ile Tyr Pro Leu Asp Val Tyr Glu Arg Leu
305                 310                 315                 320

Trp Ala Val Asp Arg Leu Thr Arg Leu Gly Ile Ser Arg His Phe Thr
                325                 330                 335

Ser Glu Ile Glu Asp Cys Leu Asp Tyr Ile Phe Arg Asn Trp Thr Pro
                340                 345                 350

Asp Gly Leu Ala His Thr Lys Asn Cys Pro Val Lys Asp Ile Asp Asp
                355                 360                 365

Thr Ala Met Gly Phe Arg Leu Leu Arg Leu Tyr Gly Tyr Gln Val Asp
        370                 375                 380

Pro Cys Val Leu Lys Lys Phe Glu Lys Asp Gly Lys Phe Phe Cys Leu
385                 390                 395                 400

His Gly Glu Ser Asn Pro Ser Ser Val Thr Pro Met Tyr Asn Thr Tyr
                405                 410                 415

Arg Ala Ser Gln Leu Lys Phe Pro Gly Asp Asp Gly Val Leu Gly Arg
        420                 425                 430

Ala Glu Val Phe Cys Arg Ser Phe Leu Gln Asp Arg Arg Gly Ser Asn
        435                 440                 445

Arg Met Lys Asp Lys Trp Ala Ile Ala Lys Asp Ile Pro Gly Glu Val
        450                 455                 460

Glu Tyr Ala Met Asp Tyr Pro Trp Lys Ala Ser Leu Pro Arg Ile Glu
465                 470                 475                 480
```

```
Thr Arg Leu Tyr Leu Asp Gln Tyr Gly Gly Ser Gly Asp Val Trp Ile
            485                 490                 495

Gly Lys Val Leu His Arg Met Thr Leu Phe Cys Asn Asp Leu Tyr Leu
        500                 505                 510

Lys Ala Ala Lys Ala Asp Phe Ser Asn Phe Gln Lys Glu Cys Arg Val
    515                 520                 525

Glu Leu Asn Gly Leu Arg Arg Trp Tyr Leu Arg Ser Asn Leu Glu Arg
530                 535                 540

Phe Gly Gly Thr Asp Pro Gln Thr Thr Leu Met Thr Ser Tyr Phe Leu
545                 550                 555                 560

Ala Ser Ala Asn Ile Phe Glu Pro Asn Arg Ala Ala Glu Arg Leu Gly
            565                 570                 575

Trp Ala Arg Val Ala Leu Leu Ala Asp Ala Val Ser Ser His Phe Arg
        580                 585                 590

Arg Ile Gly Gly Pro Lys Asn Leu Thr Ser Asn Leu Glu Glu Leu Ile
    595                 600                 605

Ser Leu Val Pro Phe Asp Asp Ala Tyr Ser Gly Ser Leu Arg Glu Ala
610                 615                 620

Trp Lys Gln Trp Leu Met Ala Trp Thr Ala Lys Glu Ser Ser Gln Glu
625                 630                 635                 640

Ser Ile Glu Gly Asp Thr Ala Ile Leu Leu Val Arg Ala Ile Glu Ile
            645                 650                 655

Phe Gly Gly Arg His Val Leu Thr Gly Gln Arg Pro Asp Leu Trp Glu
        660                 665                 670

Tyr Ser Gln Leu Glu Gln Leu Thr Ser Ser Ile Cys Arg Lys Leu Tyr
    675                 680                 685

Arg Arg Val Leu Ala Gln Glu Asn Gly Lys Ser Thr Glu Lys Val Glu
690                 695                 700

Glu Ile Asp Gln Gln Leu Asp Leu Glu Met Gln Glu Leu Thr Arg Arg
705                 710                 715                 720

Val Leu Gln Gly Cys Ser Ala Ile Asn Arg Leu Thr Arg Glu Thr Phe
            725                 730                 735

Leu His Val Val Lys Ser Phe Cys Tyr Val Ala Tyr Cys Ser Pro Glu
        740                 745                 750

Thr Ile Asp Asn His Ile Asp Lys Val Ile Phe Gln Asp Val Ile
    755                 760                 765

<210> SEQ ID NO 8
<211> LENGTH: 840
<212> TYPE: PRT
<213> ORGANISM: Poaceae

<400> SEQUENCE: 8

Met Ala Ser Pro Met Glu Ala Val Ala Arg Ser Ser Leu Val Leu Ala
1               5                   10                  15

Pro Arg Arg Arg Arg Ala Leu Gly Leu Leu Pro Ala Ala Ala Ala Pro
            20                  25                  30

Phe Val Leu Asp Cys Arg Arg His Asn Gly Gly Met Arg Arg Pro
        35                  40                  45

His Val Ser Phe Ala Cys Ser Ala Glu Leu Asp Thr Gly Arg Arg Gln
    50                  55                  60

Leu Pro Ser Thr Gly Thr Arg Ala Val Met Ser Ser Cys Pro Gly Tyr
65                  70                  75                  80

Val Glu Gly Arg Met Val Gly Glu Asn Thr Ser Gln Ile Asn Met Gly
```

-continued

```
                85                  90                  95
Arg Glu Ala Arg Ile Arg Arg His Leu Glu Asn Pro Glu Phe Leu Pro
            100                 105                 110
Ser Ser Tyr Asp Ile Ala Trp Val Ala Met Val Pro Leu Pro Gly Thr
            115                 120                 125
Asp His Leu Gln Ala Pro Cys Phe Pro Glu Cys Val Glu Trp Ile Leu
            130                 135                 140
Gln Asn Gln His Ser Asn Gly Ser Trp Gly Val Asn Glu Phe Asp Ser
145                 150                 155                 160
Ser Ala Ser Lys Asp Ile Leu Leu Ser Thr Leu Ala Cys Ile Ile Ala
                165                 170                 175
Leu Glu Lys Trp Asn Val Gly Ser Glu Gln Ile Arg Arg Gly Leu His
                180                 185                 190
Phe Ile Ala Lys Asn Phe Ser Ile Val Ile Asp Asp Gln Ile Ala Ala
                195                 200                 205
Pro Ile Gly Phe Asn Leu Thr Phe Pro Ala Met Val Asn Leu Ala Ile
            210                 215                 220
Lys Met Gly Leu Glu Phe Pro Ala Ser Glu Ile Ser Ile Asp Gln Ile
225                 230                 235                 240
Leu His Leu Arg Asp Met Glu Leu Lys Arg Leu Ser Gly Glu Glu Ser
                245                 250                 255
Leu Gly Lys Glu Ala Tyr Phe Ala Tyr Ile Ala Glu Gly Leu Glu Glu
            260                 265                 270
Ser Met Val Asp Trp Ser Glu Val Met Lys Phe Gln Gly Lys Asn Gly
            275                 280                 285
Ser Leu Phe Asn Ser Pro Ala Ala Thr Ala Ala Ala Leu Val His Arg
            290                 295                 300
Tyr Asp Asp Lys Ala Leu Gly Tyr Leu Tyr Ser Val Asn Lys Phe
305                 310                 315                 320
Gly Gly Glu Val Pro Thr Val Tyr Pro Leu Asn Ile Phe Ser Gln Leu
            325                 330                 335
Ser Met Val Asp Thr Leu Val Asn Ile Gly Ile Ser Arg His Phe Ser
            340                 345                 350
Ser Asp Ile Lys Arg Ile Leu Asp Lys Thr Tyr Ile Leu Trp Ser Gln
            355                 360                 365
Arg Asp Glu Glu Val Met Leu Asp Leu Pro Thr Cys Ala Met Ala Phe
            370                 375                 380
Arg Leu Leu Arg Met Asn Gly Tyr Gly Val Ser Ser Asp Asp Leu Ser
385                 390                 395                 400
His Val Ala Glu Ala Ser Thr Phe His Asn Ser Val Glu Gly Tyr Leu
                405                 410                 415
Asp Asp Thr Lys Ser Leu Leu Glu Leu Tyr Lys Ala Ser Lys Val Ser
            420                 425                 430
Leu Ser Glu Asn Glu Pro Ile Leu Glu Lys Met Gly Cys Trp Ser Gly
            435                 440                 445
Ser Leu Leu Lys Glu Lys Leu Cys Ser Asp Asp Ile Arg Gly Thr Pro
            450                 455                 460
Ile Leu Gly Glu Val Glu Tyr Ala Leu Lys Phe Pro Phe Tyr Ala Thr
465                 470                 475                 480
Leu Glu Pro Leu Asp His Lys Trp Asn Ile Glu Asn Phe Asp Ala Arg
                485                 490                 495
Ala Tyr Gln Lys Ile Lys Thr Lys Asn Met Pro Cys His Val Asn Glu
            500                 505                 510
```

```
Asp Leu Leu Ala Leu Ala Ala Glu Asp Phe Ser Phe Cys Gln Ser Thr
        515                 520                 525

Tyr Gln Asn Glu Ile Gln His Leu Glu Ser Trp Glu Lys Glu Asn Lys
    530                 535                 540

Leu Asp Gln Leu Glu Phe Thr Arg Lys Asn Leu Ile Asn Ser Tyr Leu
545                 550                 555                 560

Ser Ala Ala Thr Ile Ser Pro Tyr Glu Leu Ser Asp Ala Arg Ile
            565                 570                 575

Ala Cys Ala Lys Ser Ile Ala Leu Thr Leu Val Ala Asp Asp Phe Phe
                580                 585                 590

Asp Val Gly Ser Ser Lys Glu Glu Gln Glu Asn Leu Ile Ser Leu Val
            595                 600                 605

Glu Lys Trp Asp Gln Tyr His Lys Val Glu Phe Tyr Ser Glu Asn Val
        610                 615                 620

Lys Ala Val Phe Phe Ala Leu Tyr Ser Thr Val Asn Gln Leu Gly Ala
625                 630                 635                 640

Met Ala Ser Ala Val Gln Asn Arg Asp Val Thr Lys Tyr Asn Val Glu
                645                 650                 655

Ser Trp Leu Asp Tyr Leu Arg Ser Leu Ala Thr Asp Ala Glu Trp Gln
            660                 665                 670

Arg Ser Lys Tyr Val Pro Thr Met Glu Glu Tyr Met Lys Asn Ser Ile
        675                 680                 685

Val Thr Phe Ala Leu Gly Pro Thr Ile Leu Ile Ala Leu Tyr Phe Met
690                 695                 700

Gly Gln Asn Leu Trp Glu Asp Ile Val Lys Asn Ala Glu Tyr Asp Glu
705                 710                 715                 720

Leu Phe Arg Leu Met Asn Thr Cys Gly Arg Leu Gln Asn Asp Ile Gln
                725                 730                 735

Ser Phe Glu Arg Glu Cys Lys Asp Gly Lys Leu Asn Ser Val Ser Leu
            740                 745                 750

Leu Val Leu Asp Ser Lys Asp Val Met Ser Val Glu Glu Ala Lys Glu
        755                 760                 765

Ala Ile Asn Glu Ser Ile Ser Ser Cys Arg Arg Glu Leu Leu Arg Leu
770                 775                 780

Val Val Arg Glu Asp Gly Val Ile Pro Lys Ser Cys Lys Glu Met Phe
785                 790                 795                 800

Trp Asn Leu Tyr Lys Thr Ser His Val Phe Tyr Ser Gln Ala Asp Gly
                805                 810                 815

Phe Ser Ser Pro Lys Glu Met Met Gly Ala Met Asn Gly Val Ile Phe
            820                 825                 830

Glu Pro Leu Lys Thr Arg Gly Asn
        835                 840

<210> SEQ ID NO 9
<211> LENGTH: 2604
<212> TYPE: DNA
<213> ORGANISM: Poaceae

<400> SEQUENCE: 9
atgattcacc tccactcccc gccgacggcg cccgccgcat tcggcggcgc cggctcggcg     60
gactggcggc ggcggcggcg gtggtcatgg tcgtcgtcgt cccgcgctcc ggtggctaaa    120
ggtggccatc ttcgtccgtg cgtttggcgg cgcggcggcg acgacggcgg cggcgaggat    180
catcacgccg acagcggcgg cggcggcgga ggaggagcgg cgtggagggc gcgggccacc    240
```

```
accgccggcg tgtcgagctc cagcagtaca gccaaagggc tgcaagccaa catcatcgaa    300
catgagaccc cccggatcac gaaatggccc aatgaatcac gcgacctcga cgatcaccaa    360
caaaacaacg aggctgatga ggaggcagat gatgagctgc agccactggt cgagcaggtg    420
aggtcgatgc tgtcgtccat ggaggacggc gcgatcaccg cgtcggcgta cgacacggcg    480
tgggtggcgc tggtgccgcg gctggacggc gagggcggca cgcagttccc ggccgccgtg    540
cggtggatcg tcggcagcca gctcgccgac gggtcgtggg gcgacgaggc gctcttctcc    600
gcctacgacc gcgtcatcaa caccctcgcc tgcgtcgtcg ccctcaccag atggtccctc    660
caccatgacc agtgcaagca agggcttcag tttctgaatc tgaacttgtg gaggttagca    720
gaggaggagc cggatacgat gccgattggg tttgagattg cattcccttc tcttgtggag    780
gcagctaggg gtttgggtat tgatttccca tatgatcacc ctgctctcaa gggcatttat    840
gcaaacagag aactcaagct taagaggatt ccaaaggaca tgatgcatat agtcccaact    900
tcaattctgc atagccttga agggatgcct gggctggatt ggcagaggct tctgaagctc    960
caatgcagtg atggatcctt cttgttctcc ccttcagcta ctgcttatgc tctcatgcag   1020
accggtgaca agaaatgctt cgcgtacatc gacaggatca ttaagaaatt cgacggtggc   1080
gttccgaacg tttacccggt cgatcttttt gagcacatat gggttgtcga tcggttggag   1140
cgtcttggga tatcgcggta cttccaacga gagattgaac agaacatgga ctatgtcaac   1200
aggcactgga ctgaagatgg gatttgctgg gctaggaact ccaatgtaaa agaagtggat   1260
gacaccgcta tggcttttccg tctactacgc ctccatggat acaatgtatc accaagtgtg   1320
ttcaagaatt ttgagaagga tggggagttc ttctgttttg tggggcaatc aactcaagca   1380
gtcactggga tgtataacct gaacagagca tctcagataa gttttccagg agaagacatt   1440
ttgcagcgtg caaggaattt ctcatatgag ttccttagag aaagagaagc ccaggggaca   1500
cttcatgata aatggatcat ctccaaggac ctaccaggag aggtacaata cacactagat   1560
tttccttggt atgcgagctt gccacgcgtc gaggcaagaa catacatagg tcaatatggt   1620
ggaaatgatg acgtctggat tggaaagaca ctctacagga tgccaattgt gaataacgct   1680
acatatctcg agttggcgaa acaggatttc aaccgttgtc aagctctaca tcagcatgag   1740
ttgcagggtc tacaaaagtg gttcattgag aatggcctgg aagcttttgg gatgacacct   1800
gaagatgttt tgagagctta ttttttggct gccgcgtgca ttttcgaacc aaaccgtgcc   1860
tctgagcgac ttgcatgggc tagagtgtca gtgctggcca acactatttc taggcatttt   1920
tacagcgata tgtcaagcat gaaaaggatg gagcgtttca tgtggagcag cctctatgaa   1980
gaaaatggca atgtttttggg gctagaagga tatgcaaaag atggaatcct tgcgaggaca   2040
ctttgtcaac ttatagattt gttgtctcaa gagacaccgc cagttcgaga aggtcaaaag   2100
tgtattcata atctcataag atgtgcttgg attgaatgga tgatgcaaca aatcaatatg   2160
aaggatggca gatatgacaa aggcagagtt atgcatccag ggtcatgcac tgttcataat   2220
aaagaaacat gtttacttat tgctcaaatt gttgaaattt gtgctggacg aattgaggag   2280
gcagcatcta tgataaataa caccgaaggt tcttggttta ttcaacttgc ttcctctatt   2340
tgcgattctc ttcatgccaa gatgttactt tcacaggata ccaagaaaaa tgagacaaca   2400
ataaatcaaa ttgacaagga aattgagttg ggtatgcaag aacttgctca atatcttctt   2460
ccaagagttg atgatagaag aattaacaac aaaaccaagc agaccttctt gagcattgtg   2520
aaaagctgtt actatgctgc caattgctca ccacatatgc ttgaccaaca catttctgaa   2580
``` gtgattttg agcaagttat ttga                                                2604

<210> SEQ ID NO 10
<211> LENGTH: 2403
<212> TYPE: DNA
<213> ORGANISM: Poaceae

<400> SEQUENCE: 10

| | | | | | |
|---|---|---|---|---|---|
| atgcagatgc | aggtgctcac | cgctgcttct | tcgctccctc | gcgcgacctt | gctccggccg | 60 |
| gcggctgccg | agccatggcg | ccaatctttc | ctgcagctgc | aggctcgtcc | aatccagcga | 120 |
| ccaggtatca | tgctacactg | caaggcccag | ctacagggga | aggaaacgcg | cgagcgtcgt | 180 |
| cagctcgacg | acgatgaaca | cgctagacca | ccacagggcg | gcgacgacga | cgtcgcagca | 240 |
| agcaccagcg | agctacccta | catgatcgag | tccatcaaat | ccaagctgag | gcggccagg | 300 |
| aacagcctcg | gcgagaccac | cgtctccgcc | tacgacacgg | cgtggatcgc | gctcgtcaac | 360 |
| cgcctcgacg | gcggcggcga | gaggagcccc | cagttcccgg | aggccatcga | ctggatcgcc | 420 |
| cggaaccagc | tgcccgacgg | ctcgtggggc | gacgccggca | tgttcatcgt | ccaggaccgg | 480 |
| ctcatcaaca | cgctgggctg | cgtcgtgcg | ctcgcgacgt | ggggcgtcca | cgaggagcag | 540 |
| cgcgcgaggg | gcctcgccta | catccaggac | aacctctgga | ggctcggcga | ggacgacgag | 600 |
| gagtggatga | tggtcgggtt | cgagatcacc | ttccccgttc | tcctcgagaa | ggccaagaac | 660 |
| ctgggcctgg | acatcaacta | tgatgaccct | gccttgcagg | acatatatgc | caagagacaa | 720 |
| ttaaagctcg | caaagattcc | tagagaagca | ctgcatgcta | gccgaccac | cttgctccat | 780 |
| agcttagagg | gaatggaaaa | cttggactgg | gaaaggttgc | tacagttcaa | gtgtccagct | 840 |
| ggctccttac | attcctcacc | tgctgcgtca | gcttacgctc | tcagcgaaac | aggtgacaag | 900 |
| gagttgctcg | aatacctgga | aacagccatc | aacaattttg | acggtggagc | accatgcacc | 960 |
| tacccctgtcg | acaactttga | ccgcttatgg | tcggtcgatc | ggttgaggcg | gctaggaata | 1020 |
| tcgaggtact | tcacgagtga | gattgaagaa | tacttggagt | acgcctacag | gcacctgagt | 1080 |
| ccagatggca | tgagctacgg | cgggctctgt | ccggtcaagg | acatcgacga | cacggccatg | 1140 |
| gctttccgtc | tcctccgtct | gcatggctac | aatgtctcat | catcggtgtt | caatcacttc | 1200 |
| gagaaggacg | gggagtactt | ctgcttcgcg | gggcagtcga | gccagtcgct | gacggcgatg | 1260 |
| tacaactcct | accgcgcctc | gcagatcgtc | ttccccggcg | acgacgacgg | cctggagcag | 1320 |
| ctcagggcct | actgccgcgc | cttcctcgag | gagcggcgag | ccaccggcaa | cctcagggac | 1380 |
| aagtgggtca | tcgccaatgg | cttgcccagc | gaggtcgagt | acgcgctgga | tttcccatgg | 1440 |
| aaggcaagct | tgccgcgagt | cgagacgagg | gtgtatctgg | agcagtacgg | cgctagcgag | 1500 |
| gacgcgtgga | tcggcaaggg | actctacagg | atgaccctag | tcaacaacga | cctgtacctt | 1560 |
| gaggcggcaa | aggctgactt | caccaacttc | cagaggctct | cccggctcga | gtggctcagc | 1620 |
| ctgaaaaggt | ggtacatcag | gaacaatctg | caagcgcacg | gcgtgaccga | acagagcgtg | 1680 |
| ctgagagcct | acttcttagc | gcgcggcgaac | atcttcgagc | ccaaccgggc | ggcggaacgc | 1740 |
| ctgggatggg | ctcgcacggc | gatcctcgcc | gaggccatcg | cgtcacacct | ccgacagtac | 1800 |
| agtgccaacg | cgccgccga | cggcatgaca | gagaggctca | tcagtggact | cgccagccac | 1860 |
| gactgggact | ggagggaatc | aaacgattca | gcagcgagga | gcttactgta | cgcacttgat | 1920 |
| gagctcatcg | acctccatgc | gttcggcaat | gcttctgaca | gcctacgtga | agcgtggaag | 1980 |
| cagtggctca | tgtcatggac | aaacgagagc | caaggatcaa | ctggtgggga | taccgcattg | 2040 |
| ctgctagttc | gcacaatcga | gatctgctca | ggacggcacg | gttcagccga | gcagagcctg | 2100 |

| | |
|---|---|
| aagaacagtg aagactacgc caggcttgag cagatcgcct cttccatgtg cagcaaactt | 2160 |
| gccaccaaaa ttcttgctca gaatggagga agcatggaca acgttgaggg tatagaccag | 2220 |
| gaagtggatg ttgagatgaa agagctcatc cagcgtgtct acgggagcag cagcaacgat | 2280 |
| gtcagcagcg tgacgaggca gacatttctc gacgtggtga agagcttttg ctacgtcgct | 2340 |
| cattgctcgc ccgaaacaat cgatgggcac atctccaagg ttttgttcga ggatgtcaat | 2400 |
| tag | 2403 |

```
<210> SEQ ID NO 11
<211> LENGTH: 204
<212> TYPE: DNA
<213> ORGANISM: Poaceae

<400> SEQUENCE: 11
```

| | |
|---|---|
| actacgccga dacagtgtgg tggtgagccg gtgatcgatc ttgcatcttg cgagcacacg | 60 |
| ggattccaga tcgatcgagc tatagctagc tagctaatta gttaccacgt acgaacgagt | 120 |
| actttacaac tcgatcagtt catcaaatta actcgatcag tggttaagtt tcgcacgaca | 180 |
| cacgcgcgcg gatcggaagc catc | 204 |

```
<210> SEQ ID NO 12
<211> LENGTH: 177
<212> TYPE: DNA
<213> ORGANISM: Poaceae

<400> SEQUENCE: 12
```

| | |
|---|---|
| gaaaatggtt gactactaga aaggcaataa aaacaagagt tgtgtctacc agcatggctc | 60 |
| gtaaagtgat gactgcgaaa attttctcaa agtgagatga atttagtcga tatttgtttc | 120 |
| acttgatggt acaccagata cacatgttgt tataaaaaaa aaaaaaaaaa aaaaaaa | 177 |

```
<210> SEQ ID NO 13
<211> LENGTH: 2304
<212> TYPE: DNA
<213> ORGANISM: Poaceae

<400> SEQUENCE: 13
```

| | |
|---|---|
| atgccggtct tcactgcgtc attccagtgt gtcaccttgt ttgggcagcc agcatcggcg | 60 |
| gccgacgccc agccattgct gcaagggcaa cggccgttcc tacaccttca cgctcgccgc | 120 |
| cgtcgaccat gcgggcccat gctaataagc aaatcaccgc cgtacccggc ctcggaagaa | 180 |
| acacgcgaat gggaagcaga aggacaacat gaacacacgg atgaactaag agagacgacg | 240 |
| acaaccatga tcgatggcat caggacagca ctgagatcaa tcggagaggg agagattagc | 300 |
| atctcagcct atgacacttc gttggttgcc cttctgaaga ggctagatgg gggtgatggt | 360 |
| cctcagttcc catcaaccat cgactggatc gttcagaatc agctaccgga tggttcatgg | 420 |
| ggtgatgcct ccttcttcat gatgggagac cggatcatga gcaccctcgc ttgtgttgta | 480 |
| gcgttgaagt catggaacat ccacaccgat aaatgcgaga gaggtttgtt gtttatccaa | 540 |
| gaaaatatgt ggaggttggc ccatgaggaa gaagactgga tgctagttgg atttgagatt | 600 |
| gccttgccct cgctcctaga catggctaag gacctggatc ttgacatccc ttacgatgag | 660 |
| ccagccttga agcaatatat tgccgagaga gaaaggaagc ttgccaagat tccaagagac | 720 |
| gtgctacacg ctatgccaac aactttactt catagccttg agggaatggt tgacttggac | 780 |
| tgggaaaagc tcctcaagct ccggtgtctc gatgggtcct ccattgctc ccctgcttcg | 840 |

```
acggctactg ctttccagca aacaggagac cagaaatgct ttgaatacct cgatggaatc      900
gtcaaaaagt tcaatggagg agttccctgt atctacccct tggatgtgta cgaacgctta      960
tgggccgtcg ataggctgac gaggctgggc atatcaaggc acttcacaag tgaaattgag     1020
gattgcttag actacatttt caggaactgg actccagatg gattagctca cacaaagaac     1080
tgcccggtaa agatatcga tgacacggcc atgggtttcc gtctcctccg actttacggc     1140
taccaagtcg acccatgcgt gttgaagaag ttcgaaaagg atggcaagtt cttctgcttg     1200
cacggggagt ccaacccatc ctctgtcacc ccaatgtaca acacttaccg ggcctcccag     1260
ctcaaatttc ctggcgatga cggtgtcctt gggcgagctg aggtgttttg ccgctcattc     1320
ctccaagaca ggagaggctc aaacagaatg aaggacaagt gggccatcgc caaggatatc     1380
ccaggcgagg ttgagtatgc tatggactac ccatggaaag caagtttacc gcgtattgaa     1440
acaaggttgt acttggatca atatggaggt agtggcgatg tatggattgg aaggtcctg      1500 cacaggatga ctcttttctg caacgacctg tacctcaagg cagctaaagc tgacttcagt     1560
aatttccaga aagagtgccg agttgagttg aatggcctta aaggtggta tttgaggagt      1620 aatctggaga ggtttggagg gactgatcca cagactacac tgatgacatc ctacttctta     1680
gcttcagcga acatcttcga gccaaaccga gcagcggaac gtcttggatg ggctcgcgta     1740
gcgttgcttg ccgatgccgt ctcctctcac ttcaggagaa tcgggggacc aaaaaatttg     1800
accagtaatc ttgaagagct tatcagcctt gttccatttg acgacgctta ttctggcagt     1860
cttcgtgaag cttggaagca gtggctcatg gcatggactg caaggagag cagccaggag     1920 tcaattgaag gggacacggc aatattgttg gttcgtgcca tcgagatttt tggaggacgg     1980
catgttttga ctgggcaaag accggacctt tgggagtatt cccagctcga gcagctcacc     2040
tcctccatct gccgcaaact gtacaggagg gttcttgccc aggagaatgg gaaaagtacg     2100
gagaaagttg aggagataga ccagcaattg gatttggaga tgcaggaatt gactcggcgc     2160
gttcttcagg gctgcagcgc tattaacaga ctaacccggg agacgtttct ccatgtggtg     2220
aagagcttct gctatgtcgc ctactgctca cctgagacaa ttgataacca catcgacaag     2280
gtcatattcc aagatgtgat ttag                                            2304

<210> SEQ ID NO 14
<211> LENGTH: 141
<212> TYPE: DNA
<213> ORGANISM: Poaceae

<400> SEQUENCE: 14
cgactggagc acgtaggaca ctgacatgga ctgaaggagt agtaaaatca ttcatcccaa       60
tatctattgc atctgcaaga gcgatcgaga gagaaaaaca agatctatct atagcagcta      120
gctagctagc acaagaacga t                                                141

<210> SEQ ID NO 15
<211> LENGTH: 246
<212> TYPE: DNA
<213> ORGANISM: Poaceae

<400> SEQUENCE: 15
gaacaaatta ccccgactca tctacactcc ttataaaaga gagtagtggt ggtattggtt       60
ctgccacccc ccaccccact accaactccc gacttttgta taataaagat gtgtcttttg      120
tattaagttt gttgtggtgt acctcgtgtt ttttctggga tagggattaa tttcgtggct      180
ttcatgaaag gtaatttccg agtatgatac tgaacgccaa cgacaaaaaa aaaaaaaaaa      240
``` aaaaaa                                                                246

<210> SEQ ID NO 16
<211> LENGTH: 2523
<212> TYPE: DNA
<213> ORGANISM: Poaceae

<400> SEQUENCE: 16

```
atggcgagtc ctatggaagc tgtagcccgt tccagcctcg tgctcgcacc tcgccggcgg      60
cgagccctcg gcctcctccc ggcggcggcc gccccattcg tgctagattg tcgccggcgg     120
cataacggag gaatgcgtcg tcctcatgtc agcttcgcct gctcggccga gctcgacacc     180
ggtcgccggc agcttccttc cacgggggact cgagcggtga tgtcgtcctg tcccggatat     240
gttgagggga ggatggtagg agaaaataca agtcagataa acatgggacg ggaggctaga     300
atacgtaggc acttggagaa cccggagttc ttaccatctt catatgacat agcatgggtg     360
gctatggtgc cattgccggg cactgatcat cttcaagctc catgcttccc tgaatgtgtg     420
gaatggatac tacaaaacca acacagtaat gggtcgtggg gtgtcaatga atttgactca     480
tcagccagca aggatattct cctatccact ttggcatgta ttattgcact tgagaaatgg     540
aatgtcggtt cggagcaaat aaggagagga ttacatttta tcgcaaagaa tttctccatt     600
gttattgatg accagattgc tgcacctata ggcttcaacc tcacattccc tgctatggtt     660
aaccttgcca ttaagatggg tttggaattt cctgccagtg aaattagtat tgatcagatt     720
cttcacctcc gtgatatgga attgaaaaga ctgtctggtg aggaatcttt ggggaaagag     780
gcatatttcg cctatattgc tgaaggtcta gaagaaagca tggtggattg gagtgaagtt     840
atgaagttcc aggggaagaa tggatcattg ttcaactccc cggctgcaac tgctgctgca     900
ttagtccaca gatacgatga taaagccctg ggatacctat attctgttgt caataaattt     960
ggaggtgaag taccaaccgt gtatccgcta aatatatttt ctcagctttc aatggtggat    1020
actctcgtca atattggaat atctcggcac ttttctagtg atataaagcg cattttggat    1080
aagcataca ttttatggtc acagagagat gaggaagtaa tgctggattt accaacatgc    1140
gcaatggcat ttcgcctttt gcgtatgaac ggatatggtg tttcctcaga tgacttgtcc    1200
catgttgctg aagcctcaac tttccataac tcagttgaag gatacttaga tgatacaaaa    1260
tccttattag aattgtacaa agcttcaaaa gtcagtttat cagaaaatga gccaatccta    1320
gagaaaatgg gttgctggtc aggtagctta ttgaaagaaa aattgtgctc cgatgacatc    1380
cgaggaacac caatccttgg agaggtagaa tatgctctca aatttccatt ttatgccacg    1440
ctggaacctc tagaccacaa gtggaacatt gaaaattttg atgccagggc ttatcagaag    1500
ataaagacca aaaacatgcc gtgccatgtc aatgaagatc tcttggcttt ggctgctgaa    1560
gatttcagct tttgtcagtc aacttaccaa aatgaaatcc agcaccttga agttgggag    1620
aaagaaaata agctggacca gctcgaattt acgcggaaga atctaataaa cagctatctc    1680
tctgctgctg ccaccataag cccttatgaa ttgtctgatg ctcgcattgc gtgtgcaaaa    1740
tctattgcgc tcacacttgt tgccgatgac ttttttgatg tcggaagttc caagaagaa     1800
caagaaaatc tcatatccct tagtcgagaag tgggatcagt atcataaagt tgagttctac    1860
tctgagaatg taaaagcagt attttttcgct ctatattcta cggttaacca gcttggagca    1920
atggcttccg cagtacagaa ccgcgacgtt acaaaatata atgttgaatc gtggttggat    1980
tatttgaggt ctttagcgac agatgcagaa tggcaacgga gcaaatatgt gccaacaatg    2040
```

```
gaggaataca tgaaaaattc aattgtgaca ttcgcattgg gaccaactat actcatagca    2100
ctgtatttca tgggacaaaa tctctgggag gacatcgtga aaaatgcaga gtatgatgag    2160
ttgtttagac taatgaacac atgtggtcgt ctccagaatg atattcaaag ctttgagagg    2220
gaatgcaagg atggcaaact gaacagtgtg tcactgcttg ttcttgacag caaagatgtc    2280
atgtcagtag aagaggctaa agaggcgata aacgagtcta tatcatcatg tagaagagag    2340
ttgctacggt tggttgttag agaagacggt gtcattccta aatcatgcaa ggagatgttc    2400
tggaatcttt acaagacaag ccatgtgttc tactctcagg ccgatggatt ttcctcgccg    2460
aaggaaatga tgggtgctat gaatggagta atctttgagc cactgaaaac tagaggcaac    2520
tag                                                                  2523

<210> SEQ ID NO 17
<211> LENGTH: 21
<212> TYPE: DNA
<213> ORGANISM: Poaceae

<400> SEQUENCE: 17
gaaaaggatg gagcgtttca t                                              21

<210> SEQ ID NO 18
<211> LENGTH: 44
<212> TYPE: DNA
<213> ORGANISM: Poaceae

<400> SEQUENCE: 18
tcaaataact tgctcaaaaa tcacttcaga aatgtgttgg tcaa                     44

<210> SEQ ID NO 19
<211> LENGTH: 17
<212> TYPE: DNA
<213> ORGANISM: Poaceae

<400> SEQUENCE: 19
cctaccgcgc ctcgcag                                                   17

<210> SEQ ID NO 20
<211> LENGTH: 20
<212> TYPE: DNA
<213> ORGANISM: Poaceae

<400> SEQUENCE: 20
gtcgatgagc tcatcaagtg                                                20

<210> SEQ ID NO 21
<211> LENGTH: 21
<212> TYPE: DNA
<213> ORGANISM: Poaceae

<400> SEQUENCE: 21
attgcgaaat ggcaggaaac c                                              21

<210> SEQ ID NO 22
<211> LENGTH: 21
<212> TYPE: DNA
<213> ORGANISM: Poaceae

<400> SEQUENCE: 22
tcctgtcgat gtattcgaag c                                              21
```

```
<210> SEQ ID NO 23
<211> LENGTH: 21
<212> TYPE: DNA
<213> ORGANISM: Poaceae

<400> SEQUENCE: 23
atgcagatgc aggtgctcac c                                              21
```